US008148510B2

(12) United States Patent
Altier et al.

(10) Patent No.: US 8,148,510 B2
(45) Date of Patent: *Apr. 3, 2012

(54) ANTIFUNGAL POLYPEPTIDES

(75) Inventors: Daniel J. Altier, Granger, IA (US); Glen Dahlbacka, Oakland, CA (US); Irina Ellanskaya, Kyiv (UA); Natalia Ellanskaya, legal representative, Kyiv (UA); Rafael Herrmann, Wilmington, DE (US); Jennie Hunter-Cevera, Elliott City, MD (US); Billy F. McCutchen, College Station, TX (US); James K. Presnail, Avondale, PA (US); Janet A. Rice, Wilmington, DE (US); Eric Schepers, Port Deposit, MD (US); Carl R. Simmons, Des Moines, IA (US); Tamas Torok, Richmond, CA (US); Nasser Yalpani, Johnston, IA (US)

(73) Assignees: Pioneer Hi-Bred International, Inc., Johnston, IA (US); E. I. du Pont de Nemours and Company, Wilmington, DE (US); The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/795,770

(22) Filed: Jun. 8, 2010

(65) Prior Publication Data

US 2010/0303762 A1 Dec. 2, 2010

Related U.S. Application Data

(62) Division of application No. 11/833,598, filed on Aug. 3, 2007, now Pat. No. 7,772,370, which is a division of application No. 11/174,413, filed on Jul. 1, 2005, now Pat. No. 7,306,946.

(60) Provisional application No. 60/585,267, filed on Jul. 2, 2004.

(51) Int. Cl.
*C12N 15/82* (2006.01)
*A01H 1/00* (2006.01)

(52) U.S. Cl. ..................... 536/23.74; 800/279

(58) Field of Classification Search .................. 435/468, 435/320.1, 419, 471; 536/23.7
See application file for complete search history.

(56) References Cited

U.S. PATENT DOCUMENTS 7,306,946 B2 * 12/2007 Altier et al. ................... 435/468

7,700,832 B2 * 4/2010 Altier et al. ................... 800/279
7,825,294 B2 * 11/2010 Altier et al. ................... 800/279
7,923,599 B2 * 4/2011 Altier et al. ................... 800/279

FOREIGN PATENT DOCUMENTS

WO   WO 02/090384 A2   11/2002

OTHER PUBLICATIONS

Falcé,n-Perez, J.M. et al., "Functional Domain Analysis of the Yeast ABC Transporter Ycf1p by Site-directed Mutagenesis," J. Biol. Chem., 1999, pp. 23584-23590, vol. 274.
Hill, et al., "Functional Analysis of Conserved Histidines in ADP-Glucose Pyrophosphorylase From *Escherichia coli*," Biochem. Biophys. Res., 1998, pp. 573-577, vol. 244.
Lazar, et al., "Transforming Growth Factor α: Mutation of Aspartic Acid 47 and Leucine 48 Results in Different Biological Activities," Mol. Cell. Biol., 1988, pp. 1247-1252, vol. 8.
Lee, D.G., et al., "Isolation and Characterization of a Novel Antifungal Peptide from *Aspergillus niger*," *Biochemical and Biophysical Research Communications*, 1999, pp. 646-651, vol. 263.
Marcus, J.P., et al., Purification, Characterization and cDNA Cloning of an Antimicrobial Peptide From *Macadamia integrifolia*, *Eur. J. Biochem.* 1997, pp. 743-749, vol. 244.
Veronese, et al., In Defense Against Pathogens. Both Plant Sentinels and Foot Soldiers Need to Know the Enemy, *Plant Physiology*, 2003, pp. 1580-1590, vol. 131.
Database Uniprot [Online], Nov. 1, 1996 "Antifungal Properties", Database Accession No. Q01701.

* cited by examiner

*Primary Examiner* — Tekchand Saidha
(74) *Attorney, Agent, or Firm* — Alston & Bird LLP

(57) ABSTRACT

Compositions and methods for protecting a plant from a pathogen, particularly a fungal pathogen, are provided. Compositions include novel amino acid sequences, and variants and fragments thereof, for antipathogenic polypeptides that were isolated from microbial fermentation broths. Nucleic acid molecules comprising nucleotide sequences that encode the antipathogenic polypeptides of the invention are also provided. A method for inducing pathogen resistance in a plant using the nucleotide sequences disclosed herein is further provided. The method comprises introducing into a plant an expression cassette comprising a promoter operably linked to a nucleotide sequence that encodes an antipathogenic polypeptide of the invention. Compositions comprising an antipathogenic polypeptide or a transformed microorganism comprising a nucleic acid of the invention in combination with a carrier and methods of using these compositions to protect a plant from a pathogen are further provided. Transformed plants, plant cells, seeds, and microorganisms comprising a nucleotide sequence that encodes an antipathogenic polypeptide of the invention, or variant or fragment thereof, are also disclosed.

8 Claims, 10 Drawing Sheets

FIG. 1

| | | | | |
|---|---|---|---|---|
| LB-09827-1 (SEQ ID NO:7) | ~~~~~~~~~~~~~~~~~~~~~~~~~~~~~~~~~~~~~~~~~LSKF | GGEGSLEENT | CTYL.KGGKN | HVVVCGSAAN KKCKSDRHHC EVDEHHKRVD CQTPV |
| LB-09827-2 (SEQ ID NO:9) | ~~~~~~~~~~~~~~~~~~~~~~~~~~~~~~~~~~~DVQLSKF | GGECSLKENT | CTYL.KGGKN | HVVVCGSAAN KKCKSDRHHC EVDEHHKRVD CQTPV |
| LB-5197/8-1 (SEQ ID NO:3) | ~~~~~~~~~~~~~~~~~~~~~~~~~~~~~~~~~~~~~~LSKY | GGEGSLAENT | CTYL.KGGKN | QVVACCTAAN KRCKTDPRHC EVDEYKTVD CQTPV |
| CAD66625 (SEQ ID NO:61) | ~~MQLTSIAI ILFAAMGAIA NPIAAEADNL VAREAELSKY | GGECSVEENT | CTYL.KGGKD | HVVSCPSAAN LRCKIEERHC EVDEHKTVD CQTPV |
| Unk_cds2f.pk0 (SEQ ID NO:13) | ~~~MQLTSIAI ILFAAMGAIA NPIAAESDDL LARDAQLSKY | GGECSLEENT | CTYR.KDGKN | HVVSCPSAAN LRCKIEERHC EVDDHKTVD CQTPV |
| aac86132 (SEQ ID NO:60) | MQITTVALFL FAAMGGVATP IESVSNDLDA RAEAGVLAKY | TGKCHKSKNE | GKYKQDAGKD | TFLKCPKTN KCTKDGAPG TVDTWNAVD CD~~~ |
| LB-5220 (SEQ ID NO:1) | ~~~~~~~~~~~~~~~~~~~~~~~~~~~~~~~~~~~~~~~~LKY | TGTCTRANNQ | CKYKGQNDRD | HVVKCPTPAN KCTEDGAPC SKDSYSRAVT CD~~~ |
| F_graminearu (SEQ ID NO:17) | ~~~~~~~~~~~~~~~~~~~~~~~~~~~~~~~~~~~~~~~~LEY | WGKCTKAEKR | CKYAKNDKGKD | VIQNCPKTDN KCTKDGNSC KVDSASKAIT GY~~~ |
| LB-5197/8-2 (SEQ ID NO:5) | ~~~~~~~~~~~~~~~~~~~~~~~~~~~~~~~~~~~~~~~~IQY | TGKCYHNGMA | CKYDSD.GKT | HVVKCPSAAN KCEKDGHKC KVDSYNGKVK GDFRH |
| aae78772 (SEQ ID NO:59) | ~~~~~~~~~~~~~~~~~~~~~~~~~~~~~~~~~~MQ EMRARVLATY | NGKCYKKDNI | CKYAKAQSGKT | ARCKGYV KKCPRDGAKC EPDSYKGKCY C~~~ |
| Consensus 1 (SEQ ID NO:39) | GXCXXXXXNX | CXYXXXX-XXX | XXVXCXXXAN XXCXXDXXXC XXDXXXXXVX C |
| Consensus 2 (SEQ ID NO:40) | GXCXXXXXNX | CXYXXXXXXXX | XXVXCXXXAN XXCXXDXXXC XXDXXXXXVX C |

FIG. 2

```
                                1                                                       50           62
Unk_cds2f.pk0(SEQ ID NO:13) ~~~~LSKYGGE CSLEHNTCTY R.KDGKNHVV SCPSAANLRC KTDRHHCEYD DHHKTVDCQT PV
LB-09827-1   (SEQ ID NO:7)  ~~~~LSKFGGE CSLKHNTCTY L.RGGKNHVV NCGSAANKKC KSDRHHCEYD EHHKRVDCQT PV
LB-09827-2   (SEQ ID NO:9)  DVQLSKFGGE CSLKHNTCTY L.RGGKNHVV NCGSAANKKC KSDRHHCEYD EHHKRVDCQT PV
LB-5197/8-1  (SEQ ID NO:3)  ~~~~LSKYGGE CSLAHNTCTY L.RGGKNQVV ACGTAANKRC KTDRHHCEYD EYHKTVDCQT PV
LB-5220      (SEQ ID NO:1)  ~~~~LKYTGT CTRANNQCKY KGQNDRDTFV KCPTFANKKC TRDGAPCSFD SYSRAVTCD~ ~~
LB-5197/8-2  (SEQ ID NO:5)  ~~~~IQYTGK CYTNGNNCKY DSD.GKTHFV KCPSAANTKC EKDGNKCTYD SYNGKVKCDF RH
```

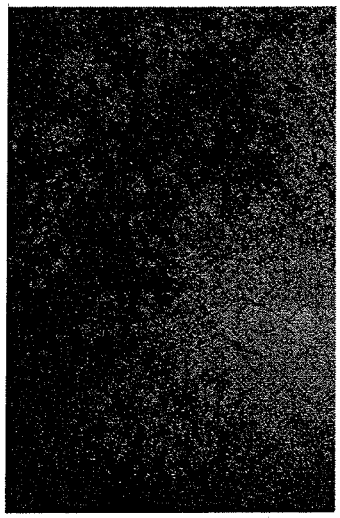 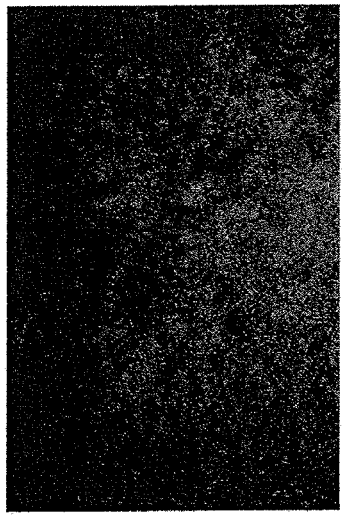 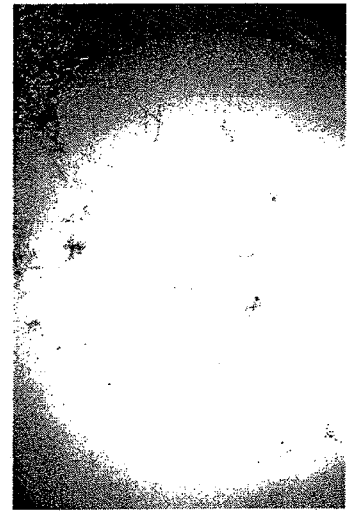
FIG. 7

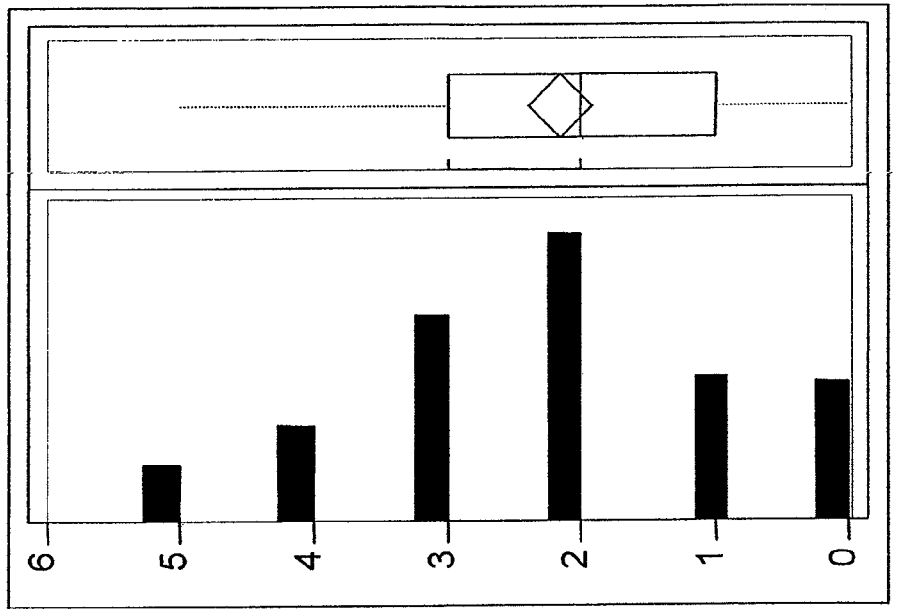
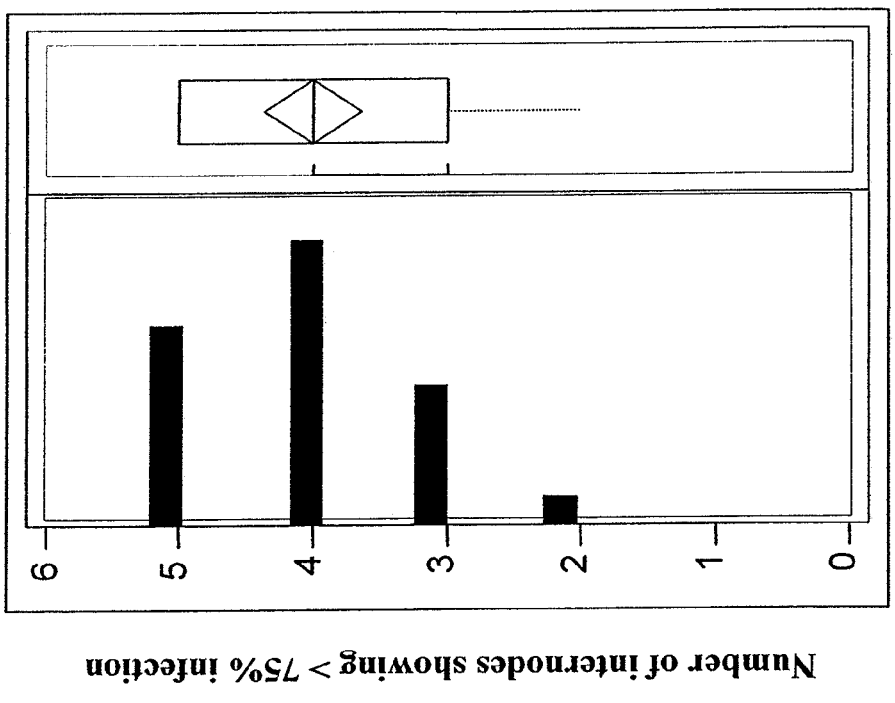
FIG. 10

SEQUENCE LISTING

```
<160> NUMBER OF SEQ ID NOS: 75

<210> SEQ ID NO 1
<211> LENGTH: 55
<212> TYPE: PRT
<213> ORGANISM: Penicillium simplicissimum

<400> SEQUENCE: 1

Leu Lys Tyr Thr Gly Thr Cys Thr Arg Ala Asn Asn Gln Cys Lys Tyr
 1               5                  10                  15

Lys Gly Gln Asn Asp Arg Asp Thr Phe Val Lys Cys Pro Thr Phe Ala
            20                  25                  30

Asn Lys Lys Cys Thr Arg Asp Gly Ala Pro Cys Ser Phe Asp Ser Tyr
        35                  40                  45

Ser Arg Ala Val Thr Cys Asp
    50                  55

<210> SEQ ID NO 2
<211> LENGTH: 168
<212> TYPE: DNA
<213> ORGANISM: Artificial Sequence
<220> FEATURE:
```

-continued

```
<223> OTHER INFORMATION: Deduced nucleotide sequence encoding the amino
      acid sequence of SEQ ID NO:1

<400> SEQUENCE: 2
ctcaagtaca ccggcacctg cacccgcgcc aacaaccagt gcaagtataa gggccagaac      60
gatcgcgaca cattcgtcaa atgcccgact tttgcgaaca agaagtgtac aagggatggc     120
gctccttgct ccttcgacag ctactctaga gcagtgactt gcgattag                  168

<210> SEQ ID NO 3
<211> LENGTH: 57
<212> TYPE: PRT
<213> ORGANISM: Penicillium miczyinskii

<400> SEQUENCE: 3

Ile Gln Tyr Thr Gly Lys Cys Tyr Thr Asn Gly Asn Asn Cys Lys Tyr
 1               5                  10                  15

Asp Ser Asp Gly Lys Thr His Phe Val Lys Cys Pro Ser Ala Ala Asn
            20                  25                  30

Thr Lys Cys Glu Lys Asp Gly Asn Lys Cys Thr Tyr Asp Ser Tyr Asn
        35                  40                  45

Gly Lys Val Lys Cys Asp Phe Arg His
    50                  55

<210> SEQ ID NO 4
<211> LENGTH: 174
<212> TYPE: DNA
<213> ORGANISM: Artificial Sequence
<220> FEATURE:
<223> OTHER INFORMATION: Deduced nucleotide sequence encoding the amino
      acid sequence of SEQ ID NO:3

<400> SEQUENCE: 4
atccagtaca ccggcaagtg ctacaccaac ggcaacaact gcaagtacga cagcgacggc      60 aagaccccact tcgtcaagtg cccgagcgcc gccaacacca gtgcgagaa agatggtaac    120 aagtgcactt acgactctta caacggaaag gtgaagtgcg acttcaggca ttag            174

<210> SEQ ID NO 5
<211> LENGTH: 58
<212> TYPE: PRT
<213> ORGANISM: Penicillium miczyinskii

<400> SEQUENCE: 5

Leu Ser Lys Tyr Gly Gly Glu Cys Ser Leu Ala His Asn Thr Cys Thr
 1               5                  10                  15

Tyr Leu Lys Gly Gly Lys Asn Gln Val Val Ala Cys Gly Thr Ala Ala
            20                  25                  30

Asn Lys Arg Cys Lys Thr Asp Arg His His Cys Glu Tyr Asp Glu Tyr
        35                  40                  45

His Lys Thr Val Asp Cys Gln Thr Pro Val
    50                  55

<210> SEQ ID NO 6
<211> LENGTH: 177
<212> TYPE: DNA
<213> ORGANISM: Artificial Sequence
<220> FEATURE:
<223> OTHER INFORMATION: Deduced nucleotide sequence encoding the amino
      acid sequence of SEQ ID NO:5

<400> SEQUENCE: 6
ctcagcaagt acggcggcga gtgcagcctc gcccacaaca cctgcaccta cctcaaaggc      60
```

```
ggtaagaatc aagtggtcgc gtgcggaacg gctgcgaaca agaggtgtaa gacagaccga    120
catcactgcg aatatgatga gtaccacaag actgttgatt gtcagactcc agtttag      177
```

<210> SEQ ID NO 7
<211> LENGTH: 58
<212> TYPE: PRT
<213> ORGANISM: Monascus ruber

<400> SEQUENCE: 7

```
Leu Ser Lys Phe Gly Gly Glu Cys Ser Leu Lys His Asn Thr Cys Thr
 1               5                  10                  15

Tyr Leu Lys Gly Gly Lys Asn His Val Val Asn Cys Gly Ser Ala Ala
            20                  25                  30

Asn Lys Lys Cys Lys Ser Asp Arg His His Cys Glu Tyr Asp Glu His
        35                  40                  45

His Lys Arg Val Asp Cys Gln Thr Pro Val
    50                  55
```

<210> SEQ ID NO 8
<211> LENGTH: 177
<212> TYPE: DNA
<213> ORGANISM: Artificial Sequence
<220> FEATURE:
<223> OTHER INFORMATION: Deduced nucleotide sequence encoding the amino
      acid sequence of SEQ ID NO:7

<400> SEQUENCE: 8

```
ctcagcaagt tcggcggcga gtgcagcctc aagcacaaca cctgcaccta cctcaagggc    60
ggcaagaatc atgtggtcaa ctgcggatct gccgctaaca gaagtgtaa gtcagacagg     120 catcattgtg aatacgatga acaccacaag cgagttgact gccagacccc agtctag       177
```

<210> SEQ ID NO 9
<211> LENGTH: 61
<212> TYPE: PRT
<213> ORGANISM: Monascus ruber

<400> SEQUENCE: 9

```
Asp Val Gln Leu Ser Lys Phe Gly Gly Glu Cys Ser Leu Lys His Asn
 1               5                  10                  15

Thr Cys Thr Tyr Leu Lys Gly Gly Lys Asn His Val Val Asn Cys Gly
            20                  25                  30

Ser Ala Ala Asn Lys Lys Cys Lys Ser Asp Arg His His Cys Glu Tyr
        35                  40                  45

Asp Glu His His Lys Arg Val Asp Cys Gln Thr Pro Val
    50                  55                  60
```

<210> SEQ ID NO 10
<211> LENGTH: 186
<212> TYPE: DNA
<213> ORGANISM: Artificial Sequence
<220> FEATURE:
<223> OTHER INFORMATION: Deduced nucleotide sequence encoding the amino
      acid sequence of SEQ ID NO:9

<400> SEQUENCE: 10

```
gacgtccagc tcagcaagtt cggcggcgag tgcagcctca agcacaacac ctgcacctac    60 ctcaagggg gtaagaatca tgtggtcaac tgcggatctg ccgctaacaa gaagtgtaag    120
tcagataggc atcattgtga atacgatgaa caccacaagc gagttgactg ccagacccca   180
gtctag                                                             186
```

```
<210> SEQ ID NO 11
<211> LENGTH: 92
<212> TYPE: PRT
<213> ORGANISM: Unknown
<220> FEATURE:
<223> OTHER INFORMATION: Propeptide isolated from fungal contaminant of
      Zea mays (Unk_cds2F.pk001.18)
<221> NAME/KEY: PEPTIDE
<222> LOCATION: (35)...(92)
<223> OTHER INFORMATION: Mature peptide

<400> SEQUENCE: 11

Met Gln Leu Thr Ser Ile Ala Ile Ile Leu Phe Ala Ala Met Gly Ala
 1               5                  10                  15

Ile Ala Asn Pro Ile Ala Ala Glu Ser Asp Asp Leu Leu Ala Arg Asp
            20                  25                  30

Ala Gln Leu Ser Lys Tyr Gly Gly Glu Cys Ser Leu Glu His Asn Thr
        35                  40                  45

Cys Thr Tyr Arg Lys Asp Gly Lys Asn His Val Val Ser Cys Pro Ser
50                  55                  60

Ala Ala Asn Leu Arg Cys Lys Thr Asp Arg His His Cys Glu Tyr Asp
65                  70                  75                  80

Asp His His Lys Thr Val Asp Cys Gln Thr Pro Val
                85                  90

<210> SEQ ID NO 12
<211> LENGTH: 279
<212> TYPE: DNA
<213> ORGANISM: Artificial Sequence
<220> FEATURE:
<223> OTHER INFORMATION: Deduced nucleotide sequence encoding the amino
      acid sequence of SEQ ID NO:11

<400> SEQUENCE: 12
atgcagctca ccagcatcgc catcatcctc ttcgccgcca tgggcgcgat tgcgaatcca     60
atcgccgcgg agtccgacga tctgctcgct cgggatgcac aattgtcgaa gtacggtggc    120
gagtgctctc ttgaacataa tacctgtacg tatcgcaagg atggcaagaa ccatgtggtt    180
tcatgcccga gtgccgccaa cctaaggtgt aagacagaca gacatcactg tgagtacgac    240
gatcaccaca agactgttga ttgccagaca ccagtttag                           279

<210> SEQ ID NO 13
<211> LENGTH: 58
<212> TYPE: PRT
<213> ORGANISM: Unknown
<220> FEATURE:
<223> OTHER INFORMATION: Mature peptide isolated from fungal contaminant
      of Zea mays (Unk_cds2F.pk001.18)

<400> SEQUENCE: 13

Leu Ser Lys Tyr Gly Gly Glu Cys Ser Leu Glu His Asn Thr Cys Thr
 1               5                  10                  15

Tyr Arg Lys Asp Gly Lys Asn His Val Val Ser Cys Pro Ser Ala Ala
            20                  25                  30

Asn Leu Arg Cys Lys Thr Asp Arg His His Cys Glu Tyr Asp Asp His
        35                  40                  45

His Lys Thr Val Asp Cys Gln Thr Pro Val
50                  55

<210> SEQ ID NO 14
<211> LENGTH: 177
```

-continued

```
<212> TYPE: DNA
<213> ORGANISM: Artificial Sequence
<220> FEATURE:
<223> OTHER INFORMATION: Deduced nucleotide sequence encoding the amino
      acid sequence of SEQ ID NO:13

<400> SEQUENCE: 14
ctcagcaagt acggcggcga gtgcagcctc gagcacaaca cctgcaccta tcgcaaggat      60
ggcaagaatc atgtggtctc ttgcccgtca gccgctaact taaggtgtaa gacggaccga     120
catcactgcg agtacgatga ccaccacaag acagttgatt gccaaacacc agtttag        177

<210> SEQ ID NO 15
<211> LENGTH: 92
<212> TYPE: PRT
<213> ORGANISM: Fusarium graminearum
<220> FEATURE:
<221> NAME/KEY: PEPTIDE
<222> LOCATION: (38)...(92)
<223> OTHER INFORMATION: Mature peptide

<400> SEQUENCE: 15

Met Gln Phe Ser Thr Ile Ile Pro Leu Phe Val Ala Ala Met Gly Val
1               5                   10                  15

Val Ala Thr Pro Val Asn Ser Pro Ala Gln Glu Leu Asp Ala Arg Gly
            20                  25                  30

Asn Leu Phe Pro Arg Leu Glu Tyr Trp Gly L

Ser Lys Ala Leu Thr Cys Tyr
   50                  55

<210> SEQ ID NO 18
<211> LENGTH: 168
<212> TYPE: DNA
<213> ORGANISM: Artificial Sequence
<220> FEATURE:
<223> OTHER INFORMATION: Deduced nucleotide sequence encoding the amino
     acid sequence of SEQ ID NO:17

<400> SEQUENCE: 18

```
ctcgagtact ggggcaagtg caccaaggcc gagaaccgct gcaagtacaa gaacgacaag    60
ggcaaggacg tcctgcagaa ttgcccgaaa ttcgataaca agaagtgtac gaaggacggc   120
aacagctgca agtgggacag cgcgagcaag gccttaacat gttactag              168
```

<210> SEQ ID NO 19
<211> LENGTH: 240
<212> TYPE: DNA
<213> ORGANISM: Artificial Sequence
<220> FEATURE:
<223> OTHER INFORMATION: Nucleotide sequence encoding the barley
     alpha-amylase signal peptide joined to the
     nucleotide sequence of SEQ ID NO:2
<221> NAME/KEY: misc_feature
<222> LOCATION: (1)...(72)
<223> OTHER INFORMATION: Nucleotide sequence encoding the barley-alpha
     amylase signal peptide

<400> SEQUENCE: 19

```
atggccaaca agcacctgtc cctctccctc ttcctcgtgc tcctcggcct ctccgcctcc    60
ctcgcctccg gactcaagta caccggcacc tgcacccgcg ccaacaacca gtgcaagtat   120
aagggccaga cgatcgcga cacattcgtc aaatgcccga cttttgcgaa caagaagtgt   180
acaagggatg gcgctccttg ctccttcgac agctactcta gagcagtgac ttgcgattag   240
```

<210> SEQ ID NO 20
<211> LENGTH: 79
<212> TYPE: PRT
<213> ORGANISM: Artificial Sequence
<220> FEATURE:
<223> OTHER INFORMATION: Amino acid sequence encoded by the nucleotide
     sequence of SEQ ID NO:19
<221> NAME/KEY: SIGNAL
<222> LOCATION: (1)...(24)
<223> OTHER INFORMATION: Barley alpha-amylase signal peptide

<400> SEQUENCE: 20

Met Ala Asn Lys His Leu Ser Leu Ser Leu Phe Leu Val Leu Leu Gly
1             5                 10              15

Leu Ser Ala Ser Leu Ala Ser Gly Leu Lys Tyr Thr Gly Thr Cys Thr
            20                25               30

Arg Ala Asn Asn Gln Cys Lys Tyr Lys Gly Gln Asn Asp Arg Asp Thr
            35                40               45

Phe Val Lys Cys Pro Thr Phe Ala Asn Lys Lys Cys Thr Arg Asp Gly
   50                 55               60

Ala Pro Cys Ser Phe Asp Ser Tyr Ser Arg Ala Val Thr Cys Asp
65             70               75

<210> SEQ ID NO 21
<211> LENGTH: 246
<212> TYPE: DNA
<213> ORGANISM: Artificial Sequence

```
<220> FEATURE:
<223> OTHER INFORMATION: Nucleotide sequence encoding the barley
      alpha-amylase signal peptide joined to the
      nucleotide sequence of SEQ ID NO:4
<221> NAME/KEY: misc_feature
<222> LOCATION: (1)...(72)
<223> OTHER INFORMATION: Nucleotide sequence encoding the barley
      alpha-amylase signal peptide

<400> SEQUENCE: 21
atggccaaca agcacctgtc cctctccctc ttcctcgtgc tcctcggcct ctccgcctcc      60
ctcgcctccg gaatccagta caccggcaag tgctacacca acggcaacaa ctgcaagtac     120
gacagcgacg gcaagaccca cttcgtcaag tgcccgagcg ccgccaacac caagtgcgag     180
aaagatggta caagtgcac ttacgactct acaacggaa aggtgaagtg cgacttcagg       240
cattag                                                                246

<210> SEQ ID NO 22
<211> LENGTH: 81
<212> TYPE: PRT
<213> ORGANISM: Artificial Sequence
<220> FEATURE:
<223> OTHER INFORMATION: Amino acid sequence encoded by the nucleotide
      sequence of SEQ ID NO:21
<221> NAME/KEY: SIGNAL
<222> LOCATION: (1)...(24)
<223> OTHER INFORMATION: Barley alpha-amylase signal peptide

<400> SEQUENCE: 22

Met Ala Asn Lys His Leu Ser Leu Ser Leu Phe Leu Val Leu Leu Gly
1               5                   10                  15

Leu Ser Ala Ser Leu Ala Ser Gly Ile Gln Tyr Thr Gly Lys Cys Tyr
            20                  25                  30

Thr Asn Gly Asn Asn Cys Lys Tyr Asp Ser Asp Gly Lys Thr His Phe
        35                  40                  45

Val Lys Cys Pro Ser Ala Ala Asn Thr Lys Cys Glu Lys Asp Gly Asn
    50                  55                  60

Lys Cys Thr Tyr Asp Ser Tyr Asn Gly Lys Val Lys Cys Asp Phe Arg
65                  70                  75                  80

His

<210> SEQ ID NO 23
<211> LENGTH: 249
<212> TYPE: DNA
<213> ORGANISM: Artificial Sequence
<220> FEATURE:
<223> OTHER INFORMATION: Nucleotide sequence encoding the barley
      alpha-amylase signal peptide joined to the
      nucleotide sequence of SEQ ID NO:6
<221> NAME/KEY: misc_feature
<222> LOCATION: (1)...(72)
<223> OTHER INFORMATION: Nucleotide sequence encoding the barley
      alpha-amylase signal peptide

<400> SEQUENCE: 23
atggccaaca agcacctgtc cctctccctc ttcctcgtgc tcctcggcct ctccgcctcc      60
ctcgcctccg gactcagcaa gtacggcggc gagtgcagcc tcgcccacaa cacctgcacc     120
tacctcaaag gcggtaagaa tcaagtggtc gcgtgcggaa cggctgcgaa caagaggtgt     180
aagacagacc gacatcactg cgaatatgat gagtaccaca agactgttga ttgtcagact     240
ccagtttag                                                             249

<210> SEQ ID NO 24
```

```
<211> LENGTH: 82
<212> TYPE: PRT
<213> ORGANISM: Artificial Sequence
<220> FEATURE:
<223> OTHER INFORMATION: Amino acid sequence encoded by the nucleotide
      sequence of SEQ ID NO:23
<221> NAME/KEY: SIGNAL
<222> LOCATION: (1)...(24)
<223> OTHER INFORMATION: Barley alpha-amylase signal peptide

<400> SEQUENCE: 24
```

Met Ala Asn Lys His Leu Ser Leu Ser Leu Phe Leu Val Leu Leu Gly
 1               5                  10                  15

Leu Ser Ala Ser Leu Ala Ser Gly Leu Ser Lys Tyr Gly Gly Glu Cys
            20                  25                  30

Ser Leu Ala His Asn Thr Cys Thr Tyr Leu Lys Gly Gly Lys Asn Gln
        35                  40                  45

Val Val Ala Cys Gly Thr Ala Ala Asn Lys Arg Cys Lys Thr Asp Arg
    50                  55                  60

His His Cys Glu Tyr Asp Glu Tyr His Lys Thr Val Asp Cys Gln Thr
65                  70                  75                  80

Pro Val

```
<210> SEQ ID NO 25
<211> LENGTH: 249
<212> TYPE: DNA
<213> ORGANISM: Artificial Sequence
<220> FEATURE:
<223> OTHER INFORMATION: Nucleotide sequence encoding the barley
      alpha-amylase signal peptide joined to the
      nucleotide sequence of SEQ ID NO:8
<221> NAME/KEY: misc_feature
<222> LOCATION: (1)...(72)
<223> OTHER INFORMATION: Nucleotide sequence encoding the barley
      alpha-amylase signal peptide

<400> SEQUENCE: 25
atggccaaca agcacctgtc cctctccctc ttcctcgtgc tcctcggcct ctccgcctcc    60
ctcgcctccg gactcagcaa gttcggcggc gagtgcagcc tcaagcacaa cacctgcacc   120
tacctcaagg gcggcaagaa tcatgtggtc aactgcggat ctgccgctaa caagaagtgt   180
aagtcagaca ggcatcattg tgaatacgat gaacaccaca agcgagttga ctgccagacc   240
ccagtctag                                                          249

<210> SEQ ID NO 26
<211> LENGTH: 82
<212> TYPE: PRT
<213> ORGANISM: Artificial Sequence
<220> FEATURE:
<223> OTHER INFORMATION: Amino acid sequence encoded by the nucleotide
      sequence of SEQ ID NO:25
<221> NAME/KEY: SIGNAL
<222> LOCATION: (1)...(24)
<223> OTHER INFORMATION: Barley alpha-amylase signal peptide

<400> SEQUENCE: 26
```

Met Ala Asn Lys His Leu Ser Leu Ser Leu Phe Leu Val Leu Leu Gly
 1               5                  10                  15

Leu Ser Ala Ser Leu Ala Ser Gly Leu Ser Lys Phe Gly Gly Glu Cys
            20                  25                  30

Ser Leu Lys His Asn Thr Cys Thr Tyr Leu Lys Gly Gly Lys Asn His
        35                  40                  45

Val Val Asn Cys Gly Ser Ala Ala Asn Lys Lys Cys Lys Ser Asp Arg
    50                  55                  60

```
His His Cys Glu Tyr Asp Glu His His Lys Arg Val Asp Cys Gln Thr
65                  70                  75                  80

Pro Val

<210> SEQ ID NO 27
<211> LENGTH: 258
<212> TYPE: DNA
<213> ORGANISM: Artificial Sequence
<220> FEATURE:
<223> OTHER INFORMATION: Nucleotide sequence encoding the barley
      alpha-amylase signal peptide joined to the
      nucleotide sequence of SEQ ID NO:10
<221> NAME/KEY: misc_feature
<222> LOCATION: (1)...(72)
<223> OTHER INFORMATION: Nucleotide sequence encoding the barley
      alpha-amylase signal peptide

<400> SEQUENCE: 27
atggccaaca agcacctgtc cctctccctc ttcctcgtgc tcctcggcct ctccgcctcc      60
ctcgcctccg gagacgtcca gctcagcaag ttcggcggcg agtgcagcct caagcacaac     120
acctgcacct acctcaaggg gggtaagaat catgtggtca actgcggatc tgccgctaac     180
aagaagtgta agtcagatag gcatcattgt gaatacgatg aacaccacaa gcgagttgac     240
tgccagaccc cagtctag                                                   258

<210> SEQ ID NO 28
<211> LENGTH: 85
<212> TYPE: PRT
<213> ORGANISM: Artificial Sequence
<220> FEATURE:
<223> OTHER INFORMATION: Amino acid sequence encoded by the nucleotide
      sequence of SEQ ID NO:27
<221> NAME/KEY: SIGNAL
<222> LOCATION: (1)...(24)
<223> OTHER INFORMATION: Barley alpha-amylase signal peptide

<400> SEQUENCE: 28

Met Ala Asn Lys His Leu Ser Leu Ser Leu Phe Leu Val Leu Leu Gly
1                   5                   10                  15

Leu Ser Ala Ser Leu Ala Ser Gly Asp Val Gln Leu Ser Lys Phe Gly
            20                  25                  30

Gly Glu Cys Ser Leu Lys His Asn Thr Cys Thr Tyr Leu Lys Gly Gly
        35                  40                  45

Lys Asn His Val Val Asn Cys Gly Ser Ala Ala Asn Lys Lys Cys Lys
    50                  55                  60

Ser Asp Arg His His Cys Glu Tyr Asp Glu His His Lys Arg Val Asp
65                  70                  75                  80

Cys Gln Thr Pro Val
            85

<210> SEQ ID NO 29
<211> LENGTH: 249
<212> TYPE: DNA
<213> ORGANISM: Artificial Sequence
<220> FEATURE:
<223> OTHER INFORMATION: Nucleotide sequence encoding the barley
      alpha-amylase signal peptide joined to the
      nucleotide sequence of SEQ ID NO:14
<221> NAME/KEY: misc_feature
<222> LOCATION: (1)...(72)
<223> OTHER INFORMATION: Nucleotide sequence encoding the barley
      alpha-amylase signal peptide

<400> SEQUENCE: 29
```

```
atggccaaca agcacctgtc cctctccctc ttcctcgtgc tcctcggcct ctccgcctcc      60
ctcgcctccg gactcagcaa gtacggcggc gagtgcagcc tcgagcacaa cacctgcacc     120
tatcgcaagg atggcaagaa tcatgtggtc tcttgcccgt cagccgctaa cttaaggtgt     180
aagacggacc gacatcactg cgagtacgat gaccaccaca agacagttga ttgccaaaca     240
ccagtttag                                                             249
```

<210> SEQ ID NO 30
<211> LENGTH: 82
<212> TYPE: PRT
<213> ORGANISM: Artificial Sequence
<220> FEATURE:
<223> OTHER INFORMATION: Amino acid sequence encoded by the nucleotide
      sequence of SEQ ID NO:29
<221> NAME/KEY: SIGNAL
<222> LOCATION: (1)...(24)
<223> OTHER INFORMATION: Barley alpha-amylase signal peptide

<400> SEQUENCE: 30

```
Met Ala Asn Lys His Leu Ser Leu Ser Leu Phe Leu Val Leu Leu Gly
 1               5                  10                  15

Leu Ser Ala Ser Leu Ala Ser Gly Leu Ser Lys Tyr Gly Gly Glu Cys
            20                  25                  30

Ser Leu Glu His Asn Thr Cys Thr Tyr Arg Lys Asp Gly Lys Asn His
        35                  40                  45

Val Val Ser Cys Pro Ser Ala Ala Asn Leu Arg Cys Lys Thr Asp Arg
    50                  55                  60

His His Cys Glu Tyr Asp Asp His His Lys Thr Val Asp Cys Gln Thr
65                  70                  75                  80

Pro Val
```

<210> SEQ ID NO 31
<211> LENGTH: 240
<212> TYPE: DNA
<213> ORGANISM: Artificial Sequence
<220> FEATURE:
<223> OTHER INFORMATION: Nucleotide sequence encoding the barley
      alpha-amylase signal peptide joined to the
      nucleotide sequence of SEQ ID NO:18
<221> NAME/KEY: misc_feature
<222> LOCATION: (1)...(72)
<223> OTHER INFORMATION: Nucleotide sequence encoding the barley
      alpha-amylase signal peptide

<400> SEQUENCE: 31

```
atggccaaca agcacctgtc cctctccctc ttcctcgtgc tcctcggcct ctccgcctcc      60
ctcgcctccg gactcgagta ctggggcaag tgcaccaagg ccgagaaccg ctgcaagtac     120
aagaacgaca agggcaagga cgtcctgcag aattgcccga aattcgataa caagaagtgt     180
acgaaggacg gcaacagctg caagtgggac agcgcgagca aggccttaac atgttactag     240
```

<210> SEQ ID NO 32
<211> LENGTH: 79
<212> TYPE: PRT
<213> ORGANISM: Artificial Sequence
<220> FEATURE:
<223> OTHER INFORMATION: Amino acid sequence encoded by the nucleotide
      sequence of SEQ ID NO:31
<221> NAME/KEY: SIGNAL
<222> LOCATION: (1)...(24)
<223> OTHER INFORMATION: Barley alpha-amylase signal peptide

<400> SEQUENCE: 32

```
Met Ala Asn Lys His Leu Ser Leu Ser Leu Phe Leu Val Leu Leu Gly
```

```
                1               5                  10                  15
Leu Ser Ala Ser Leu Ala Ser Gly Leu Glu Tyr Trp Gly Lys Cys Thr
                20                  25                  30

Lys Ala Glu Asn Arg Cys Lys Tyr Lys Asn Asp Lys Gly Lys Asp Val
            35                  40                  45

Leu Gln Asn Cys Pro Lys Phe Asp Asn Lys Cys Thr Lys Asp Gly
        50                  55                  60

Asn Ser Cys Lys Trp Asp Ser Ala Ser Lys Ala Leu Thr Cys Tyr
65                  70                  75

<210> SEQ ID NO 33
<211> LENGTH: 438
<212> TYPE: DNA
<213> ORGANISM: Cauliflower Mosaic Virus
<220> FEATURE:
<221> NAME/KEY: enhancer
<222> LOCATION: (1)...(438)
<223> OTHER INFORMATION: 35S enhancer element

<400> SEQUENCE: 33
cccatggagt caaagattca aatagaggac ctaacagaac tcgccgtaaa gactggcgaa      60
cagttcatac agagtctctt acgactcaat gacaagaaga aaatcttcgt caacatggtg     120
gagcacgaca cgcttgtcta ctccaaaaat atcaaagata cagtctcaga agaccaaagg     180
gcaattgaga cttttcaaca aagggtaata tccggaaacc tcctcggatt ccattgccca     240
gctatctgtc actttattgt gaagatagtg gaaaggaag gtggctccta caaatgccat     300
cattgcgata aaggaaaggc catcgttgaa gatgcctctg ccgacagtgg tcccaaagat     360
ggacccccac ccacgaggag catcgtggaa aagaagacg ttccaaccac gtcttcaaag     420
caagtggatt gatgtgat                                                  438

<210> SEQ ID NO 34
<211> LENGTH: 72
<212> TYPE: DNA
<213> ORGANISM: Artificial Sequence
<220> FEATURE:
<223> OTHER INFORMATION: Nucleotide sequence encoding the barley
      alpha-amylase signal peptide

<400> SEQUENCE: 34
atggccaaca agcacctgtc cctctccctc ttcctcgtgc tcctcggcct ctccgcctcc      60
ctcgcctccg ga                                                         72

<210> SEQ ID NO 35
<211> LENGTH: 24
<212> TYPE: PRT
<213> ORGANISM: Artificial Sequence
<220> FEATURE:
<223> OTHER INFORMATION: Barley alpha-amylase signal peptide

<400> SEQUENCE: 35

Met Ala Asn Lys His Leu Ser Leu Ser Leu Phe Leu Val Leu Leu Gly
1               5                   10                  15

Leu Ser Ala Ser Leu Ala Ser Gly
            20

<210> SEQ ID NO 36
<211> LENGTH: 969
<212> TYPE: DNA
<213> ORGANISM: Zea mays
<220> FEATURE:
<221> NAME/KEY: promoter
```

```
<222> LOCATION: (1)...(969)
<223> OTHER INFORMATION: ZmPR1-81

<400> SEQUENCE: 36
agggcacgcg tggtcgacgg cccgggctgg tagtcttggt tgggtcagat gtggccgata      60
aagatgaagg caagaacaat gtcattggcg atcctcgcac gccaagtcag ttacaaggag     120
tggttacttg aaaggctctg aacaagagaa tgactaataa gactcaaggc cctagagggc     180
aaacacgacc ggatacccga ttacgatcac atgtcttgtg tacgcaggac ggtccgggac     240
ctaaggccga tcagtctaag agtgaccaaa agcaacaacg acctcagacc tttagaccat     300
gacatctaga agaaggtata tgcaagcaaa atacatctaa agcatctgac tgactcgtta     360
gtgctagccc ttcttttgaa caacttcttt ctaagtatat gaataagaag gtcgtttcac     420
acaattgatc gacaaaacga tcaatatcat ccacaacgag gaagcaatcc atgcaagggc     480
aaaagccgaa taaatcggcc caggaagtgg tgcaaccaat gtcgcctact catccgctct     540
aggaatgtcg tgttactttc caccagtcta ctcatcgatg atgttttatc ctgctgacat     600
gtgaaaaagt atgacgatga atccgtatca cacaggggcg gacgcagagg gaggcaaagt     660
gggtcatagc cacctcaatt tttatgatat tttatatatc atgacgtgca gtctctttgc     720
aaccccagcc acattaatta atagactcca ccgacgagcg acgagtgatg gtaccggccg     780
ccggcccagg ccaacccaag tggaaaaggc cgacgactcc cggacgtctc atcctcaccg     840
gacgccacca accccgcaa tctccagacg tacgagccgc ctatttaaag ccctcagtct     900
gccactctca tggcaacgca agcagaagct acaatcctaa aaccatctgc ttcagccttc     960
agctagccc                                                             969

<210> SEQ ID NO 37
<211> LENGTH: 180
<212> TYPE: DNA
<213> ORGANISM: Artificial Sequence
<220> FEATURE:
<223> OTHER INFORMATION: Nucleotide sequence encoding the amino acid
      sequence of SEQ ID NO:1 (LBNL 5220) joined with a
      nucleotide sequence encoding a carboxy-terminal
      KDEL sequence (SEQ ID NO:62)

<400> SEQUENCE: 37
ctcaagtaca ccggcacctg cacccgcgct aacaaccagt gcaagtacaa gggtcagaac      60
gatcgcgata ccttcgtgaa gtgcccaacc ttcgccaaca agaagtgcac gcgcgatggc     120
gctccttgct ccttcgactc atacagccgc gccgtcacct gcgacaagga cgagctgtga     180

<210> SEQ ID NO 38
<211> LENGTH: 59
<212> TYPE: PRT
<213> ORGANISM: Artificial Sequence
<220> FEATURE:
<223> OTHER INFORMATION: Amino acid sequence of SEQ ID NO:1 (LBNL 5220)
      joined with a carboxy-terminal KDEL sequence (SEQ
      ID NO:62)

<400> SEQUENCE: 38

Leu Lys Tyr Thr Gly Thr Cys Thr Arg Ala Asn Asn Gln Cys Lys Tyr
  1               5                  10                  15

Lys Gly Gln Asn Asp Arg Asp Thr Phe Val Lys Cys Pro Thr Phe Ala
             20                  25                  30

Asn Lys Lys Cys Thr Arg Asp Gly Ala Pro Cys Ser Phe Asp Ser Tyr
         35                  40                  45

Ser Arg Ala Val Thr Cys Asp Lys Asp Glu Leu
```

<210> SEQ ID NO 39
<211> LENGTH: 49
<212> TYPE: PRT
<213> ORGANISM: Artificial Sequence
<220> FEATURE:
<223> OTHER INFORMATION: Consensus sequence deduced from an alignment of
      antifungal polypeptides
<221> NAME/KEY: VARIANT
<222> LOCATION: 2, 4, 5, 6, 7, 9, 11, 13, 14, 15, 16, 17, 18, 19, 20,
      22, 24, 25, 26, 29, 30, 32, 33, 35, 36, 37, 39, 40, 42, 43, 44,
      45, 46, 48
<223> OTHER INFORMATION: Xaa = Any Amino Acid

<400> SEQUENCE: 39

Gly Xaa Cys Xaa Xaa Xaa Xaa Asn Xaa Cys Xaa Tyr Xaa Xaa Xaa Xaa
 1               5                  10                  15

Xaa Xaa Xaa Xaa Val Xaa Cys Xaa Xaa Xaa Ala Asn Xaa Xaa Cys Xaa
            20                  25                  30

Xaa Asp Xaa Xaa Xaa Cys Xaa Xaa Asp Xaa Xaa Xaa Xaa Val Xaa
        35                  40                  45

Cys

<210> SEQ ID NO 40
<211> LENGTH: 50
<212> TYPE: PRT
<213> ORGANISM: Artificial Sequence
<220> FEATURE:
<223> OTHER INFORMATION: Consensus sequence deduced from an alignment of
      antifungal polypeptides
<221> NAME/KEY: VARIANT
<222> LOCATION: 2, 4, 5, 6, 7, 9, 11, 13, 14, 15, 16, 17, 18, 19, 20,
      21, 23, 25, 26, 27, 30, 31, 33, 34, 36, 37, 38, 40, 41, 43, 44,
      45, 46, 47, 49
<223> OTHER INFORMATION: Xaa = Any Amino Acid

<400> SEQUENCE: 40

Gly Xaa Cys Xaa Xaa Xaa Xaa Asn Xaa Cys Xaa Tyr Xaa Xaa Xaa Xaa
 1               5                  10                  15

Xaa Xaa Xaa Xaa Xaa Val Xaa Cys Xaa Xaa Xaa Ala Asn Xaa Xaa Cys
            20                  25                  30

Xaa Xaa Asp Xaa Xaa Xaa Cys Xaa Xaa Asp Xaa Xaa Xaa Xaa Val
        35                  40                  45

Xaa Cys
    50

<210> SEQ ID NO 41
<211> LENGTH: 53
<212> TYPE: PRT
<213> ORGANISM: Artificial Sequence
<220> FEATURE:
<223> OTHER INFORMATION: Consensus sequence deduced from an alignment of
      antifungal polypeptides
<221> NAME/KEY: VARIANT
<222> LOCATION: 1
<223> OTHER INFORMATION: Xaa = Lys or Gln
<221> NAME/KEY: VARIANT
<222> LOCATION: 2, 43
<223> OTHER INFORMATION: Xaa = Tyr or Phe
<221> NAME/KEY: VARIANT
<222> LOCATION: 14
<223> OTHER INFORMATION: Xaa = Thr or Lys
<221> NAME/KEY: VARIANT
<222> LOCATION: 27
<223> OTHER INFORMATION: Xaa = Pro or Gly
<221> NAME/KEY: VARIANT
<222> LOCATION: 28
<223> OTHER INFORMATION: Xaa = Ser or Thr

```
<221> NAME/KEY: VARIANT
<222> LOCATION: 29
<223> OTHER INFORMATION: Xaa = Ala or Phe
<221> NAME/KEY: VARIANT
<222> LOCATION: 33
<223> OTHER INFORMATION: Xaa = Arg or Lys
<221> NAME/KEY: VARIANT
<222> LOCATION: 38
<223> OTHER INFORMATION: Xaa = Arg or Gly
<221> NAME/KEY: VARIANT
<222> LOCATION: 46
<223> OTHER INFORMATION: Xaa = His or Tyr
<221> NAME/KEY: VARIANT
<222> LOCATION: 53
<223> OTHER INFORMATION: Xaa = Gln or Asp
<221> NAME/KEY: VARIANT
<222> LOCATION: 3, 5, 7, 8, 9, 10, 12, 16, 17, 18, 19,20, 21, 22,
      23, 25, 32, 35, 36, 39, 40, 42, 45,47, 48, 49, 51
<223> OTHER INFORMATION: Xaa = Any amino acid

<400> SEQUENCE: 41

Xaa Xaa Xaa Gly Xaa Cys Xaa Xaa Xaa Asn Xaa Cys Xaa Tyr Xaa
 1               5                  10                  15

Xaa Xaa Xaa Xaa Xaa Xaa Xaa Val Xaa Cys Xaa Xaa Xaa Ala Asn Xaa
            20                  25                  30

Xaa Cys Xaa Xaa Asp Xaa Xaa Xaa Cys Xaa Xaa Asp Xaa Xaa Xaa Xaa
        35                  40                  45

Xaa Val Xaa Cys Xaa
    50

<210> SEQ ID NO 42
<211> LENGTH: 54
<212> TYPE: PRT
<213> ORGANISM: Artificial Sequence
<220> FEATURE:
<223> OTHER INFORMATION: Consensus sequence deduced from an alignment of
      antifungal polypeptides
<221> NAME/KEY: VARIANT
<222> LOCATION: 1
<223> OTHER INFORMATION: Xaa = Lys or Gln
<221> NAME/KEY: VARIANT
<222> LOCATION: 2, 44
<223> OTHER INFORMATION: Xaa = Tyr or Phe
<221> NAME/KEY: VARIANT
<222> LOCATION: 14
<223> OTHER INFORMATION: Xaa = Thr or Lys
<221> NAME/KEY: VARIANT
<222> LOCATION: 28
<223> OTHER INFORMATION: Xaa = Pro or Gly
<221> NAME/KEY: VARIANT
<222> LOCATION: 29
<223> OTHER INFORMATION: Xaa = Ser or Thr
<221> NAME/KEY: VARIANT
<222> LOCATION: 30
<223> OTHER INFORMATION: Xaa = Ala or Phe
<221> NAME/KEY: VARIANT
<222> LOCATION: 34
<223> OTHER INFORMATION: Xaa = Arg or Lys
<221> NAME/KEY: VARIANT
<222> LOCATION: 39
<223> OTHER INFORMATION: Xaa = Arg or Gly
<221> NAME/KEY: VARIANT
<222> LOCATION: 47
<223> OTHER INFORMATION: Xaa = His or Tyr
<221> NAME/KEY: VARIANT
<222> LOCATION: 54
<223> OTHER INFORMATION: Xaa = Gln or Asp
<221> NAME/KEY: VARIANT
<222> LOCATION: 3, 5, 7, 8, 9, 10, 12, 16, 17, 18, 19, 20, 21, 22,
      23, 24, 26, 33, 36, 37, 40, 41, 43, 46, 48, 49, 50, 52
<223> OTHER INFORMATION: Xaa = Any amino acid

<400> SEQUENCE: 42

Xaa Xaa Xaa Gly Xaa Cys Xaa Xaa Xaa Xaa Asn Xaa Cys Xaa Tyr Xaa
```

```
                1               5                   10                  15
Xaa Xaa Xaa Xaa Xaa Xaa Xaa Xaa Val Xaa Cys Xaa Xaa Xaa Ala Asn
                    20                  25                  30

Xaa Xaa Cys Xaa Xaa Asp Xaa Xaa Xaa Cys Xaa Xaa Asp Xaa Xaa Xaa
            35                  40                  45

Xaa Xaa Val Xaa Cys Xaa
    50
```

<210> SEQ ID NO 43
<211> LENGTH: 22
<212> TYPE: DNA
<213> ORGANISM: Artificial Sequence
<220> FEATURE:
<223> OTHER INFORMATION: AP1 primer

<400> SEQUENCE: 43
gtaatacgac tcactatagg gc                                        22

<210> SEQ ID NO 44
<211> LENGTH: 30
<212> TYPE: DNA
<213> ORGANISM: Artificial Sequence
<220> FEATURE:
<223> OTHER INFORMATION: gsp 12R primer
<221> NAME/KEY: misc_feature
<222> LOCATION: 7, 19
<223> OTHER INFORMATION: n = A, T, C, or G

<400> SEQUENCE: 44
rtcrtangtr cayttrttnc crtcyttytc                                30

<210> SEQ ID NO 45
<211> LENGTH: 19
<212> TYPE: DNA
<213> ORGANISM: Artificial Sequence
<220> FEATURE:
<223> OTHER INFORMATION: AP2 primer

<400> SEQUENCE: 45
actatagggc acgcgtggt                                            19

<210> SEQ ID NO 46
<211> LENGTH: 21
<212> TYPE: DNA
<213> ORGANISM: Artificial Sequence
<220> FEATURE:
<223> OTHER INFORMATION: gsp10R primer
<221> NAME/KEY: misc_feature
<222> LOCATION: 1, 10, 19
<223> OTHER INFORMATION: n = A, T, C, or G

<400> SEQUENCE: 46
nggrcayttn acraartgng t                                         21

<210> SEQ ID NO 47
<211> LENGTH: 124
<212> TYPE: DNA
<213> ORGANISM: Penicillium miczyinskii

<400> SEQUENCE: 47
aggactatag ggcacgcgtg gtcgacggct cgggctggtt aattacttgt tccagaaatg   60
ttatacaaat ggcaacaatt gtaagtacga tagtgatggg aagacccatt tcgtcaaatg  120
tccc                                                              124

```
<210> SEQ ID NO 48
<211> LENGTH: 23
<212> TYPE: PRT
<213> ORGANISM: Artificial Sequence
<220> FEATURE:
<223> OTHER INFORMATION: Mature peptide encoded by the 124 bp 5'
      fragment of the LBNL 5197/8-1 gene (SEQ ID NO:47)

<400> SEQUENCE: 48

Lys Cys Tyr Thr Asn Gly Asn Asn Cys Lys Tyr Asp Ser Asp Gly Lys
 1               5                  10                  15

Thr His Phe Val Lys Cys Pro
            20

<210> SEQ ID NO 49
<211> LENGTH: 23
<212> TYPE: DNA
<213> ORGANISM: Artificial Sequence
<220> FEATURE:
<223> OTHER INFORMATION: Forward primer phn76125

<400> SEQUENCE: 49
tggttaatta cttgttccag aaa                                            23

<210> SEQ ID NO 50
<211> LENGTH: 23
<212> TYPE: DNA
<213> ORGANISM: Artificial Sequence
<220> FEATURE:
<223> OTHER INFORMATION: Reverse primer phn76128

<400> SEQUENCE: 50
cccatcacta tcgtacttac aat                                            23

<210> SEQ ID NO 51
<211> LENGTH: 23
<212> TYPE: DNA
<213> ORGANISM: Artificial Sequence
<220> FEATURE:
<223> OTHER INFORMATION: Forward primer phn76127

<400> SEQUENCE: 51
aaatggcaac aattgtaagt acg                                            23

<210> SEQ ID NO 52
<211> LENGTH: 25
<212> TYPE: DNA
<213> ORGANISM: Artificial Sequence
<220> FEATURE:
<223> OTHER INFORMATION: Reverse primer phn76129

<400> SEQUENCE: 52
gtataacatt tctggaacaa gtaat                                          25

<210> SEQ ID NO 53
<211> LENGTH: 432
<212> TYPE: DNA
<213> ORGANISM: Penicillium miczyinskii

<400> SEQUENCE: 53
ctatagggca cgcgtggtcg acggcccggg ctggtctgaa catcttcgac tatgtaataa    60
tagcccttat taggctcaat aatctttcgg taacggcccc catgatgact gcgtcgaaaa   120
tggtgatcat gcttgtcaca tcttctacag ggatcatgat aactcctata taagacagcc   180
cctcggaaca tttgatccat cttcccaatc gtctcgacca acgattcaag ccattcacca   240
```

```
tgcagattgc caatatttcg cttttcctttt tcgctgccat gggtacgatt gctagtcccc    300
ttgatgccga gtccgacgac ctcagtgcta gagacgtgaa tgctgccgac attcagtaca    360
ccggagtgag attattacag cacatgcaga catgagaacg aagctaatta cttgttccag    420
aaatgttata cc                                                        432

<210> SEQ ID NO 54
<211> LENGTH: 960
<212> TYPE: DNA
<213> ORGANISM: Penicillium miczyinskii

<400> SEQUENCE: 54
aatggcaaca attgtaagta cgatagtgat gggaagacgc actttgtcaa gtgccctagc     60
gccgccaaca caaggtatc tttccttat aattaagcat attgacctcg actaaccttg    120
atcattaact ttcgagtgcg agaaggacgg aaataagtgc acatatgact cctacaacgg    180
aaaggtcaag tgcgacttcc gccattaatt aagctatttc aaacggctgt tcctggccat    240
tcttcttacc agcaagtgtg agatgccatg tgattctcag tgcctacaat tcgtgtcaag    300
aaaggctagg aacaagcagt attgaatatg tgttgggtga atacatatgt gatgtccatc    360
cccagtatct cgctcttctg tgattttgc tatgaccca ctcgtttatt atctagctag     420 atactttgc ttatcaatat ttttgctcat caataaattg ctcattgact gcctgatgtt    480
ttgagcatct ctgtgaatca gacaatatcc tagtcatcta tgtattgcta agtcatgcta    540
gtagcctgac actctggtag ctaccaactt ctcaacgaat ctgaccggaa ggattctctc    600
cggcagtttg aacaatccga aagtttgaca attaccagaa cctcagaaca tatatatttc    660
tatctggtgc atgtaagggg tgtaatcatt tcttatttgt ataccttaga agatatagcg    720
gacgtgcgaa gggctgcatt gagagaaaag agaaacattg aactcggaag ccaaagtagg    780
agagaagcta agaaagaagg agagagatct gatggacttc tttcttgaaa actgctttcg    840
ggccttcctt cacgtcttac ttaatttgcg ccatcctttg agtcatcctt caagtcttca    900
tttcccgtag cctcactctt taccagcccg ggccgtcgac cacgcgtgcc ctatagtcct    960

<210> SEQ ID NO 55
<211> LENGTH: 94
<212> TYPE: PRT
<213> ORGANISM: Artificial Sequence
<220> FEATURE:
<223> OTHER INFORMATION: Deduced full-length amino acid encoded by the
      LBNL 5197/8-1 gene
<221> NAME/KEY: SIGNAL
<222> LOCATION: (1)...(18)
<223> OTHER INFORMATION: Predicted signal peptide
<221> NAME/KEY: PROPEP
<222> LOCATION: (19)...(37)
<223> OTHER INFORMATION: Predicted propeptide region
<221> NAME/KEY: PEPTIDE
<222> LOCATION: (38)...(94)
<223> OTHER INFORMATION: Mature peptide LBNL 5197/8-1

<400> SEQUENCE: 55

Met Gln Ile Ala Asn Ile Ser Leu Phe Leu Phe Ala Ala Met Gly Thr
 1               5                  10                  15

Ile Ala Ser Pro Leu Asp Ala Glu Ser Asp Asp Leu Ser Ala Arg Asp
             20                  25                  30

Val Asn Ala Ala Asp Ile Gln Tyr Thr Gly Lys Cys Tyr Thr Asn Gly
         35                  40                  45

Asn Asn Cys Lys Tyr Asp Ser Asp Gly Lys Thr His Phe Val Lys Cys
     50                  55                  60
```

Pro Ser Ala Ala Asn Thr Lys Cys Glu Lys Asp Gly Asn Lys Cys Thr
 65                  70                  75                  80

Tyr Asp Ser Tyr Asn Gly Lys Val Lys Cys Asp Phe Arg His
                 85                  90

<210> SEQ ID NO 56
<211> LENGTH: 40
<212> TYPE: DNA
<213> ORGANISM: Artificial Sequence
<220> FEATURE:
<223> OTHER INFORMATION: Primer phn76685

<400> SEQUENCE: 56
aattgcggcc gcatgcagat tgccaatatt tcgcttttcc                            40

<210> SEQ ID NO 57
<211> LENGTH: 40
<212> TYPE: DNA
<213> ORGANISM: Artificial Sequence
<220> FEATURE:
<223> OTHER INFORMATION: Primer phn76686

<400> SEQUENCE: 57
tatatggatc cttaatggcg gaagtcgcac ttgacctttc                            40

<210> SEQ ID NO 58
<211> LENGTH: 401
<212> TYPE: DNA
<213> ORGANISM: Penicillium miczyinskii

<400> SEQUENCE: 58
atgcagattg ccaatatatc gcttttcctt ttcgctgcca tgggtacgat tgctagtccc      60
cttgatgccg agtccgacga cctcagtgct agagacgtga atgctgccga cattcagtac     120
accggagtga gattattaca gcacatgcag acatgagaac gaagctaatt acttgttcca     180
gaaatgttat acaaatggca acaattgtaa gtacgatagt gatgggaaga cgcactttgt     240
caagtgccct agcgccgcca acacaaaggt atctttcctt tataattaag catattgacc     300
tcgactaacc ttgatcatta actttcaagt gcgagaagga cggaaataag tgcacatatg     360
actcctacaa cggaaaggtc aagtgcgact ccgccatta a                          401

<210> SEQ ID NO 59
<211> LENGTH: 60
<212> TYPE: PRT
<213> ORGANISM: Aspergillus giganteus

<400> SEQUENCE: 59

Met Gln Glu Met Arg Ala Arg Val Leu Ala Thr Tyr Asn Gly Lys Cys
 1               5                  10                  15

Tyr Lys Lys Asp Asn Ile Cys Lys Tyr Lys Ala Gln Ser Gly Lys Thr
                 20                  25                  30

Ala Ile Cys Lys Cys Tyr Val Lys Lys Cys Pro Arg Asp Gly Ala Lys
             35                  40                  45

Cys Glu Phe Asp Ser Tyr Lys Gly Lys Cys Tyr Cys
 50                  55                  60

<210> SEQ ID NO 60
<211> LENGTH: 92
<212> TYPE: PRT
<213> ORGANISM: Penicillium chrysogenum

<400> SEQUENCE: 60

```
Met Gln Ile Thr Thr Val Ala Leu Phe Leu Phe Ala Ala Met Gly Gly
1               5                   10                  15

Val Ala Thr Pro Ile Glu Ser Val Ser Asn Asp Leu Asp Ala Arg Ala
            20                  25                  30

Glu Ala Gly Val Leu Ala Lys Tyr Thr Gly Lys Cys Thr Lys Ser Lys
        35                  40                  45

Asn Glu Cys Lys Tyr Lys Asn Asp Ala Gly Lys Asp Thr Phe Ile Lys
    50                  55                  60

Cys Pro Lys Phe Asp Asn Lys Lys Cys Thr Lys Asp Asn Asn Lys Cys
65                  70                  75                  80

Thr Val Asp Thr Tyr Asn Asn Ala Val Asp Cys Asp
                85                  90
```

<210> SEQ ID NO 61
<211> LENGTH: 92
<212> TYPE: PRT
<213> ORGANISM: Aspergillus niger

<400> SEQUENCE: 61

```
Met Gln Leu Thr Ser Ile Ala Ile Ile Leu Phe Ala Ala Met Gly Ala
1               5                   10                  15

Ile Ala Asn Pro Ile Ala Ala Glu Ala Asp Asn Leu Val Ala Arg Glu
            20                  25                  30

Ala Glu Leu Ser Lys Tyr Gly Gly Glu Cys Ser Val Glu His Asn Thr
        35                  40                  45

Cys Thr Tyr Leu Lys Gly Gly Lys Asp His Ile Val Ser Cys Pro Ser
    50                  55                  60

Ala Ala Asn Leu Arg Cys Lys Thr Glu Arg His His Cys Glu Tyr Asp
65                  70                  75                  80

Glu His His Lys Thr Val Asp Cys Gln Thr Pro Val
                85                  90
```

<210> SEQ ID NO 62
<211> LENGTH: 4
<212> TYPE: PRT
<213> ORGANISM: Artificial Sequence
<220> FEATURE:
<223> OTHER INFORMATION: Endoplasmic reticulum retention sequence

<400> SEQUENCE: 62

```
Lys Asp Glu Leu
 1
```

<210> SEQ ID NO 63
<211> LENGTH: 6
<212> TYPE: PRT
<213> ORGANISM: Artificial Sequence
<220> FEATURE:
<223> OTHER INFORMATION: Endoplasmic reticulum retention sequence

<400> SEQUENCE: 63

```
Ser Glu Lys Asp Glu Leu
 1               5
```

<210> SEQ ID NO 64
<211> LENGTH: 4
<212> TYPE: PRT
<213> ORGANISM: Artificial Sequence
<220> FEATURE:
<223> OTHER INFORMATION: Endoplasmic reticulum retention sequence

<400> SEQUENCE: 64

His Asp Glu Leu
1

<210> SEQ ID NO 65
<211> LENGTH: 4
<212> TYPE: PRT
<213> ORGANISM: Artificial Sequence
<220> FEATURE:
<223> OTHER INFORMATION: Endoplasmic reticulum retention sequence

<400> SEQUENCE: 65

His Asp Glu Phe
1

<210> SEQ ID NO 66
<211> LENGTH: 1031
<212> TYPE: DNA
<213> ORGANISM: Monascus ruber
<220> FEATURE:
<221> NAME/KEY: intron
<222> LOCATION: (351)...(410)
<221> NAME/KEY: intron
<222> LOCATION: (501)...(560)
<221> NAME/KEY: TATA_signal
<222> LOCATION: (178)...(181)
<221> NAME/KEY: CAAT_signal
<222> LOCATION: (218)...(221)
<221> NAME/KEY: CAAT_signal
<222> LOCATION: (255)...(258)

<400> SEQUENCE: 66

| | | | | | |
|---|---|---|---|---|---|
| actatagggc | acgcgtggtc | gacggcccgg | gctggtcgta | tgaacgaact | tttggatata | 60 |
| tgaggcatat | cttttattgg | atagcttgga | taatctttcg | accgcggcct | cgatcatggc | 120 |
| tatatcgaat | gtgaggatgg | tatttgtcaa | atatcgcagg | aaatattcgt | cattgtctat | 180 |
| ataagacacc | ttcacggcgc | tccagtttgt | gaagtatcaa | tctcatcaac | ctttctctct | 240 |
| caactactat | accgcaatcc | tctacaagac | cactcttcca | ccatgcatat | tactagcatt | 300 |
| gccattgtct | tcttcgccgc | aatgggcgcg | gttgctagcc | ccatcgcaac | cgagtcggac | 360 |
| gatcttgatg | cccgagacgt | acagcttagt | aaattcggag | gagtaagttc | ttcttataag | 420 |
| atgtctatat | agaaatagca | ctaaccttc | tgaaccgctt | tacaggaatg | cagcttgaaa | 480 |
| cacaacacgt | gcacatacct | aaagggtgga | agaaccatg  | tagtcaattg | cggttcggcc | 540 |
| gccaacaaga | aggtagattc | cgattcgatt | cggggccaat | tgatttgttc | ttatcattta | 600 |
| atcttcatct | acagtgcaag | tctgatcgcc | accactgtga | atacgatgag | caccacaaga | 660 |
| gggttgactg | ccagacccca | gtttgaacca | attatacagt | tccgcaagaa | acagagtcct | 720 |
| tggctgtttt | gattattctc | tagcccatca | taggtctgaa | atggttcgtg | tctctcaatg | 780 |
| ccaatgatca | tacgccaagg | agggcttgga | acaagcagtg | gattctgtct | gtattgggt  | 840 |
| gaggtattcg | tacagttctc | gttatcacca | cactcgttcg | gtatctagct | agctctactt | 900 |
| ctatgaaagt | gttgcctatt | gactgcctat | tctattgagt | aatattacta | gtagcagtag | 960 |
| aatttctgac | agttttcgag | attgttggcc | agaccagccc | gggccgtcga | ccacgcgtgc | 1020 |
| cctatagtcc | t | | | | | 1031 |

<210> SEQ ID NO 67
<211> LENGTH: 92
<212> TYPE: PRT
<213> ORGANISM: Artificial Sequence
<220> FEATURE:
<223> OTHER INFORMATION: Deduced full-length amino acid sequence encoded
      by the nucleotide sequence of SEQ ID NO:66
<221> NAME/KEY: SIGNAL

```
<222> LOCATION: (1)...(18)
<223> OTHER INFORMATION: Predicted signal peptide
<221> NAME/KEY: PROPEP
<222> LOCATION: (19)...(31)
<223> OTHER INFORMATION: Predicted propeptide region
<221> NAME/KEY: PEPTIDE
<222> LOCATION: (32)...(92)
<223> OTHER INFORMATION: Mature peptide LBNL 9827-2
<221> NAME/KEY: PEPTIDE
<222> LOCATION: (35)...(92)
<223> OTHER INFORMATION: Mature peptide LBNL 9827-1

<400> SEQUENCE: 67

Met His Ile Thr Ser Ile Ala Ile Val Phe Phe Ala Ala Met Gly Ala
 1               5                  10                  15

Val Ala Ser Pro Ile Ala Thr Glu Ser Asp Asp Leu Asp Ala Arg Asp
            20                  25                  30

Val Gln Leu Ser Lys Phe Gly Gly Glu Cys Ser Leu Lys His Asn Thr
        35                  40                  45

Cys Thr Tyr Leu Lys Gly Gly Lys Asn His Val Asn Cys Gly Ser
50                  55                  60

Ala Ala Asn Lys Lys Cys Lys Ser Asp Arg His His Cys Glu Tyr Asp
65                  70                  75                  80

Glu His His Lys Arg Val Asp Cys Gln Thr Pro Val
                85                  90

<210> SEQ ID NO 68
<211> LENGTH: 50
<212> TYPE: PRT
<213> ORGANISM: Artificial Sequence
<220> FEATURE:
<223> OTHER INFORMATION: Consensus sequence deduced from an alignment of
      antifungal polypeptides
<221> NAME/KEY: VARIANT
<222> LOCATION: 2, 4, 5, 6, 7, 9, 11, 13, 14, 15, 16, 17, 18, 19, 20,
      23, 25, 26, 27, 30, 31, 33, 34, 36, 37, 38, 40, 41, 43, 44, 45,
      46, 47, 49
<223> OTHER INFORMATION: Xaa = any amino acid
<221> NAME/KEY: VARIANT
<222> LOCATION: 21
<223> OTHER INFORMATION: Xaa = any amino acid or no amino acid

<400> SEQUENCE: 68

Gly Xaa Cys Xaa Xaa Xaa Xaa Asn Xaa Cys Xaa Tyr Xaa Xaa Xaa Xaa
 1               5                  10                  15

Xaa Xaa Xaa Xaa Xaa Val Xaa Cys Xaa Xaa Xaa Ala Asn Xaa Xaa Cys
            20                  25                  30

Xaa Xaa Asp Xaa Xaa Xaa Cys Xaa Xaa Asp Xaa Xaa Xaa Xaa Xaa Val
        35                  40                  45

Xaa Cys
    50

<210> SEQ ID NO 69
<211> LENGTH: 278
<212> TYPE: DNA
<213> ORGANISM: Artificial Sequence
<220> FEATURE:
<223> OTHER INFORMATION: Prepro-LBNL-5220 construct
<221> NAME/KEY: misc_feature
<222> LOCATION: (1)...(57)
<223> OTHER INFORMATION: Nucleotide sequence encoding the prepropeptide
      region of LBNL-5197/8-1
<221> NAME/KEY: misc_feature
<222> LOCATION: (58)...(114)
<223> OTHER INFORMATION: Nucleotide sequence encoding the propeptide
      region of LBNL-5197/8-1
<221> NAME/KEY: mat_peptide
<222> LOCATION: (115)...(278)
```

```
<223> OTHER INFORMATION: Nucleotide sequence encoding the mature
      LBNL-5220 peptide

<400> SEQUENCE: 69
atggtgcaga ttgccaatat cagcctgttc ctgtttgctg caatggggac catcgcgtcc      60
cctctggatg cggaaagtga cgatctgtcc gcccgcgacg ttaacgccgc cgatctcaag     120
tacaccggca cctgcacccg cgctaacaac cagtgcaagt acaagggtca gaacgatcgc     180
gataccttcg tgaagtgccc aaccttcgcc aacaagaagt gcacgcgcga tgggctcctt     240
gctccttcga ctcatacagc cgcgccgtca cctgcgac                              278

<210> SEQ ID NO 70
<211> LENGTH: 294
<212> TYPE: DNA
<213> ORGANISM: Artificial Sequence
<220> FEATURE:
<223> OTHER INFORMATION: BAA-Pro-LBNL-5220 construct
<221> NAME/KEY: sig_peptide
<222> LOCATION: (1)...(72)
<223> OTHER INFORMATION: Nucleotide sequence encoding the barley-alpha
      amylase signal peptide
<221> NAME/KEY: misc_feature
<222> LOCATION: (73)...(129)
<223> OTHER INFORMATION: Nucleotide sequence encoding the propeptide
      region of LBNL-5197/8-1
<221> NAME/KEY: mat_peptide
<222> LOCATION: (130)...(294)
<223> OTHER INFORMATION: Nucleotide sequence encoding the mature
      LBNL-5220 peptide

<400> SEQUENCE: 70
atggggaaca aacatttgtc cctctccctc ttcctcgtcc tccttgggct gtcggccagc      60
ttggcctccg gatcccctct ggatgcggaa agtgacgatc tgtccgcccg cgacgttaac     120
gccgccgatc tcaagtacac cggcacctgc acccgcgcta acaaccagtg caagtacaag     180
ggtcagaacg atcgcgatac cttcgtgaag tgcccaacct tcgccaacaa gaagtgcacg     240
cgcgatggcg ctccttgctc cttcgactca tacagccgcg ccgtcacctg cgac           294

<210> SEQ ID NO 71
<211> LENGTH: 573
<212> TYPE: DNA
<213> ORGANISM: Mirabilis mosaic caulimovirus
<220> FEATURE:
<221> NAME/KEY: promoter
<222> LOCATION: (1)...(573)
<223> OTHER INFORMATION: Mirabilis caulimovirus promoter sequence

<400> SEQUENCE: 71
ccaattcgtc aacttcgtcc acagacatca acatcttatc gtcctttgaa gataagataa      60
taatgttgaa gataagagtg ggagccccca ctaaacatt gctttgtcaa agctaaaaa      120 agatgatgcc cgacagccac ttgtgtgaag catgagaagc cggtccctcc actaagaaaa     180
ttagtgaagc atcttccagt ggtccctcca ctcacagctc aatcagtgag caacaggacg     240
aaggaaatga cgtaagccat gacgtctaat cccaacttcg tccacagaca tcaacatctt     300
atcgtccttt gaagataaga taataatgtt gaagataaga gtgggagcca ccactaaaac     360
attgctttgt caaagctaaa aagatgat gcccgacagc cacttgtgtg aagcatgaga     420
agccggtccc tccactaaga aaattagtga agcatcttcc agtggtccct ccactcacag     480
ctcaatcagt gagcaacagg acgaaggaaa tgacgtaagc catgacgtct aatcccacaa     540
gaatttcctt atataaggaa cacaaatcag aag                                   573
```

```
<210> SEQ ID NO 72
<211> LENGTH: 85
<212> TYPE: DNA
<213> ORGANISM: Artificial Sequence
<220> FEATURE:
<223> OTHER INFORMATION: Consensus sequence derived from an alignment of
      dicot 5' untranslated regions
<221> NAME/KEY: 5'UTR
<222> LOCATION: (1)...(85)
<223> OTHER INFORMATION: A-rich leader sequence

<400> SEQUENCE: 72
gaagagatca atcgaaatca aaatcggaat cgaaatcaaa atcggaatcg aaatctctca    60
tctaagagct caaaaaaaaa aaaaa                                          85

<210> SEQ ID NO 73
<211> LENGTH: 11788
<212> TYPE: DNA
<213> ORGANISM: Artificial Sequence
<220> FEATURE:
<223> OTHER INFORMATION: Vector containing the Pre-pro-LBNL-5220
      construct

<400> SEQUENCE: 73
atccggcaaa caaaccaccg ctggtagcgg tggttttttt gtttgcaagc agcagattac    60
gcgcagaaaa aaaggatctc aagaagatcc tttgatcttt tctacggggt ctgacgctca   120
gtggaacgaa aactcacgtt aagggatttt ggtcatgaga ttatcaaaaa ggatcttcac   180
ctagatcctt ttaaattaaa aatgaagcgt acgttggaat cgcttctaca aaactcacag   240
aaacaatcaa acaaacatac acagcgattt attcacacga acccgaatta caacggtata   300
tatcctgtca gccaacacca aaacatcaaa aaaatcggga tcaggatcag gatctgcggc   360
cgcatcctgc aggtcgactc tagaggatcc cccaattcgt caacttcgtc cacagacatc   420
aacatcttat cgtcctttga agataagata ataatgttga agataagagt gggagccccc   480
actaaaacat tgctttgtca aaagctaaaa aagatgatgc ccgacagcca cttgtgtgaa   540
gcatgagaag ccggtccctc cactaagaaa attagtgaag catcttccag tggtccctcc   600
actcacagct caatcagtga gcaacaggac gaaggaaatg acgtaagcca tgacgtctaa   660
tcccaacttc gtccacagac atcaacatct tatcgtcctt tgaagataag ataataatgt   720
tgaagataag agtgggagcc accactaaaa cattgctttg tcaaaagcta aaaagatga   780 tgcccgacag ccacttgtgt gaagcatgag aagccggtcc ctccactaag aaaattagtg   840
aagcatcttc cagtggtccc tccactcaca gctcaatcag tgagcaacag gacgaaggaa   900
atgacgtaag ccatgacgtc taatcccaca agaatttcct tatataagga acacaaatca   960
gaaggaagag atcaatcgaa atcaaaatcg gaatcgaaat caaaatcgga atcgaaatct  1020
ctcatctaag agctcaaaaa aaaaaaaaac catggtgcag attgccaata tcagcctgtt  1080
cctgtttgct gcaatgggga ccatcgcgtc ccctctggat gcggaaagtg acgatctgtc  1140
cgcccgcgac gttaacgccg ccgatctcaa gtacaccggc acctgcaccc gcgctaacaa  1200
ccagtgcaag tacaagggtc agaacgatcg cgataccttc gtgaagtgcc caaccttcgc  1260
caacaagaag tgcacgcgcg atggcgctcc ttgctccttc gactcataca gccgcgccgt  1320
cacctgcgac tgaggcgcgc ctaggttttt gtgatctgat gataagtggt tggttcgtgt  1380
ctcatgcact tgggaggtga tctatttcac ctggtgtagt ttgtgtttcc gtcagttgga  1440
aaaacttatc cctatcgatt tcgttttcat tttctgcttt tcttttatgt accttcgttt  1500
gggcttgtaa cgggcctttg tatttcaact ctcaataata atccaagtgc atgttaaaca  1560
```

```
atttgtcatc tgtttcggct ttgatatact actggtgaag atgggccgta ctactgcatc    1620
acaacgaaaa ataataataa gatgaaaaac ttgaagtgga aaaaaaaaaa aacttgaatg    1680
ttcactacta ctcattgacc ataatgttta acatacatag ctcaatagta tttttgtgaa    1740
tatggcaaca caaacagtcc aaaacaattg tctcttacta taccaaacca agggcgccgc    1800
ttgtttgcca ctctttgtgt gcaatagtgt gattaccaca tctccacatt caatatattc    1860
cctgaattat ctgacgattt tgatggctca ctgttttccc aagtcttgaa ttgtcttctg    1920
tgcgccagtc aaatgcatat gtgttgagtt tatcttttaa atatcaagct tttgttttta    1980
acttttgttt gtaaccaaaa actcacagta ggagtttgat cacataattt tatgtttgcc    2040
tttgcaattt ctagtgagtc tttgattaaa agcttgaaaa gaaaatgcag ccaagcttac    2100
caagtaagtt atgtgtatta accagaggaa gagagaatct tgcaaaattt caacaaacac    2160
aaaaagaagt attactacga ttggtggaga agaaaacga ttccaaatct tgaactgttg    2220
ttgtaaaagc atagcagaaa gtgggagaca accgaaatag aaatgactat aacttaattt    2280
aatgttatca ttataatttc ttctagcaaa tatttagaaa gtaaatatca catcaacctt    2340
taatgtaatt aagctttctc ttttttgattc atgtgagatg aaaagaaaaa aaagaagaga    2400
aaagtgtaga aaacacatca tttctaagct gaaggtacat agtacccttg tacttttggt    2460
ttcacctgca tagagaaaac ccacaagaat atgacagtct gatttgtcag tctcattctc    2520
aagcaacatt tctctatccg ttactttcat ggtgaataac acaatccatc atcaatactt    2580
tgtgttactc agaaactgaa agttattccg agtcttgcat atctttggac ctactcgttt    2640
ttctaccatt attgctgatt gttaagctct cgctacttga atcggcattg ttggagtggg    2700
aaggttcaaa aaattggagt tatgactagt tgtctctttc tatgtacgat ggagaaaatg    2760
aataaacaac tgagaaaatg gctcttgttt agttgatgat gctcttaagc tttccactgg    2820
ttgccatata tgatttgggc atttcacttt gatcttaatg ggccttgtaa agcccaagac    2880
tcatgattat ctttagttga tgctcttaat taggtgtggg caaataattc aaactgtatg    2940
tacccgacca aaaccaaagc aaaaataatc gaaccaaacc gaaaatttaa aaataaccga    3000
atgaaaacta atcctataa ctgaaagaac tgaaaccgaa tcaaaatatt taatgtaacc    3060
aaaaatatcc gaaatataat tatattgtca aaaatattaa taatttctag attaaataat    3120
taaaaatact taaaaattta tataaaatag taaaaatact cgaaaataac cacaaatatt    3180
caaaaacaac cgaaatatcc caaaatattc aaagcaaaat aaccgaatgg ataccaaatt    3240
ttaaaaccga aaaaactgga acaaaaccaa aatcgaacca aaatttcaaa aatcgaataa    3300
atactaaact ttagaacaaa aaaaaacgat aaccgaatgt atacgaacca agccgaatt    3360 agataaccga acgtccagga ctactcttaa tctttccgcc acttatgatt tgggctatta    3420
ctttgtttat aatgagcctt tcaagctca agttcatgat tgtccgtgag atgagaaact    3480
gacttgttgg attcgaaacc ctagctagta ttggttaata cttaatacat aaatgacctg    3540
cattgacatc atcatccaag aaaataaaaa ttgtatgctt gagatattta gttttcctag    3600
ctaggttttc tttattttag taccgaatct ttaggtgtgc cacgttaatt tagacccatt    3660
ttttcatact taccaactga gtctagttta atcatgacta taatcgtata aaatgattca    3720
gtcgacgtca ttgcgaacgt atataaaatc atccaaattg acgtcattcc aaagaggtaa    3780
gcatgcttat ctaagagtcc gagcatacta aacaagacga catttatttt gcactccaaa    3840
tcaaattttg tattgcctaa agaaaaacaa tcaaactcaa gtttcttaaa attaatttca    3900
ttcaaactaa tcactttcaa tatctcacat attattcatg ccatttctat ttgtctaaac    3960
```

```
atgatttaaa aaaaaaagta aaatacaaag attactatgc aaaaactcta taaaaaaaaa    4020
ttcaaatttc ttatttattt gtgacatcaa attttcaaaa taattttttt aattatcggt    4080
tgatccggtc agtcgataaa aacataaact ttcagcgacc gttaaaactt tcctactacc    4140
gatttagaga aaatcttagc ttgaaacgta attgtaacct gccttcatgc aagtcgcaag    4200
atatgtcatc ctaagttgta tatgttttct caaagatgt  atttacttga gaaaatacgt    4260
ttcaacgttg atggacaacc aattaagaat caagcacctt tcgtaatcaa tttaggctta    4320
tcgtctaagg tatactgatt tacgacagtt gactagactt ataaggaaca aataatagaa    4380
ataatttcgt caagaaaaat tgattttgga ctcatacttt acataatatt ttactcttaa    4440
atttatttaa gtggctcctc gcatgatccc aaagagcaag cctagactat atggaaaagt    4500
ttctaaacac ttcacctaat catagagact aagatggtaa ttcgtaaacg acaaagccta    4560
gtgacactgt ccattgtaaa attccacatc atattagtat taaacatata catgtagttt    4620
cctgaacaca tgtagtatca aacacacttc gtggcttctt cctcgaaacc tggtaccgcc    4680
tgcaggggcc tatcaggccg gatcgaattc atttacaatt gaatatatcc tgccattta    4740 cacctcgata tatcctgcca caaattccat gtacacagta cattaaaaac gtccgcaatg    4800
tgttattaag ttgtctaagc gtcaatttgt ttacaccaca atatatcctg ccaccagcca    4860
gccaacagct ccccgaccgg cagctcggca caaaatcacc actcgataca ggcagcccat    4920
cagtccacta gagggccctg tatgttattg tattgatctt tcatgatgtt gaagtgtgcc    4980
ataatatgat gatgtataat taaaatatta actgtcgcat ttattgaaat ggcactgtta    5040
tttcaaccat atctttgatt ctgttacaat gacaacgact gaaaaaagta aataatagac    5100
gccgttgtta aagaattgct atcatatgtg ccaaactaga gggaaattta cgtcaattgt    5160
gaaatagtcg cccttatttt gacgtctcac ctaatcaaat attacaaaag atcgatctca    5220
ctctgtcgcc agcaatggtg taatcagcgc agacaagtgg cagtaaagtg cggaaaaacg    5280
tccccgagtg gcatgaatag ctgcctctgt attgctgatt tagtcagcct tatttgactt    5340
aagggtgccc tcgttagtga caaattgctt tcaaggagac agccatgccc cacactttgt    5400
tgaaaaacaa attgcccttt ggggagacgg taaagccagt tgctcttcaa taaggaatct    5460
cgaggaggca atataaccgc ctctggtagt acacttctct aatccaaaaa gtcaatttgt    5520
attcaagata ccgcaaaaaa cttatggatc tgcgtcaat  tttcggtcca acttgcacag    5580
gaaagacgtc gaccgcggta gctcttgccc agcagactgg gcttccagtc ctttcgctcg    5640
atcgggtcca atgttgtcct cagaacgcag ccgcttacga cggattcgaa ggtcatccat    5700
tcggaatgta ttagtttgca ccagctccgc gtcacacctg tcttcatttg aataagatgt    5760
tcgcaattgt ttttagcttt gtcttgttgt ggcagggcgg caagtgcttc agacatcatt    5820
ctgttttcaa attttatgct ggagaacagc ttcttaattc ctttggaaat aatagactgc    5880
gtcttaaaat tacgatgcgg cggctcggat agtaccgagg aaaggcagct ttgccaagcc    5940
gcatagcaat ctgctcacgt tgggaacaga ttgctaaagg cgaaatgcac ctctacctca    6000
ggccgccatc acaccccgt  acgaaacatc cacgtcagcg tcaaagaaat agccagcacc    6060
tcttgcagtc ttgattaact gaggggtcgt cgggtccccc tcaagcttcc ggcgcagccg    6120
caaaatgagg acatcaatac ttctgtcata cacctcctcc tcgcgtaccc gactggcgat    6180
cagaagctgc tcccgggata ggacgtcgcg cggcttctcc aggaaagcaa ccaggagatt    6240
aaactcacct gccgtgagtt tcacctcact gccctcttcc gaaatcaagc ggcgtcgcct    6300
gagattaagt gtccagtcag cgaaactaaa tgagcgtcga tctttggttc gcgcgacact    6360
```

```
gggccgcacg cgtaacgcaa cacggatgcg cgccagaaat tcccgcgtcc caaaaggctt    6420
ggcaataaaa tcggttgctc ccaactcgag cgcaataact ttgtccgcct cttcgaggcg    6480
agcgccgcta ataattatga ttggaacatc ggacttcgtg gccagactac gaacaatttc    6540
aagcccatct tcgcgaccca aattaagatc gacgaccacg acatcgaccg tctcggagca    6600
gagtacacga ttgaactgct tgctgtcggc taccgcagtc accttaaagg catggatcgt    6660
aagatactcg actataagat gccgcatagc gacatcgtca tcgatgacaa gaacgtgttt    6720
caacggttca cctctcaatc taggctcctg gccagccatt tgcagctcaa cagaatttat    6780
acacgtaaag gttgtatttg ctagactcca ctctttaatt ttctctcact acacgggcat    6840
ttcggcaaga tttcgaccaa accgcgcacg acagaaatgc aaactagatg tctccgtttg    6900
atgacaaaga ttgctgagca ttgctacaaa cgtaattcta caacgcgcca tgcggcattt    6960
agaaacatgg atcacaacta ctgctggtta agaagatcgc ctattgtctc accgcgccga    7020
cgcgcatcgg cagcgagcca gatttcgccc acctcgtaaa tgtcaccgtg ggcacggaag    7080
ggtacgatga catcaactgc ggttgcgagc atgtcaatca gggtgcgatc ttccaagcta    7140 gcccctgag cgctgctttt cacgagcgaa tgcagcgagg aagtgacgcc caccgaggcc    7200
aggcggcgcg gtgccttccg tgaggacgca ttgaccgagg ccgacgccct ggcggccgcc    7260
gagaatgaac gccaagagga acaagcatga aaccgcacca ggacggccag gacgaaccgt    7320
ttttcattac cgaagagatc gaggcggaga tgatcgcggc cgggtacgtg ttcgagccgc    7380
ccgcgcacgt ctcaaccgtg cggctgcatg aaatcctggc cggtttgtct gatgccaagc    7440
tggcggcctg gccggccagc ttggccgctg aagaaaccga gcgccgccgt ctaaaaaggt    7500
gatgtgtatt tgagtaaaac agcttgcgtc atgcggtcgc tgcgtatatg atgcgatgag    7560
taaataaaca aatacgcaag gggaacgcat gaaggttatc gctgtactta accagaaagg    7620
cgggtcaggc aagacgacca tcgcaaccca tctagcccgc gccctgcaac tcgccggggc    7680
cgatgttctg ttagtcgatt ccgatcccca gggcagtgcc cgcgattggg cggccgtgcg    7740
ggaagatcaa ccgctaaccg ttgtcggcat cgaccgcccg acgattgacc gcgacgtgaa    7800
ggccatcggc cggcgcgact tcgtagtgat cgacggagcg ccccaggcgg cggacttggc    7860
tgtgtccgcg atcaaggcag ccgacttcgt gctgattccg gtgcagccaa gcccttacga    7920
catatgggcc accgccgacc tggtggagct ggttaagcag cgcattgagg tcacggatgg    7980
aaggctacaa gcggccttttg tcgtgtcgcg ggcgatcaaa ggcacgcgca tcggcggtga    8040
ggttgccgag gcgctggccg ggtacgagct gcccattctt gagtcccgta tcacgcagcg    8100
cgtgagctac ccaggcactg ccgccgccgg cacaaccgtt cttgaatcag aacccgaggg    8160
cgacgctgcc cgcgaggtcc aggcgctggc cgctgaaatt aaatcaaaac tcatttgagt    8220
taatgaggta aagagaaaat gagcaaaagc acaaacacgc taagtgccgg ccgtccgagc    8280
gcacgcagca gcaaggctgc aacgttggcc agcctggcag acacgccagc catgaagcgg    8340
gtcaactttc agttgccggc ggaggatcac accaagctga agatgtacgc ggtacgccaa    8400
ggcaagacca ttaccgagct gctatctgaa tacatcgcgc agctaccaga gtaaatgagc    8460
aaatgaataa atgagtagat gaattttagc ggctaaagga ggcggcatgg aaaatcaaga    8520
acaaccaggc accgacgccg tggaatgccc catgtgtgga ggaacgggcg gttggccagg    8580
cgtaagcggc tgggttgtct gccggccctg caatggcact ggaaccccca agcccgagga    8640
atcggcgtga cggtcgcaaa ccatccggcc cggtacaaat cggcgcggcg ctgggtgatg    8700
acctggtgga gaagttgaag gccgcgcagg ccgcccagcg gcaacgcatc gaggcagaag    8760
```

```
cacgccccgg tgaatcgtgg caagcggccg ctgatcgaat ccgcaaagaa tcccggcaac   8820
cgccggcagc cggtgcgccg tcgattagga agccgcccaa gggcgacgag caaccagatt   8880
ttttcgttcc gatgctctat gacgtgggca cccgcgatag tcgcagcatc atggacgtgg   8940
ccgtttccg tctgtcgaag cgtgaccgac gagctggcga ggtgatccgc tacgagcttc    9000
cagacgggca cgtagaggtt tccgcagggc cggccggcat ggccagtgtg tgggattacg   9060
acctggtact gatggcggtt tcccatctaa ccgaatccat gaaccgatac cgggaaggga   9120
agggagacaa gcccggccgc gtgttccgtc cacacgttgc ggacgtactc aagttctgcc   9180
ggcgagccga tggcggaaag cagaaagacg acctggtaga aacctgcatt cggttaaaca   9240
ccacgcacgt tgccatgcag cgtacgaaga aggccaagaa cggccgcctg gtgacggtat   9300
ccgagggtga agccttgatt agccgctaca agatcgtaaa gagcgaaacc gggcggccgg   9360
agtacatcga gatcgagcta gctgattgga tgtaccgcga gatcacagaa ggcaagaacc   9420
cggacgtgct gacggttcac cccgattact ttttgatcga tcccggcatc ggccgttttc   9480
tctaccgcct ggcacgccgc gccgcaggca aggcagaagc cagatggttg ttcaagacga   9540
tctacgaacg cagtggcagc gccggagagt tcaagaagtt ctgtttcacc gtgcgcaagc   9600
tgatcgggtc aaatgacctg ccggagtacg atttgaagga ggaggcgggg caggctggcc   9660
cgatcctagt catgcgctac cgcaacctga tcgagggcga agcatccgcc ggttcctaat   9720
gtacggagca gatgctaggg caaattgccc tagcagggga aaaggtcga aaaggtctct    9780
ttcctgtgga tagcacgtac attgggaacc caaagccgta cattgggaac cggaacccgt   9840
acattgggaa cccaaagccg tacattggga accggtcaca catgtaagtg actgatataa   9900
aagagaaaaa aggcgatttt tccgcctaaa actctttaaa acttattaaa actcttaaaa   9960
cccgcctggc ctgtgcataa ctgtctggcc agcgcacagc cgaagagctg caaaaagcgc  10020
ctacccttcg gtcgctgcgc tccctacgcc ccgccgcttc gcgtcggcct atcgcggccg  10080
ctgcatataa ttgtggtttc aaaatcggct ccgtcgatac tatgttatac gccaactttg  10140
aaaacaactt tgaaaagct gttttctggt atttaaggtt ttagaatgca aggaacagtg    10200
aattggagtt cgtcttgtta taattagctt cttggggtat ctttaaatac tgtagaaaag  10260
aggaaggaaa taataaatgg ctaaaatgag aatatcaccg gaattgaaaa aactgatcga  10320
aaaataccgc tgcgtaaaag atacggaagg aatgtctcct gctaaggtat ataagctggt  10380
gggagaaaat gaaaacctat atttaaaaat gacggacagc cggtataaag ggaccaccta  10440
tgatgtggaa cgggaaaagg acatgatgct atggctggaa ggaaagctgc ctgttccaaa  10500
ggtcctgcac tttgaacggc atgatggctg gagcaatctg ctcatgagtg aggccgatgg  10560
cgtcctttgc tcgaagagt atgaagatga acaaagccct gaaaagatta tcgagctgta   10620
tgcggagtgc atcaggctct ttcactccat cgacatatcg gattgtccct atacgaatag  10680
cttagacagc cgcttagccg aattggatta cttactgaat aacgatctgg ccgatgtgga  10740
ttgcgaaaac tgggaagaag acactccatt taaagatccg cgcgagctgt atgatttttt  10800
aaagacggaa aagcccgaag aggaacttgt cttttcccac ggcgacctgg agacagcaa   10860
catctttgtg aaagatggca agtaagtgg ctttattgat cttgggagaa gcggcagggc   10920
ggacaagtgg tatgacattg ccttctgcgt ccggtcgatc agggaggata tcggggaaga  10980
acagtatgtc gagctatttt ttgacttact ggggatcaag cctgattggg agaaaataaa  11040
atattatatt ttactggatg aattgtttta gtacctagat acgtaaccaa ctagtgcgct  11100
cttccgcttc ctcgctcact gactcgctgc gctcggtcgt tcggctgcgg cgagcggtat  11160
```

-continued

| | |
|---|---|
| cagctcactc aaaggcggta atacggttat ccacagaatc aggggataac gcaggaaaga | 11220 |
| acatgtgagc aaaaggccag caaaaggcca ggaaccgtaa aaaggccgcg ttgctggcgt | 11280 |
| ttttccatag gctccgcccc cctgacgagc atcacaaaaa tcgacgctca agtcagaggt | 11340 |
| ggcgaaaccc gacaggacta taaagatacc aggcgtttcc ccctggaagc tccctcgtgc | 11400 |
| gctctcctgt tccgaccctg ccgcttaccg gatacctgtc cgcctttctc ccttcgggaa | 11460 |
| gcgtggcgct ttctcatagc tcacgctgta ggtatctcag ttcggtgtag gtcgttcgct | 11520 |
| ccaagctggg ctgtgtgcac gaaccccccg ttcagcccga ccgctgcgcc ttatccggta | 11580 |
| actatcgtct tgagtccaac ccggtaagac acgacttatc gccactggca gcagccactg | 11640 |
| gtaacaggat tagcagagcg aggtatgtag gcggtgctac agagttcttg aagtggtggc | 11700 |
| ctaactacgg ctacactaga aggacagtat ttggtatctg cgctctgctg aagccagtta | 11760 |
| ccttcggaaa aagagttggt agctcttg | 11788 |

<210> SEQ ID NO 74
<211> LENGTH: 11803
<212> TYPE: DNA
<213> ORGANISM: Artificial Sequence
<220> FEATURE:
<223> OTHER INFORMATION: Vector containing the BAA-pro-LBNL-5220
 construct

<400> SEQUENCE: 74

| | |
|---|---|
| atccggcaaa caaaccaccg ctggtagcgg tggttttttt gtttgcaagc agcagattac | 60 |
| gcgcagaaaa aaggatctca agaagatcc tttgatcttt tctacggggt ctgacgctca | 120 |
| gtggaacgaa aactcacgtt aagggatttt ggtcatgaga ttatcaaaaa ggatcttcac | 180 |
| ctagatcctt ttaaattaaa aatgaagcgt acgttggaat cgcttctaca aaactcacag | 240 |
| aaacaatcaa acaaacatac acagcgattt attcacacga acccgaatta caacggtata | 300 |
| tatcctgtca gccaacacca aaacatcaaa aaaatcggga tcaggatcag gatctgcggc | 360 |
| cgcatcctgc aggtcgactc tagaggatcc cccaattcgt caacttcgtc cacagacatc | 420 |
| aacatcttat cgtcctttga agataagata taatgttga agataagagt gggagccccc | 480 |
| actaaaacat tgctttgtca aaagctaaaa aagatgatgc ccgacagcca cttgtgtgaa | 540 |
| gcatgagaag ccggtccctc cactaagaaa attagtgaag catcttccag tggtccctcc | 600 |
| actcacagct caatcagtga gcaacaggac gaaggaaatg acgtaagcca tgacgtctaa | 660 |
| tcccaacttc gtccacagac atcaacatct tatcgtcctt tgaagataag ataataatgt | 720 |
| tgaagataag agtgggagcc accactaaaa cattgctttg tcaaaagcta aaaagatga | 780 |
| tgcccgacag ccacttgtgt gaagcatgag aagccggtcc ctccactaag aaaattagtg | 840 |
| aagcatcttc cagtggtccc tccactcaca gctcaatcag tgagcaacag gacgaaggaa | 900 |
| atgacgtaag ccatgacgtc taatcccaca agaatttcct tatataagga acacaaatca | 960 |
| gaaggaagag atcaatcgaa atcaaaatcg gaatcgaaat caaaatcgga atcgaaatct | 1020 |
| ctcatctaag agctcaaaaa aaaaaaaaac catggggaac aaacatttgt ccctctccct | 1080 |
| cttcctcgtc ctccttgggc tgtcggccag cttggcctcc ggatccctc tggatgcgga | 1140 |
| aagtgacgat ctgtccgccc gcgacgttaa cgccgccgat ctcaagtaca ccggcacctg | 1200 |
| cacccgcgct aacaaccagt gcaagtacaa gggtcagaac gatcgcgata ccttcgtgaa | 1260 |
| gtgcccaacc ttcgccaaca agaagtgcac gcgcgatggc gctccttgct ccttcgactc | 1320 |
| atacagccgc gccgtcacct gcgactgagg gcgcgcctagg tttttgtgat ctgatgataa | 1380 |
| gtggttggtt cgtgtctcat gcacttggga ggtgatctat ttcacctggt gtagtttgtg | 1440 |

```
tttccgtcag ttggaaaaac ttatccctat cgatttcgtt ttcattttct gcttttcttt    1500
tatgtacctt cgtttgggct tgtaacgggc ctttgtattt caactctcaa taataatcca    1560
agtgcatgtt aaacaatttg tcatctgttt cggctttgat atactactgg tgaagatggg    1620
ccgtactact gcatcacaac gaaaaataat aataagatga aaaacttgaa gtggaaaaaa    1680
aaaaaaactt gaatgttcac tactactcat tgaccataat gtttaacata catagctcaa    1740 tagtatttt gtgaatatgg caacacaaac agtccaaaac aattgtctct tactatacca    1800
aaccaagggc gccgcttgtt tgccactctt tgtgtgcaat agtgtgatta ccacatctcc    1860
acattcaata tattccctga attatctgac gattttgatg gctcactgtt ttcccaagtc    1920
ttgaattgtc ttctgtgcgc cagtcaaatg catatgtgtt gagtttatct tttaaatatc    1980
aagcttttgt ttttaacttt tgtttgtaac caaaaactca cagtaggagt ttgatcacat    2040
aattttatgt ttgcctttgc aatttctagt gagtctttga ttaaaagctt gaaaagaaaa    2100
tgcagccaag cttaccaagt aagttatgtg tattaaccag aggaagagag aatcttgcaa    2160
aatttcaaca acacaaaaa gaagtattac tacgattggt ggagaaagaa acgattcca     2220 aatcttgaac tgttgttgta aaagcatagc agaaagtggg agacaaccga atagaaatg     2280 actataactt aatttaatgt tatcattata atttcttcta gcaaatattt agaaagtaaa    2340
tatcacatca acctttaatg taattaagct ttctcttttt gattcatgtg agatgaaaag    2400 aaaaaaaga agagaaaagt gtagaaaaca catcatttct aagctgaagg tacatagtac    2460
ccttgtactt tggtttcac ctgcatagag aaaacccaca agaatatgac agtctgattt     2520
gtcagtctca ttctcaagca acatttctct atccgttact ttcatggtga ataacacaat    2580
ccatcatcaa tactttgtgt tactcagaaa ctgaaagtta ttccgagtct tgcatatctt    2640
tggacctact cgttttttcta ccattattgc tgattgttaa gctctcgcta cttgaatcgg   2700
cattgttgga gtgggaaggt tcaaaaaatt ggagttatga ctagttgtct ctttctatgt    2760
acgatggaga aaatgaataa acaactgaga aaatggctct tgtttagttg atgatgctct    2820 taagcttttcc actggttgcc atatatgatt tgggcatttc actttgatct taatgggcct   2880
tgtaaagccc aagactcatg attatcttta gttgatgctc ttaattaggt gtgggcaaat    2940
aattcaaact gtatgtaccc gaccaaaacc aaagcaaaaa taatcgaacc aaaccgaaaa    3000
tttaaaaata accgaatgaa aactaaatcc tataactgaa agaactgaaa ccgaatcaaa    3060
atatttaatg taaccaaaaa tatccgaaat ataattatat tgtcaaaaat attaataatt    3120
tctagattaa ataattaaaa atacttaaaa atttatataa aatagtaaaa atactcgaaa    3180
ataaccacaa atattcaaaa acaaccgaaa tatcccaaaa tattcaaagc aaaataaccg    3240
aatggatacc aaattttaaa accgaaaaaa ctggaacaaa accaaaatcg aaccaaaatt    3300
tcaaaaatcg aataaatact aaactttaga acaaaaaaaa acgataaccg aatgtatacg    3360
aaccaaagcc gaattagata accgaacgtc caggactact cttaatcttt ccgccactta    3420
tgatttgggc tattactttg tttataatga gccttttcaa gctcaagttc atgattgtcc    3480
gtgagatgag aaactgactt gttggattcg aaaccctagc tagtattggt taatacttaa    3540
tacataaatg acctgcattg acatcatcat ccaagaaaat aaaaattgta tgcttgagat    3600
atttagtttt cctagctagg ttttctttat tttagtaccg aatctttagg tgtgccacgt    3660
taatttagac ccatttttc atacttacca actgagtcta gtttaatcat gactataatc    3720
gtataaaatg attcagtcga cgtcattgcg aacgtatata aaatcatcca aattgacgtc    3780
attccaaaga ggtaagcatg cttatctaag agtccgagca tactaaacaa gacgcacttt    3840
```

```
tatttgcact ccaaatcaaa ttttgtattg cctaaagaaa aacaatcaaa ctcaagtttc    3900
ttaaaattaa tttcattcaa actaatcact ttcaatatct cacatattat tcatgccatt    3960
tctatttgtc taaacatgat ttaaaaaaaa aagtaaaata caaagattac tatgcaaaaa    4020
ctctataaaa aaaaattcaa atttcttatt tatttgtgac atcaaatttt caaaataatt    4080
tttttaatta tcggttgatc cggtcagtcg ataaaaacat aaactttcag cgaccgttaa    4140
aactttccta ctaccgattt agagaaaatc ttagcttgaa acgtaattgt aacctgcctt    4200
catgcaagtc gcaagatatg tcatcctaag ttgtatatgt tttctcaaaa gatgtattta    4260
cttgagaaaa tacgtttcaa cgttgatgga caaccaatta agaatcaagc acctttcgta    4320
atcaatttag gcttatcgtc taaggtatac tgatttacga cagttgacta gacttataag    4380
gaacaaaata atagaataat ttcgtcaaga aaaattgatt ttggactcat actttacata    4440
atattttact cttaaatttta tttaagtggc tcctcgcatg atcccaaaga gcaagcctag    4500
actatatgga aaagtttcta aacacttcac ctaatcatag agactaagat ggtaattcgt    4560
aaacgacaaa gcctagtgac actgtccatt gtaaaattcc acatcatatt agtattaaac    4620
atatacatgt agtttcctga acacatgtag tatcaaacac acttcgtggc ttcttcctcg    4680
aaacctggta ccgcctgcag gggcctatca ggccggatcg aattcattta caattgaata    4740
tatcctgcca ttttacacct cgatatatcc tgccacaaat tccatgtaca cagtacatta    4800
aaaacgtccg caatgtgtta ttaagttgtc taagcgtcaa tttgtttaca ccacaatata    4860
tcctgccacc agccagccaa cagctccccg accggcagct cggcacaaaa tcaccactcg    4920
atacaggcag cccatcagtc cactagaggg ccctgtatgt tattgtattg atctttcatg    4980
atgttgaagt gtgccataat atgatgatgt ataattaaaa tattaactgt cgcatttatt    5040
gaaatggcac tgttatttca accatatctt tgattctgtt acaatgacaa cgactgaaaa    5100
aagtaaataa tagacgccgt tgttaaagaa ttgctatcat atgtgccaaa ctagagggaa    5160
atttacgtca attgtgaaat agtcgccctt attttgacgt ctcacctaat caaatattac    5220
aaaagatcga tctcactctg tcgccagcaa tggtgtaatc agcgcagaca agtggcagta    5280
aagtgcggaa aaacgtcccc gagtggcatg aatagctgcc tctgtattgc tgatttagtc    5340
agccttattt gacttaaggg tgccctcgtt agtgacaaat tgctttcaag gagacagcca    5400
tgccccacac tttgttgaaa aacaaattgc cctttgggga gacggtaaag ccagttgctc    5460
ttcaataagg aatctcgagg aggcaatata accgcctctg gtagtacact tctctaatcc    5520
aaaaagtcaa tttgtattca agataccgca aaaaacttat ggatctgcgt ctaattttcg    5580
gtccaacttg cacaggaaag acgtcgaccg cggtagctct tgcccagcag actgggcttc    5640
cagtcctttc gctcgatcgg gtccaatgtt gtcctcagaa cgcagccgct tacgacggat    5700
tcgaaggtca tccattcgga atgtattagt ttgcaccagc tccgcgtcac acctgtcttc    5760
atttgaataa gatgttcgca attgttttta gctttgtctt gttgtggcag ggcggcaagt    5820
gcttcagaca tcattctgtt ttcaaatttt atgctggaga acagcttctt aattcctttg    5880
gaaataatag actgcgtctt aaaattacga tgcggcggct cggatagtac cgaggaaagg    5940
cagctttgcc aagccgcata gcaatctgct cacgttggga acagattgct aaaggcgaaa    6000
tgcacctcta cctcaggccg ccatcacacc cccgtacgaa acatccacgt cagcgtcaaa    6060
gaaatagcca gcacctcttg cagtcttgat taactgaggg gtcgtcgggt cccctcaag    6120 cttccggcgc agccgcaaaa tgaggacatc aatacttctg tcatacacct cctcctcgcg    6180
tacccgactg gcgatcagaa gctgctcccg ggataggacg tcgcgcggct tctccaggaa    6240
```

```
agcaaccagg agattaaact cacctgccgt gagtttcacc tcactgccct cttccgaaat   6300
caagcggcgt cgcctgagat taagtgtcca gtcagcgaaa ctaaatgagc gtcgatcttt   6360
ggttcgcgcg acactgggcc gcacgcgtaa cgcaacacgg atgcgcgcca gaaattcccg   6420
cgtcccaaaa ggcttggcaa taaaatcggt tgctcccaac tcgagcgcaa taactttgtc   6480
cgcctcttcg aggcgagcgc cgctaataat tatgattgga acatcggact tcgtggccag   6540
actacgaaca atttcaagcc catcttcgcg acccaaatta agatcgacga ccacgacatc   6600
gaccgtctcg gagcagagta cacgattgaa ctgcttgctg tcggctaccg cagtcacctt   6660
aaaggcatgg atcgtaagat actcgactat aagatgccgc atagcgacat cgtcatcgat   6720
gacaagaacg tgtttcaacg gttcacctct caatctaggc tcctggccag ccatttgcag   6780
ctcaacagaa tttatacacg taaaggttgt atttgctaga ctccactctt taattttctc   6840
tcactacacg ggcatttcgg caagatttcg accaaaccgc gcacgacaga aatgcaaact   6900
agatgtctcc gtttgatgac aaagattgct gagcattgct acaaacgtaa ttctacaacg   6960
cgccatgcgg catttagaaa catggatcac aactactgct ggttaagaag atcgcctatt   7020
gtctcaccgc gccgacgcgc atcggcagcg agccagattt cgcccacctc gtaaatgtca   7080
ccgtgggcac ggaagggtac gatgacatca actgcggttg cgagcatgtc aatcagggtg   7140
cgatcttcca agctagcccc ctgagcgctg cttttcacga gcgaatgcag cgaggaagtg   7200
acgcccaccg aggccaggcg gcgcggtgcc ttccgtgagg acgcattgac cgaggccgac   7260
gccctggcgg ccgccgagaa tgaacgccaa gaggaacaag catgaaaccg caccaggacg   7320
gccaggacga accgtttttc attaccgaag agatcgaggc ggagatgatc gcggccgggt   7380
acgtgttcga gccgcccgcg cacgtctcaa ccgtgcggct gcatgaaatc ctggccggtt   7440
tgtctgatgc caagctggcg gcctggccgg ccagcttggc cgctgaagaa accgagcgcc   7500
gccgtctaaa aaggtgatgt gtatttgagt aaaacagctt gcgtcatgcg gtcgctgcgt   7560
atatgatgcg atgagtaaat aaacaaatac gcaaggggaa cgcatgaagg ttatcgctgt   7620
acttaaccag aaaggcgggt caggcaagac gaccatcgca acccatctag cccgcgccct   7680
gcaactcgcc ggggccgatg ttctgttagt cgattccgat ccccagggca gtgcccgcga   7740
ttgggcggcc gtgcgggaag atcaaccgct aaccgttgtc ggcatcgacc gcccgacgat   7800
tgaccgcgac gtgaaggcca tcggccggcg cgacttcgta gtgatcgacg gagcgcccca   7860
ggcggcggac ttggctgtgt ccgcgatcaa ggcagccgac ttcgtgctga ttccggtgca   7920
gccaagccct tacgacatat gggccaccgc cgacctggtg gagctggtta agcagcgcat   7980
tgaggtcacg gatggaaggc tacaagcggc ctttgtcgtg tcgcgggcga tcaaaggcac   8040
gcgcatcggc ggtgaggttg ccgaggcgct ggccgggtac gagctgccca ttcttgagtc   8100
ccgtatcacg cagcgcgtga gctacccagg cactgccgcc gccggcacaa ccgttcttga   8160
atcagaaccc gagggcgacg ctgcccgcga ggtccaggcg ctggccgctg aaattaaatc   8220
aaaactcatt tgagttaatg aggtaaagag aaaatgagca aaagcacaaa cacgctaagt   8280
gccggccgtc cgagcgcacg cagcagcaag gctgcaacgt tggccagcct ggcagacacg   8340
ccagccatga gcgggtcaac ttttcagttg ccggcggagg atcacaccaa gctgaagatg   8400
tacgcggtac gccaaggcaa gaccattacc gagctgctat ctgaatacat cgcgcagcta   8460
ccagagtaaa tgagcaaatg aataaatgag tagatgaatt ttagcggcta aggagcgg   8520
catgaaaaat caagaacaac caggcaccga cgccgtggaa tgccccatgt gtggaggaac   8580
gggcggttgg ccaggcgtaa gcggctgggt tgtctgccgg ccctgcaatg gcactggaac   8640
```

```
ccccaagccc gaggaatcgg cgtgacggtc gcaaaccatc cggcccggta caaatcggcg    8700
cggcgctggg tgatgacctg gtggagaagt tgaaggccgc gcaggccgcc cagcggcaac    8760
gcatcgaggc agaagcacgc cccggtgaat cgtggcaagc ggccgctgat cgaatccgca    8820
aagaatcccg gcaaccgccg gcagccggtg cgccgtcgat taggaagccg cccaagggcg    8880
acgagcaacc agattttttc gttccgatgc tctatgacgt gggcacccgc gatagtcgca    8940
gcatcatgga cgtggccgtt ttccgtctgt cgaagcgtga ccgacgagct ggcgaggtga    9000
tccgctacga gcttccagac gggcacgtag aggtttccgc agggccggcc ggcatggcca    9060
gtgtgtggga ttacgacctg gtactgatgg cggtttccca tctaaccgaa tccatgaacc    9120
gataccggga agggaaggga gacaagcccg ccgcgtgtt ccgtccacac gttgcgacg     9180 tactcaagtt ctgccggcga gccgatggcg gaaagcagaa agacgacctg gtagaaacct    9240
gcattcggtt aaacaccacg cacgttgcca tgcagcgtac gaagaaggcc aagaacggcc    9300
gcctggtgac ggtatccgag ggtgaagcct tgattagccg ctacaagatc gtaaagagcg    9360
aaaccgggcg gccggagtac atcgagatcg agctagctga ttggatgtac cgcgagatca    9420
cagaaggcaa gaacccggac gtgctgacgg ttcaccccga ttacttttg atcgatcccg     9480 gcatcggccg ttttctctac cgcctggcac gccgcgccgc aggcaaggca gaagccagat    9540
ggttgttcaa gacgatctac gaacgcagtg gcagcgccgg agagttcaag aagttctgtt    9600
tcaccgtgcg caagctgatc gggtcaaatg acctgccgga gtacgatttg aaggaggagg    9660
cggggcaggc tggcccgatc ctagtcatgc gctaccgcaa cctgatcgag ggcgaagcat    9720
ccgccggttc ctaatgtacg gagcagatgc tagggcaaat tgccctagca ggggaaaaag    9780
gtcgaaaagg tctctttcct gtggatagca cgtacattgg gaacccaaag ccgtacattg    9840
ggaaccggaa cccgtacatt gggaacccaa agccgtacat tgggaaccgg tcacacatgt    9900
aagtgactga tataaaagag aaaaaaggcg attttccgc ctaaaactct ttaaaactta     9960
ttaaaactct taaacccgc ctggcctgtg cataactgtc tggccagcgc acagccgaag    10020
agctgcaaaa agcgcctacc cttcggtcgc tgcgctccct acgccccgcc gcttcgcgtc    10080
ggcctatcgc ggccgctgca tataattgtg gttttcaaaat cggctccgtc gatactatgt    10140
tatacgccaa ctttgaaaac aactttgaaa aagctgtttt ctggtattta aggttttaga    10200
atgcaaggaa cagtgaattg gagttcgtct tgttataatt agcttcttgg ggtatcttta    10260
aatactgtag aaaagaggaa ggaaataata aatggctaaa atgagaatat caccggaatt    10320
gaaaaaactg atcgaaaaat accgctgcgt aaaagatacg gaaggaatgt ctcctgctaa    10380
ggtatataag ctggtgggag aaaatgaaaa cctatattta aaaatgacgg acagccggta    10440
taaagggacc acctatgatg tggaacggga aaaggacatg atgctatggc tggaaggaaa    10500
gctgcctgtt ccaaaggtcc tgcactttga acggcatgat ggctggagca atctgctcat    10560
gagtgaggcc gatggcgtcc tttgctcgga agagtatgaa gatgaacaaa gccctgaaaa    10620
gattatcgag ctgtatgcgg agtgcatcag gctctttcac tccatcgaca tatcggattg    10680
tccctatacg aatagcttag acagccgctt agccgaattg gattacttac tgaataacga    10740
tctggccgat gtggattgcg aaaactggga agaagacact ccatttaaag atccgcgcga    10800
gctgtatgat tttttaaaga cggaaaagcc cgaagaggaa cttgtctttt cccacggcga    10860
cctgggagac agcaacatct ttgtgaaaga tggcaaagta agtggcttta ttgatcttgg    10920
gagaagcggc agggcggaca agtggtatga cattgccttc tgcgtccggt cgatcaggga    10980
ggatatcggg gaagaacagt atgtcgagct attttttgac ttactgggga tcaagcctga    11040
```

```
ttgggagaaa ataaaatatt atattttact ggatgaattg ttttagtacc tagatacgta    11100
accaactagt gcgctcttcc gcttcctcgc tcactgactc gctgcgctcg gtcgttcggc    11160
tgcggcgagc ggtatcagct cactcaaagg cggtaatacg gttatccaca gaatcagggg    11220
ataacgcagg aaagaacatg tgagcaaaag gccagcaaaa ggccaggaac cgtaaaaagg    11280
ccgcgttgct ggcgtttttc cataggctcc gcccccctga cgagcatcac aaaaatcgac    11340
gctcaagtca gaggtggcga acccgacag gactataaag ataccaggcg tttccccctg     11400
gaagctccct cgtgcgctct cctgttccga ccctgccgct taccggatac ctgtccgcct    11460
ttctcccttc gggaagcgtg gcgctttctc atagctcacg ctgtaggtat ctcagttcgg    11520
tgtaggtcgt tcgctccaag ctgggctgtg tgcacgaacc ccccgttcag cccgaccgct    11580
gcgccttatc cggtaactat cgtcttgagt ccaacccggt aagacacgac ttatcgccac    11640
tggcagcagc cactggtaac aggattagca gagcgaggta tgtaggcggt gctacagagt    11700
tcttgaagtg gtggcctaac tacggctaca ctagaaggac agtatttggt atctgcgctc    11760
tgctgaagcc agttaccttc ggaaaaagag ttggtagctc ttg                      11803

<210> SEQ ID NO 75
<211> LENGTH: 11746
<212> TYPE: DNA
<213> ORGANISM: Artificial Sequence
<220> FEATURE:
<223> OTHER INFORMATION: Vector containing the BAA-LBNL-5220 construct

<400> SEQUENCE: 75
atccggcaaa caaaccaccg ctggtagcgg tggttttttt gtttgcaagc agcagattac      60
gcgcagaaaa aaaggatctc aagaagatcc tttgatcttt tctacggggt ctgacgctca     120
gtggaacgaa aactcacgtt aagggatttt ggtcatgaga ttatcaaaaa ggatcttcac     180
ctagatcctt ttaaattaaa aatgaagcgt acgttggaat cgcttctaca aaactcacag     240
aaacaatcaa acaaacatac acagcgattt attcacacga acccgaatta caacggtata     300
tatcctgtca gccaacacca aaacatcaaa aaaatcggga tcaggatcag gatctgcggc     360
cgcatcctgc aggtcgactc tagaggatcc cccaattcgt caacttcgtc cacagacatc     420
aacatcttat cgtcctttga agataagata taatgttga agataagagt gggagccccc      480
actaaaacat tgctttgtca aaagctaaaa aagatgatgc ccgacagcca cttgtgtgaa     540
gcatgagaag ccggtccctc cactaagaaa attagtgaag catcttccag tggtccctcc     600
actcacagct caatcagtga gcaacaggac gaaggaaatg acgtaagcca tgacgtctaa     660
tcccaacttc gtccacagac atcaacatct tatcgtcctt tgaagataag ataataatgt     720
tgaagataag agtgggagcc accactaaaa cattgctttg tcaaaagcta aaaagatga     780 tgcccgacag ccacttgtgt gaagcatgag aagccggtcc ctccactaag aaaattagtg     840
aagcatcttc cagtggtccc tccactcaca gctcaatcag tgagcaacag gacgaaggaa     900
atgacgtaag ccatgacgtc taatcccaca agaatttcct tatataagga acacaaatca     960
gaaggaagag atcaatcgaa atcaaaatcg gaatcgaaat caaaatcgga atcgaaatct    1020
ctcatctaag agctcaaaaa aaaaaaaaac catggggaac aaacatttgt ccctctccct    1080
cttcctcgtc ctccttgggc tgtcggccag cttggcctcc ggactcaagt acaccggcac    1140
ctgcacccgc gctaacaacc agtgcaagta cagggtcag aacgatcgcg ataccttcgt     1200
gaagtgccca accttcgcca acaagaagtg cacgcgcgat ggcgctccct gctccttcga    1260
ctcatacagc cgcgccgtca cctgcgactg aggcgcgcct aggttttttgt gatctgatga    1320
```

```
taagtggttg gttcgtgtct catgcacttg ggaggtgatc tatttcacct ggtgtagttt    1380
gtgtttccgt cagttggaaa aacttatccc tatcgatttc gttttcattt tctgcttttc    1440
ttttatgtac cttcgtttgg gcttgtaacg ggcctttgta tttcaactct caataataat    1500
ccaagtgcat gttaaacaat tgtcatctg tttcggcttt gatatactac tggtgaagat    1560
gggccgtact actgcatcac aacgaaaaat aataataaga tgaaaaactt gaagtggaaa    1620
aaaaaaaaaa cttgaatgtt cactactact cattgaccat aatgtttaac atacatagct    1680
caatagtatt tttgtgaata tggcaacaca aacagtccaa aacaattgtc tcttactata    1740
ccaaaccaag ggcgccgctt gtttgccact ctttgtgtgc aatagtgtga ttaccacatc    1800
tccacattca atatattccc tgaattatct gacgattttg atggctcact gttttcccaa    1860
gtcttgaatt gtcttctgtg cgccagtcaa atgcatatgt gttgagttta tcttttaaat    1920
atcaagcttt tgttttaac ttttgtttgt aaccaaaaac tcacagtagg agtttgatca    1980
cataatttta tgtttgcctt tgcaatttct agtgagtctt tgattaaaag cttgaaaaga    2040
aaatgcagcc aagcttacca agtaagttat gtgtattaac cagaggaaga gagaatcttg    2100
caaaatttca acaaacacaa aaagaagtat tactacgatt ggtggagaaa gaaaacgatt    2160
ccaaatcttg aactgttgtt gtaaaagcat agcagaaagt gggagacaac cgaaatagaa    2220
atgactataa cttaatttaa tgttatcatt ataatttctt ctagcaaata tttagaaagt    2280
aaatatcaca tcaaccttta atgtaattaa gctttctctt tttgattcat gtgagatgaa    2340
aagaaaaaaa agaagagaaa agtgtagaaa acacatcatt tctaagctga aggtacatag    2400
tacccttgta cttttggttt cacctgcata gagaaaaccc acaagaatat gacagtctga    2460
tttgtcagtc tcattctcaa gcaacatttc tctatccgtt actttcatgg tgaataacac    2520
aatccatcat caatactttg tgttactcag aaactgaaag ttattccgag tcttgcatat    2580
ctttggacct actcgttttt ctaccattat tgctgattgt taagctctcg ctacttgaat    2640
cggcattgtt ggagtgggaa ggttcaaaaa attggagtta tgactagttg tctctttcta    2700
tgtacgatgg agaaaatgaa taaacaactg agaaaatggc tcttgtttag ttgatgatgc    2760
tcttaagctt tccactggtt gccatatatg atttgggcat ttcactttga tcttaatggg    2820
ccttgtaaag cccaagactc atgattatct ttagttgatg ctcttaatta ggtgtgggca    2880
aataattcaa actgtatgta cccgaccaaa accaaagcaa aaataatcga accaaaccga    2940
aaatttaaaa ataaccgaat gaaaactaaa tcctataact gaaagaactg aaaccgaatc    3000
aaaatattta atgtaaccaa aaatatccga aatataatta tattgtcaaa atattaata    3060
atttctagat taaataatta aaaatactta aaaatttata taaaatagta aaaatactcg    3120
aaaataacca caaatattca aaaacaaccg aaatatccca aaatattcaa agcaaaataa    3180
ccgaatggat accaaatttt aaaaccgaaa aaactggaac aaaaccaaaa tcgaaccaaa    3240
atttcaaaaa tcgaataaat actaaacttt agaacaaaaa aaaacgataa ccgaatgtat    3300
acgaaccaaa gccgaattag ataaccgaac gtccaggact actcttaatc tttccgccac    3360
ttatgatttg ggctattact ttgttttataa tgagcctttt caagctcaag ttcatgattg    3420
tccgtgagat gagaaactga cttgttggat tcgaaaccct agctagtatt ggttaatact    3480
taatacataa atgacctgca ttgacatcat catccaagaa aataaaaatt gtatgcttga    3540
gatatttagt tttcctagct aggttttctt tatttagta ccgaatcttt aggtgtgcca    3600
cgttaattta gacccatttt ttcatactta ccaactgagt ctagtttaat catgactata    3660
atcgtataaa atgattcagt cgacgtcatt gcgaacgtat ataaaatcat ccaaattgac    3720
```

```
gtcattccaa agaggtaagc atgcttatct aagagtccga gcatactaaa caagacgaca    3780
ttttatttgc actccaaatc aaattttgta ttgcctaaag aaaaacaatc aaactcaagt    3840
ttcttaaaat taatttcatt caaactaatc actttcaata tctcacatat tattcatgcc    3900
atttctattt gtctaaacat gatttaaaaa aaaagtaaa atacaaagat tactatgcaa    3960
aaactctata aaaaaaatt caaatttctt atttatttgt gacatcaaat tttcaaaata    4020 attttttaa ttatcggttg atccggtcag tcgataaaaa cataaacttt cagcgaccgt    4080
taaaactttc ctactaccga tttagagaaa atcttagctt gaaacgtaat tgtaacctgc    4140
cttcatgcaa gtcgcaagat atgtcatcct aagttgtata tgttttctca aaagatgtat    4200
ttacttgaga aaatacgttt caacgttgat ggacaaccaa ttaagaatca agcacctttc    4260
gtaatcaatt taggcttatc gtctaaggta tactgattta cgacagttga ctagacttat    4320
aaggaacaaa ataatagaat aatttcgtca agaaaaattg attttggact catactttac    4380
ataatatttt actcttaaat ttatttaagt ggctcctcgc atgatcccaa agagcaagcc    4440
tagactatat ggaaaagttt ctaaacactt cacctaatca tagagactaa gatggtaatt    4500
cgtaaacgac aaagcctagt gacactgtcc attgtaaaat tccacatcat attagtatta    4560
aacatataca tgtagtttcc tgaacacatg tagtatcaaa cacacttcgt ggcttcttcc    4620
tcgaaacctg gtaccgcctg caggggccta tcaggccgga tcgaattcat ttacaattga    4680
atatatcctg ccattttaca cctcgatata tcctgccaca aattccatgt acacagtaca    4740
ttaaaaacgt ccgcaatgtg ttattaagtt gtctaagcgt caatttgttt acaccacaat    4800
atatcctgcc accagccagc caacagctcc ccgaccggca gctcggcaca aaatcaccac    4860
tcgatacagg cagcccatca gtccactaga gggccctgta tgttattgta ttgatctttc    4920
atgatgttga agtgtgccat aatatgatga tgtataatta aaatattaac tgtcgcattt    4980
attgaaatgg cactgttatt tcaaccatat cttttgattct gttacaatga caacgactga    5040
aaaaagtaaa taatagacgc cgttgttaaa gaattgctat catatgtgcc aaactagagg    5100
gaaatttacg tcaattgtga aatagtcgcc cttattttga cgtctcacct aatcaaatat    5160
tacaaaagat cgatctcact ctgtcgccag caatggtgta atcagcgcag acaagtggca    5220
gtaaagtgcg gaaaaacgtc cccgagtggc atgaatagct gcctctgtat tgctgattta    5280
gtcagcctta tttgacttaa gggtgccctc gttagtgaca aattgctttc aaggagacag    5340
ccatgcccca cactttgttg aaaaacaaat tgcccttttgg ggagacggta aagccagttg    5400
ctcttcaata aggaatctcg aggaggcaat ataaccgcct ctggtagtac acttctctaa    5460
tccaaaaagt caatttgtat tcaagatacc gcaaaaaact tatggatctg cgtctaattt    5520
tcggtccaac ttgcacagga aagacgtcga ccgcggtagc tcttgcccag cagactgggc    5580
ttccagtcct ttcgctcgat cgggtccaat gttgtcctca gaacgcagcc gcttacgacg    5640
gattcgaagg tcatccattc ggaatgtatt agtttgcacc agctccgcgt cacacctgtc    5700
ttcatttgaa taagatgttc gcaattgttt ttagctttgt cttgttgtgg cagggcggca    5760
agtgcttcag acatcattct gttttcaaat tttatgctgg agaacagctt cttaattcct    5820
ttggaaataa tagactgcgt cttaaaatta cgatgcggcg gctcggatag taccgaggaa    5880
aggcagcttt gccaagccgc atagcaatct gctcacgttg ggaacagatt gctaaaggcg    5940
aaatgcacct ctacctcagg ccgccatcac accccgtac gaaacatcca cgtcagcgtc    6000
aaagaaatag ccagcacctc ttgcagtctt gattaactga ggggtcgtcg ggtcccctc    6060 aagcttccgg cgcagccgca aaatgaggac atcaatactt ctgtcataca cctcctcctc    6120
```

```
gcgtacccga ctggcgatca gaagctgctc ccgggatagg acgtcgcgcg gcttctccag    6180
gaaagcaacc aggagattaa actcacctgc cgtgagtttc acctcactgc cctcttccga    6240
aatcaagcgg cgtcgcctga gattaagtgt ccagtcagcg aaactaaatg agcgtcgatc    6300
tttggttcgc gcgacactgg gccgcacgcg taacgcaaca cggatgcgcg ccagaaattc    6360
ccgcgtccca aaaggcttgg caataaaatc ggttgctccc aactcgagcg caataacttt    6420
gtccgcctct tcgaggcgag cgccgctaat aattatgatt ggaacatcgg acttcgtggc    6480
cagactacga acaatttcaa gcccatcttc gcgacccaaa ttaagatcga cgaccacgac    6540
atcgaccgtc tcggagcaga gtacacgatt gaactgcttg ctgtcggcta ccgcagtcac    6600
cttaaaggca tggatcgtaa gatactcgac tataagatgc cgcatagcga catcgtcatc    6660
gatgacaaga acgtgtttca acggttcacc tctcaatcta ggctcctggc cagccatttg    6720
cagctcaaca gaatttatac acgtaaaggt tgtatttgct agactccact ctttaatttt    6780
ctctcactac acgggcattt cggcaagatt tcgaccaaac cgcgcacgac agaaatgcaa    6840
actagatgtc tccgtttgat gacaaagatt gctgagcatt gctacaaacg taattctaca    6900
acgcgccatg cggcatttag aaacatggat cacaactact gctggttaag aagatcgcct    6960
attgtctcac cgcgccgacg cgcatcggca gcgagccaga tttcgcccac ctcgtaaatg    7020
tcaccgtggg cacggaaggg tacgatgaca tcaactgcgg ttgcgagcat gtcaatcagg    7080
gtgcgatctt ccaagctagc cccctgagcg ctgcttttca cgagcgaatg cagcgaggaa    7140
gtgacgccca ccgaggccag gcggcgcggt gccttccgtg aggacgcatt gaccgaggcc    7200
gacgccctgg cggccgccga gaatgaacgc caagaggaac aagcatgaaa ccgcaccagg    7260
acggccagga cgaaccgttt ttcattaccg aagagatcga ggcggagatg atcgcggccg    7320
ggtacgtgtt cgagccgccc gcgcacgtct caaccgtgcg gctgcatgaa atcctggccg    7380
gtttgtctga tgccaagctg gcggcctggc cggccagctt ggccgctgaa gaaaccgagc    7440
gccgccgtct aaaaaggtga tgtgtatttg agtaaaacag cttgcgtcat gcggtcgctg    7500
cgtatatgat gcgatgagta aataaacaaa tacgcaaggg gaacgcatga aggttatcgc    7560
tgtacttaac cagaaaggcg ggtcaggcaa gacgaccatc gcaacccatc tagcccgcgc    7620
cctgcaactc gccggggccg atgttctgtt agtcgattcc gatcccccag gcagtgcccg    7680
cgattgggcg gccgtgcggg aagatcaacc gctaaccgtt gtcggcatcg accgcccgac    7740
gattgaccgc gacgtgaagg ccatcggccg gcgcgacttc gtagtgatcg acggagcgcc    7800
ccaggcggcg gacttggctg tgtccgcgat caaggcagcc gacttcgtgc tgattccggt    7860
gcagccaagc ccttacgaca tatgggccac cgccgacctg gtggagctgg ttaagcagcg    7920
cattgaggtc acggatggaa ggctacaagc ggcctttgtc gtgtcgcggg cgatcaaagg    7980
cacgcgcatc ggcggtgagg ttgccgaggc gctggccggg tacgagctgc ccattcttga    8040
gtcccgtatc acgcagcgcg tgagctaccc aggcactgcc gccgccggca aaccgttcct    8100
tgaatcagaa cccgagggcg acgctgcccg cgaggtccag gcgctggccg ctgaaattaa    8160
atcaaaactc atttgagtta atgaggtaaa gagaaaatga gcaaaagcac aaacacgcta    8220
agtgccggcc gtccgagcgc acgcagcagc aaggctgcaa cgttggccag cctggcagac    8280
acgccagcca tgaagcgggt caactttcag ttgccggcgg aggatcacac caagctgaag    8340
atgtacgcgg tacgccaagg caagaccatt accgagctgc tatctgaata catcgcgcag    8400
ctaccagagt aaatgagcaa atgaataaat gagtagatga attttagcgg ctaaaggagg    8460
cggcatggaa aatcaagaac aaccaggcac cgacgccgtg gaatgcccca tgtgtggagg    8520
```

```
aacgggcggt tggccaggcg taagcggctg ggttgtctgc cggccctgca atggcactgg    8580
aacccccaag cccgaggaat cggcgtgacg gtcgcaaacc atccggcccg gtacaaatcg    8640
gcgcggcgct gggtgatgac ctggtggaga agttgaaggc cgcgcaggcc gcccagcggc    8700
aacgcatcga ggcagaagca cgccccggtg aatcgtggca agcggccgct gatcgaatcc    8760
gcaaagaatc ccggcaaccg ccggcagccg gtgcgccgtc gattaggaag ccgcccaagg    8820
gcgacgagca accagatttt ttcgttccga tgctctatga cgtgggcacc cgcgatagtc    8880
gcagcatcat ggacgtggcc gttttccgtc tgtcgaagcg tgaccgacga gctggcgagg    8940
tgatccgcta cgagcttcca gacgggcacg tagaggtttc cgcagggccg gccggcatgg    9000
ccagtgtgtg ggattacgac ctggtactga tggcggtttc ccatctaacc gaatccatga    9060
accgataccg ggaagggaag ggagacaagc ccggccgcgt gttccgtcca cacgttgcgg    9120
acgtactcaa gttctgccgg cgagccgatg gcggaaagca gaaagacgac ctggtagaaa    9180
cctgcattcg gttaaacacc acgcacgttg ccatgcagcg tacgaagaag gccaagaacg    9240
gccgcctggt gacggtatcc gagggtgaag ccttgattag ccgctacaag atcgtaaaga    9300
gcgaaaccgg gcgccggag tacatcgaga tcgagctagc tgattggatg taccgcgaga    9360
tcacagaagg caagaacccg gacgtgctga cggttcaccc cgattacttt ttgatcgatc    9420
ccggcatcgg ccgttttctc taccgcctgg cacgccgcgc cgcaggcaag gcagaagcca    9480
gatggttgtt caagacgatc tacgaacgca gtggcagcgc cggagagttc aagaagttct    9540
gtttcaccgt gcgcaagctg atcgggtcaa atgacctgcc ggagtacgat ttgaaggagg    9600
aggcggggca ggctggcccg atcctagtca tgcgctaccg caacctgatc gagggcgaag    9660
catccgccgg ttcctaatgt acggagcaga tgctagggca aattgcccta gcaggggaaa    9720
aaggtcgaaa aggtctcttt cctgtggata gcacgtacat tgggaaccca agccgtaca    9780
ttgggaaccg gaacccgtac attgggaacc caaagccgta cattgggaac cggtcacaca    9840
tgtaagtgac tgatataaaa gagaaaaaag gcgattttc cgcctaaaac tctttaaaac    9900
ttattaaaac tcttaaaacc cgcctggcct gtgcataact gtctggccag cgcacagccg    9960
aagagctgca aaaagcgcct acccttcggt cgctgcgctc cctacgcccc gccgcttcgc    10020
gtcggcctat cgcggccgct gcatataatt gtggtttcaa aatcggctcc gtcgatacta    10080
tgttatacgc caactttgaa aacaactttg aaaaagctgt tttctggtat ttaaggtttt    10140
agaatgcaag gaacagtgaa ttggagttcg tcttgttata attagcttct tggggtatct    10200
ttaaatactg tagaaaagag gaaggaaata ataaatggct aaaatgagaa tatcaccgga    10260
attgaaaaaa ctgatcgaaa aataccgctg cgtaaaagat acggaaggaa tgtctcctgc    10320
taaggtatat aagctggtgg gagaaaatga aaacctatat ttaaaaatga cggacagccg    10380
gtataaaggg accacctatg atgtggaacg ggaaaaggac atgatgctat ggctggaagg    10440
aaagctgcct gttccaaagg tcctgcactt tgaacggcat gatggctgga gcaatctgct    10500
catgagtgag gccgatggcg tccttttgctc ggaagagtat gaagatgaac aaagccctga    10560
aaagattatc gagctgtatg cggagtgcat caggctcttt cactccatcg acatatcgga    10620
ttgtccctat acgaatagct tagacagccg cttagccgaa ttggattact tactgaataa    10680
cgatctggcc gatgtggatt gcgaaaactg ggaagaagac actccattta agatccgcg    10740
cgagctgtat gatttttaa agacggaaaa gcccgaagag gaacttgtct tttcccacgg    10800
cgacctggga gacagcaaca tctttgtgaa agatggcaaa gtaagtggct ttattgatct    10860
tgggagaagc ggcagggcgg acaagtggta tgacattgcc ttctgcgtcc ggtcgatcag    10920
```

```
ggaggatatc ggggaagaac agtatgtcga gctatttttt gacttactgg ggatcaagcc  10980
tgattgggag aaaataaaat attatatttt actggatgaa ttgttttagt acctagatac  11040
gtaaccaact agtgcgctct tccgcttcct cgctcactga ctcgctgcgc tcggtcgttc  11100
ggctgcggcg agcggtatca gctcactcaa aggcggtaat acggttatcc acagaatcag  11160
gggataacgc aggaaagaac atgtgagcaa aaggccagca aaaggccagg aaccgtaaaa  11220
aggccgcgtt gctggcgttt ttccataggc tccgccccc tgacgagcat cacaaaaatc  11280
gacgctcaag tcagaggtgg cgaaacccga caggactata aagataccag gcgtttcccc  11340
ctggaagctc cctcgtgcgc tctcctgttc cgaccctgcc gcttaccgga tacctgtccg  11400
cctttctccc ttcgggaagc gtggcgcttt ctcatagctc acgctgtagg tatctcagtt  11460
cggtgtaggt cgttcgctcc aagctgggct gtgtgcacga accccccgtt cagcccgacc  11520
gctgcgcctt atccggtaac tatcgtcttg agtccaaccc ggtaagacac gacttatcgc  11580
cactggcagc agccactggt aacaggatta gcagagcgag gtatgtaggc ggtgctacag  11640
agttcttgaa gtggtggcct aactacggct acactagaag gacagtattt ggtatctgcg  11700
ctctgctgaa gccagttacc ttcggaaaaa gagttggtag ctcttg            11746
```

ANTIFUNGAL POLYPEPTIDES

CROSS REFERENCE TO RELATED APPLICATIONS

This application is a divisional of U.S. application Ser. No. 11/833,598, filed Aug. 3, 2007, now U.S. Pat. No. 7,772,370, which claims the benefit of U.S. Divisional application Ser. No. 11/174,413, filed Jul. 1, 2005, now U.S. Pat. No. 7,306,946, which claims the benefit of U.S. Provisional Application Ser. No. 60/585,267, filed on Jul. 2, 2004, both of which are incorporated herein by reference in their entirety.

FEDERALLY SPONSORED RESEARCH OR DEVELOPMENT

This invention was made with government support under contract number DE-AC02-05CH11231 awarded by the United States Department of Energy. The government has certain rights in the invention.

FIELD OF THE INVENTION

The present invention relates to polypeptides having antipathogenic activity and the nucleic acid sequences that encode them. Methods of the invention utilize these antipathogenic polypeptides and nucleic acid sequences to control plant pathogens and to increase pathogen resistance in plants.

BACKGROUND OF THE INVENTION

Plant diseases are often a serious limitation on agricultural productivity and therefore have influenced the history and development of agricultural practices. A variety of pathogens are responsible for plant diseases, including fungi, bacteria, viruses, and nematodes. Among the causal agents of infectious diseases of crop plants, however, fungi are the most economically important group of plant pathogens and are responsible for huge annual losses of marketable food, fiber, and feed.

Incidence of plant diseases has traditionally been controlled by agronomic practices that include crop rotation, the use of agrochemicals, and conventional breeding techniques. The use of chemicals to control plant pathogens, however, increases costs to farmers and causes harmful effects on the ecosystem. Consumers and government regulators alike are becoming increasingly concerned with the environmental hazards associated with the production and use of synthetic agrochemicals for protecting plants from pathogens. Because of such concerns, regulators have banned or limited the use of some of the most hazardous chemicals. The incidence of fungal diseases has been controlled to some extent by breeding resistant crops. Traditional breeding methods, however, are time-consuming and require continuous effort to maintain disease resistance as pathogens evolve. See, for example, Grover and Gowthaman (2003) *Curr. Sci.* 84:330-340. Thus, there is a significant need for novel alternatives for the control of plant pathogens that possess a lower risk of pollution and environmental hazards than is characteristic of traditional agrochemical-based methods and that are less cumbersome than conventional breeding techniques.

Many plant diseases, including, but not limited to, maize stalk rot and ear mold, can be caused by a variety of pathogens. Stalk rot, for example, is one of the most destructive and widespread diseases of maize. The disease is caused by a complex of fungi and bacteria that attack and degrade stalks near plant maturity. Significant yield loss can occur as a result of lodging of weakened stalks as well as premature plant death. Maize stalk rot is typically caused by more than one fungal species, but Gibberella stalk rot, caused by *Gibberella zeae*, Fusarium stalk rot, caused by *Fusarium verticillioides*, *F. proliferatum*, or *F. subglutinans*, and Anthracnose stalk rot, caused by *Colletotrichum graminicola* are the most frequently reported (Smith and White (1988); Diseases of corn, pp. 701-766 in Corn and Corn Improvement, Agronomy Series #18 (3rd ed.), Sprague, C. F., and Dudley, J. W., eds. Madison, Wis.). Due to the fact that plant diseases can be caused by a complex of pathogens, broad spectrum resistance is required to effectively mediate disease control. Thus, a significant need exists for antifungal compositions that target multiple stalk rot and ear mold-causing pathogens.

Recently, agricultural scientists have developed crop plants with enhanced pathogen resistance by genetically engineering plants to express antipathogenic proteins. For example, potatoes and tobacco plants genetically engineered to produce an antifungal endochitinase protein were shown to exhibit increased resistance to foliar and soil-borne fungal pathogens. See Lorito et al. (1998) *Proc. Natl. Acad. Sci.* 95:7860-7865. Moreover, transgenic barley that is resistant to the stem rust fungus has also been developed. See Horvath et al. (2003) *Proc. Natl. Acad. Sci.* 100:364-369. A continuing effort to identify antipathogenic agents and to genetically engineer disease-resistant plants is underway.

Thus, in light of the significant impact of plant pathogens, particularly fungal pathogens, on the yield and quality of crops, new compositions and methods for protecting plants from pathogens are needed. Methods and compositions for controlling multiple fungal pathogens are of particular interest.

BRIEF SUMMARY OF THE INVENTION

Compositions and methods for protecting a plant from a pathogen are provided. The compositions include novel nucleotide and amino acid sequences for antipathogenic, particularly antifungal, polypeptides. The polypeptides of the invention display antipathogenic activity against plant fungal pathogens. More particularly, the compositions of the invention comprise the antipathogenic polypeptides set forth in SEQ ID NOs:1, 3, 5, 7, and 9, and variants and fragments thereof. Nucleic acid molecules comprising nucleotide sequences that encode the antipathogenic polypeptides of the invention are further provided. Compositions also include expression cassettes comprising a promoter operably linked to a nucleotide sequence that encodes an antipathogenic polypeptide of the invention. Transformed plants, plant cells, seeds, and microorganisms comprising an expression cassette of the invention are further provided.

The compositions of the invention are useful in methods directed to inducing pathogen resistance, particularly fungal resistance, in plants. In particular embodiments, the methods comprise introducing into a plant at least one expression cassette comprising a promoter operably linked to a nucleotide sequence that encodes an antipathogenic polypeptide of the invention. As a result, the antipathogenic polypeptide is expressed in the plant, and the pathogen is exposed to the protein at the site of pathogen attack, thereby leading to increased pathogen resistance. A tissue-preferred promoter may be used to drive expression of an antipathogenic protein in specific plant tissues that are particularly vulnerable to pathogen attack, such as, for example, the roots, leaves, stalks, vascular tissues, and seeds. Pathogen-inducible promoters may also be used to drive expression of an antipathogenic protein of the invention at or near the site of pathogen infection.

The present invention further provides antipathogenic compositions and formulations and methods for their use in protecting a plant from a pathogen, particularly a fungal pathogen. In some embodiments, compositions comprise an antipathogenic polypeptide or a transformed microorganism comprising a nucleotide sequence encoding an antipathogenic polypeptide of the invention in combination with a carrier. Methods of using these compositions to protect a plant from a pathogen comprise applying the antipathogenic composition to the environment of the plant pathogen by, for example, spraying, dusting, broadcasting, or seed coating. The methods and compositions of the invention find use in protecting plants from pathogens, including fungal pathogens, viruses, nematodes, and the like.

BRIEF DESCRIPTION OF THE DRAWINGS

FIG. 1 shows a sequence alignment of the amino acid sequences of the invention with various known proteins sharing sequence similarity to the polypeptides disclosed herein. Consensus sequences derived from the highlighted region of all polypeptides appearing in the alignment are further provided.

FIG. 2 shows a sequence alignment of the novel amino acid sequences of the invention.

FIG. 7 provides the photographic results of a *F. verticillioides* antifungal activity assay performed using transgenic LBNL-5220 (SEQ ID NO:1) callus extracts. Experimental details are provided in Example 9.

FIG. 10 provides the distribution of lower stalk *C. graminicola* resistance scores for control and LBNL-5220 transgenic maize plants. Experimental details are provided in Example 10.

DETAILED DESCRIPTION OF THE INVENTION

Figure 3:
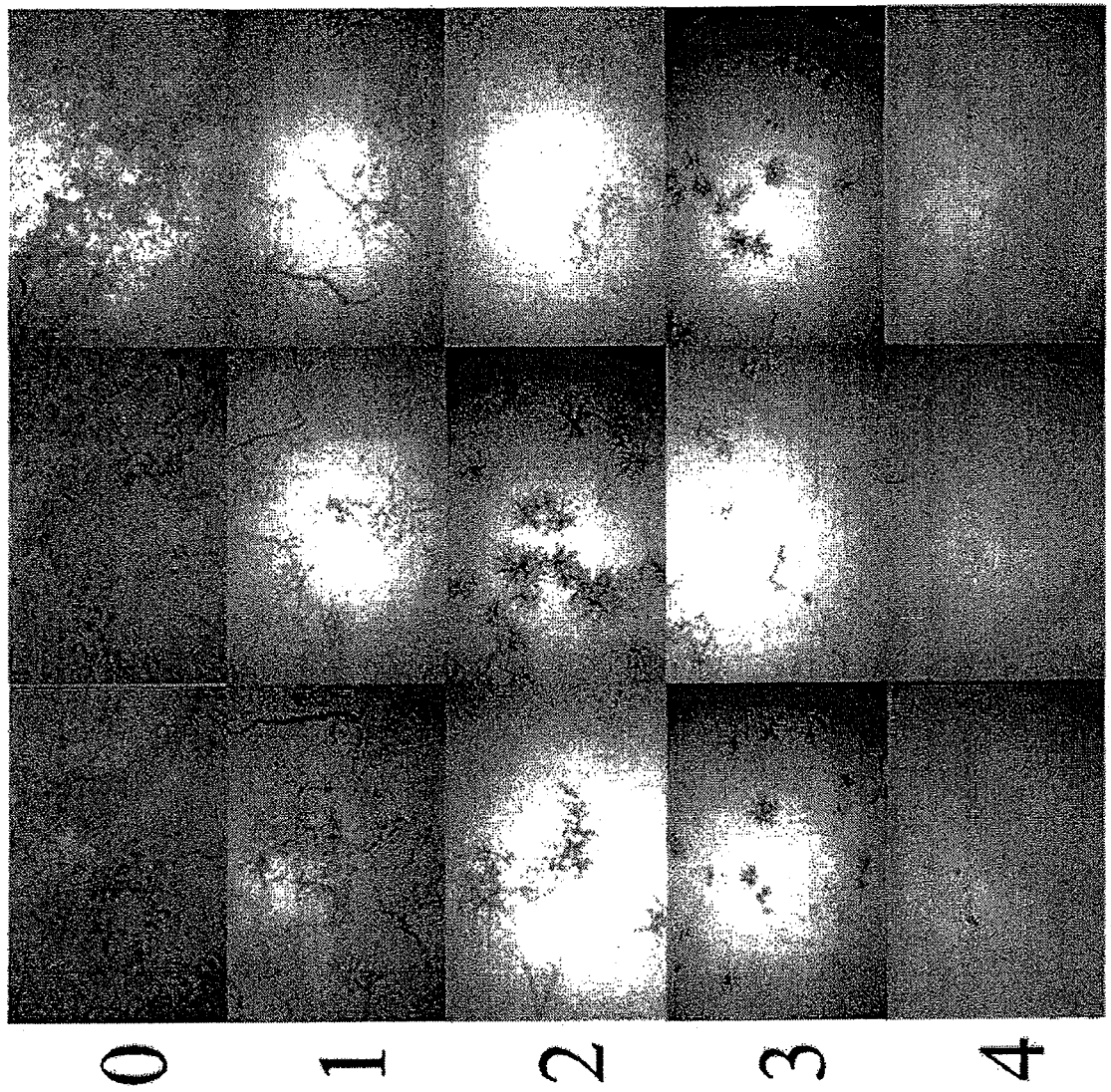
FIG. 3 shows photographic examples of the level of inhibition associated with each numerical score in the antifungal plate assay described in Example 3.

The present invention provides compositions and methods directed to inducing pathogen resistance, particularly fungal resistance, in plants. The compositions are novel nucleotide and amino acid sequences for antipathogenic polypeptides. Specifically, the present invention provides antipathogenic polypeptides having the amino acid sequences set forth in SEQ ID NOs:1, 3, 5, 7, and 9, and variants and fragments thereof, that were isolated from various microbial fermentation broths. Isolated nucleic acid molecules, and variants and fragments thereof, comprising nucleotide sequences that encode the amino acid sequences shown in SEQ ID NOs:1, 3, 5, 7, and 9 are further provided.

Nucleotide sequences that are optimized for expression in plants, particularly maize, and that encode the polypeptides of SEQ ID NOs:1, 3, 5, 7, and 9 were generated using standard methods known in the art. These deduced nucleotide sequences are set forth in SEQ ID NOs:2, 4, 6, 8, and 10. Plants, plant cells, seeds, and microorganisms comprising a nucleotide sequence that encodes an antipathogenic polypeptide of the invention are also disclosed herein. Antipathogenic compositions comprising an isolated antipathogenic, particularly an antifungal, polypeptide or a microorganism that expresses a polypeptide of the invention in combination with a carrier are further provided. The compositions of the invention find use in generating pathogen-resistant plants and in protecting plants from pathogens, particularly fungal pathogens.

The polypeptides disclosed herein in SEQ ID NOs:1, 3, 5, 7, and 9 display antifungal activity against fungal plant pathogens, such as, for example, *Colletotrichum graminocola*, *Diplodia maydis*, *Fusarium graminearum*, and *Fusarium verticillioides*. The species of origin of these antifungal polypeptides has been determined. These proteins are of filamentous fungal origin. In particular, the fungal source of polypeptide SEQ ID NO:1 is *Penicillium simplicissimum*, while the fungal source of the polypeptides SEQ ID NOs:3 and 5 are two strains of the species *Penicillium miczyinskii*. The fungal source of the polypeptides of SEQ ID NOs:7 and 9 is *Monascus ruber*.

Additional novel polypeptides are provided that share homology with the amino acid sequences set forth in SEQ ID NOs:1, 3, 5, 7, and 9. In particular, the polypeptides set forth in SEQ ID NOs:11 and 15 were identified using computer homology searches from a fungal contaminant of maize and from *Fusarium graminearum*, respectively. Mature peptides lacking an N-terminal peptide present in the full-length sequences of SEQ ID NO:11 and 15 are also disclosed and set forth in SEQ ID NOs: 13 and 17. Isolated nucleic acid molecules, and variants and fragments thereof, comprising nucleotide sequences that encode the amino acid sequences shown in SEQ ID NOs:11, 13, 15, and 17 are further provided.

Nucleotide sequences that encode these polypeptides have been generated, and these deduced sequences are set forth in SEQ ID NOs:12, 14, 16, and 18.

The polypeptides of the invention share homology with known antifungal proteins, as well as other proteins of unknown function. In particular, the novel polypeptides of the invention share homology with antifungal proteins isolated from *Aspergillus giganteus* (Accession No. AAE78772; SEQ ID NO:59) and *Penicillium chrysogenum* (Accession No. AAC86132; SEQ ID NO:60) and a protein of unknown function isolated from *Aspergillus niger* (Accession No. CAD66625; SEQ ID NO:61). See U.S. Pat. Nos. 5,747,285, 5,804,184, and 6,271,438 and International Publication No. WO 02/09034, herein incorporated by reference in their entirety. FIG. 1 provides an alignment of the amino acid sequences set forth in SEQ ID NOs:1, 3, 5, 7, 9, 13, and 17 with the *A. giganteus* and *P. chrysogenum* antifungal proteins and the *A. niger* protein of unknown function.

The novel amino acid sequences disclosed comprise the consensus sequence shown in SEQ ID NO:68 (i.e., G-X-C-X-X-X-X-N-X-C-X-Y-X-X-X-X-X-X-X-X-Z-V-X-C-X-X-X-A-N-X-X-C-X-X-D-X-X-X-C-X-X-D-X-X-X-X-X-V-X-C, wherein "X" refers to any one amino acid and "Z" refers to any one amino acid or no amino acid.)

The consensus sequences may be more specifically represented by the sequences set forth in SEQ ID NO:39 (G-X-C-X-X-X-X-N-X-C-X-Y-X-X-X-X-X-X-X-X-X-V-X-C-X-X-X-A-N-X-X-C-X-X-D-X-X-X-C-X-X-D-X-X-X-X-X-V-X-C) or SEQ ID NO:40 (G-X-C-X-X-X-X-N-X-C-X-Y-X-X-X-X-X-X-X-X-X-V-X-C-X-X-X-A-N-X-X-C-X-X-D-X-X-X-C-X-X-D-X-X-X-X-X-V-X-C), wherein "X" refers to any amino acid. This consensus sequence is unique among the known antifungal proteins. The consensus sequence disclosed herein may further comprise the consensus sequence as shown in SEQ ID NO:41 ((K or Q)-(Y or F)-X-G-X-C-X-X-X-X-N-X-C-(T or K)-Y-X-X-X-X-X-X-X-X-V-X-C-(P or G)-(S or T)-(A or F)-A-N-X-(R or K)-C-X-X-D-(R or G)-X-X-C-X-(Y or F)-D-X-(H or Y)-X-X-X-V-X-C-(Q or D)) or SEQ ID NO:42: ((K or Q)-(Y or F)-X-G-X-C-X-X-X-X-N-X-C-(T or K)-Y-X-X-X-X-X-X-X-X-V-X-C-(P or G)-(S or T)-(A or F)-A-N-X-(R or K)-C-X-X-D-(R or G)-X-X-C-X-(Y or F)-D-X-(H or Y)-X-X-X-V-X-C-(Q or D)), wherein "X" refers to any amino acid, and wherein "or" indicates one or the other amino acids (of the two indicated in parentheses) may be substituted at the respective positions.

Alignment data indicate that SEQ ID NO:1 shares approximately 49% sequence identity with the *A. giganteus* antifungal protein and 58% sequence identity with the *P. chrysogenum* antifungal protein. SEQ ID NOs:5 and 7 share approximately 81% and 79% sequence identity with the *A. niger* protein of unknown function, respectively. Overall, the polypeptide sequences of the invention share about 26-45% sequence identity with the *A. giganteus* antifungal protein, about 25-60% sequence identity with the *P. chrysogenum* antifungal protein, and about 26-86% sequence identity with the *A. niger* protein. Tables summarizing the global identity and similarity data are provided in Table 1A and 1B.

The *A. giganteus* antifungal protein causes membrane permeabilization of susceptible fungi and exhibits potent antifungal activity against the phytopathogenic fungi *Magnaporthe grisea* and *Fusarium moniliforme* and the oomycete pathogen *Phytophthora infestans*. See, for example, Vila et al. (2001) *Mol. Plant. Microbe Interact.* 14:1327-31; Theis et al. (2003) *Antimicrob. Agents Chemother.* 47:588-93; and Meyer et al. (2003) *J. Basic Microbiol.* 43:68-74. Moreover, wheat transformed with the *A. giganteus* antifungal protein shows increased fungal resistance to *Erysiphe graminis* and *Puccinia recondite*. See, for example, Oldach et al. (2001) *Mol. Plant. Microbe Interact.* 14:832-8. Similarly, the antifungal protein isolated from *P. chrysogenum* has been shown to cause membrane permeabilization and ion leakage in certain fungi and to inhibit the growth of various filamentous fungi. See, for example, Kaiserer et al. (2003) *Arch. Microbiol.* 180:204-10.

The nucleic acids and polypeptides of the present invention find use in methods for inducing pathogen resistance in a plant. Accordingly, the compositions and methods disclosed herein are useful in protecting plants against fungal pathogens, viruses, nematodes and the like. "Pathogen resistance" or "disease resistance" is intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss. One of skill in the art will appreciate that the compositions and methods disclosed herein can be used with other compositions and methods available in the art for protecting plants from insect and pathogen attack.

"Antipathogenic compositions" or "antipathogenic polypeptides" is intended to mean that the compositions of the invention have antipathogenic activity and thus are capable of suppressing, controlling, and/or killing the invading pathogenic organism. An antipathogenic polypeptide of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens. In particular embodiments, the antipathogenic activity exhibited by the polypeptides of the invention is antifungal activity. As used herein, "antifungal activity" refers to the ability to suppress, control, and/or kill the invading fungal pathogen. Likewise, "fungal resistance" refers to enhanced tolerance to a fungal pathogen when compared to that of an untreated or wild type plant. Resistance may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens may both constitute antifungal activity or improved fungal resistance.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference). Assays that specifically measure antifungal activity are also well known in the art. See, for example, Duvick et al. (1992) *J. Biol. Chem.* 267: 18814-18820; Lacadena et al. (1995) *Arch. Biochem. Biophys.* 324:273-281; Xu et al. (1997) *Plant Mol. Biol.* 34: 949-959; Lee et al. (1999) *Biochem. Biophys. Res. Comm.* 263:646-651; Vila et al. (2001) *Mol. Plant. Microbe Interact.* 14:1327-1331; Moreno et al. (2003) *Phytpathol.* 93:1344-1353; Kaiserer et al. (2003) *Arch. Microbiol.* 180:204-210; and U.S. Pat. No. 6,015,941.

The compositions disclosed herein comprise isolated nucleic acids that encode antipathogenic polypeptides, expression cassettes comprising the nucleotide sequences of the invention, and isolated antipathogenic polypeptides. Antipathogenic compositions comprising a polypeptide of the invention in combination with a carrier are also provided. The invention further discloses plants and microorganisms transformed with nucleic acids that encode antipathogenic proteins. The compositions find use in methods for inducing pathogen resistance in a plant and for protecting a plant from a pathogen, particularly fungal pathogens.

In particular aspects, methods for inducing pathogen resistance in a plant comprise introducing into a plant at least one expression cassette, wherein the expression cassette comprises a nucleotide sequence encoding an antipathogenic polypeptide of the invention operably linked to a promoter that drives expression in the plant. The plant expresses the antipathogenic polypeptide, thereby exposing the pathogen to the polypeptide at the site of pathogen attack. In particular embodiments, the polypeptide has antifungal activity, and the pathogen is a fungus, such as, for example, *Colletotrichum graminicola, Diplodia maydis, Fusarium graminearum*, or *Fusarium verticillioides*. Expression of an antipathogenic polypeptide of the invention may be targeted to specific plant tissues where pathogen resistance is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters. Moreover, the polypeptides of the invention may also be targeted to specific subcellular locations within a plant cell or, alternatively, secreted from the cell, as described herein below.

Just as expression of an antipathogenic polypeptide of the invention may be targeted to specific plant tissues or cell types through the use of appropriate promoters, it may also be targeted to different locations within the cell through the use of targeting information or "targeting labels." Unlike the promoter, which acts at the transcriptional level, such targeting information is part of the initial translation product. Depending on the mode of infection of the pathogen or the metabolic function of the tissue or cell type, the location of the protein in different compartments of the cell may make it more efficacious against a given pathogen or make it interfere less with the functions of the cell. For example, one may produce a protein preceded by a signal peptide, which directs the translation product into the endoplasmic reticulum, by including in the construct (i.e. expression cassette) sequences encoding a signal peptide (such sequences may also be called the "signal sequence"). The signal sequence used could be, for example, one associated with the gene encoding the polypeptide, or it may be taken from another gene. There are many signal peptides described in the literature, and they are largely interchangeable (Raikhel and Chrispeels, "Protein sorting and vesicle traffic" in Buchanan et al., eds, (2000) *Biochemistry and Molecular Biology of Plants* (American Society of Plant Physiologists, Rockville, Md.), herein incorporated by reference). The addition of a signal peptide will result in the translation product entering the endoplasmic reticulum (in the process of which the signal peptide itself is removed from the polypeptide), but the final intracellular location of the protein depends on other factors, which may be manipulated to result in localization most appropriate for the pathogen and cell type. The default pathway, that is, the pathway taken by the polypeptide if no other targeting labels are included, results in secretion of the polypeptide across the cell membrane (Raikhel and Chrispeels, supra) into the apoplast. The apoplast is the region outside the plasma membrane system and includes cell walls, intercellular spaces, and the xylem vessels that form a continuous, permeable system through which water and solutes may move. This will often be a suitable location. In particular embodiments, a nucleotide sequence encoding a barley alpha-amylase signal peptide (SEQ ID NO:34) is joined in frame with a polynucleotide of the invention. See, for example, the nucleotide sequences set forth in SEQ ID NOs:19, 21, 23, 25, 27, 29, and 31.

Other pathogens may be more effectively combated by locating the peptide within the cell rather than outside the cell membrane. This can be accomplished, for example, by adding an endoplasmic reticulum retention signal encoding sequence to the sequence of the gene. Methods and sequences for doing this are described in Raikhel and Chrispeels, supra; for example, adding sequences encoding the amino acids K, D, E and L in that order, or variations thereof described in the literature, to the end of the protein coding portion of the polypeptide will accomplish this. ER retention sequences are well known in the art and include, for example, KDEL (SEQ ID NO:62), SEKDEL (SEQ ID NO:63), HDEL (SEQ ID NO:64), and HDEF (SEQ ID NO:65). See, for example, Denecke et al. (1992). *EMBO J.* 11:2345-2355; Wandelt et al. (1992) *Plant J.* 2:181-192; Denecke et al. (1993) *J. Exp. Bot.* 44:213-221; Vitale et al. (1993) *J. Exp. Bot.* 44:1417-1444; Gomord et al. (1996) *Plant Physiol. Biochem.* 34:165-181; Lehmann et al. (2001) *Plant Physiol.* 127 (2): 436-449.

Alternatively, the use of vacuolar targeting labels such as those described by Raikhel and Chrispeels, supra, in addition to a signal peptide will result in localization of the peptide in a vacuolar structure. As described in Raikhel and Chrispeels, supra, the vacuolar targeting label may be placed in different positions in the construct. Use of a plastid transit peptide encoding sequence instead of a signal peptide encoding sequence will result in localization of the polypeptide in the plastid of the cell type chosen (Raikhel and Chrispeels, supra). Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196: 1414-1421; and Shah et al. (1986) *Science* 233:478-481.

Chloroplast targeting sequences that encode such transit peptides are also known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263:14996-14999).

One could also envision localizing the polypeptide in other cellular compartments by addition of suitable targeting information. (Raikhel and Chrispeels, supra). A useful site available on the world wide web that provides information and references regarding recognition of the various targeting sequences can be found at: psort.nibb.ac.jp/mit. Other references regarding the state of the art of protein targeting include Silva-Filho (2003) *Curr. Opin. Plant Biol.* 6:589-595; Nicchitta (2002) *Curr. Opin. Cell Biol.* 14:412-416; Bruce (2001) *Biochim Biophys Acta* 1541: 2-21; Hadlington & Denecke (2000) *Curr. Opin. Plant Biol.* 3: 461-468; Emanuelsson et al. (2000) *J Mol. Biol.* 300: 1005-1016; Emanuelsson & von Heijne (2001) *Biochim Biophys Acta* 1541: 114-119, herein incorporated by reference.

The compositions of the invention find further use in methods directed to protecting a plant from a pathogen. "Protecting a plant from a pathogen" is intended to mean killing the pathogen or preventing or limiting disease formation on a plant. In some embodiments, an antipathogenic composition comprising an antipathogenic polypeptide and a carrier is applied directly to the environment of a plant pathogen, such as, for example, on a plant or in the soil or other growth medium surrounding the roots of the plant, in order to protect the plant from pathogen attack. Transformed microorganisms comprising a nucleotide sequence encoding an antipathogenic protein of the invention and methods of using them to protect a plant from a pathogen are further provided. In some embodiments, the transformed microorganism is applied directly to a plant or to the soil in which a plant grows.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. "Fragment" is intended to mean a portion of the nucleotide sequence or a portion of the amino acid sequence and hence protein encoded thereby. Fragments of a nucleotide sequence may encode protein fragments that retain the biological activity of the native protein and hence have antipathogenic activity, more particularly antifungal activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the polypeptides of the invention.

A fragment of a nucleotide sequence that encodes a biologically active portion of an antifungal polypeptide of the invention will encode at least 15, 25, 30, 40, or 50 contiguous amino acids, or up to the total number of amino acids present in a full-length antifungal polypeptide of the invention (for example, 55 amino acids for SEQ ID NO:1). Fragments of a nucleotide sequence that are useful as hybridization probes or PCR primers generally need not encode a biologically active portion of an antipathogenic protein.

As used herein, "full-length sequence" in reference to a specified polynucleotide means having the entire nucleic acid sequence of a native sequence. "Native sequence" is intended to mean an endogenous sequence, i.e., a non-engineered sequence found in an organism's genome.

Thus, a fragment of a nucleotide sequence of the invention may encode a biologically active portion of an antipathogenic polypeptide, or it may be a fragment that can be used as a hybridization probe or PCR primer using methods disclosed below. A biologically active portion of an antipathogenic polypeptide can be prepared by isolating a portion of one of the nucleotide sequences of the invention, expressing the encoded portion of the antipathogenic protein (e.g., by recombinant expression in vitro), and assessing the activity of the encoded portion of the antifungal protein. Nucleic acid molecules that are fragments of a nucleotide sequence of the invention comprise at least 15, 20, 50, 75, 100, or 150 contiguous nucleotides, or up to the number of nucleotides present in a full-length nucleotide sequence disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the invention will be constructed such that the open reading frame is maintained. For polynucleotides, conservative variants include those sequences that, because of the degeneracy of the genetic code, encode the amino acid sequence of one of the antipathogenic polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an antipathogenic protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptides of SEQ ID NOs:1, 3, 5, 7, and 9 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, antipathogenic, particularly antifungal, activity as described herein. Such variants may result from, for example, genetic polymorphism or from human manipulation. Biologically active variants of a native antipathogenic protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the antipathogenic proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass naturally occurring proteins as well as variations and modified forms thereof. Such variants will continue to possess the desired antipathogenic, particularly antifungal, activity. Obviously, the mutations that will be made in the DNA encoding the variant must not place the sequence out of reading frame and optimally will not create complementary regions that could produce secondary mRNA structure. See, EP Patent No. 0075444.

In nature, some polypeptides are produced as complex precursors which, in addition to targeting labels such as the signal peptides discussed elsewhere in this application, also contain other fragments of peptides which are removed (processed) at some point during protein maturation, resulting in a mature form of the polypeptide that is different from the primary translation product (aside from the removal of the signal peptide). "Mature protein" refers to a post-translationally processed polypeptide; i.e., one from which any pre- or propeptides present in the primary translation product have been removed. "Precursor protein" or "prepropeptide" or "preproprotein" all refer to the primary product of translation of mRNA; i.e., with pre- and propeptides still present. Pre- and propeptides may include, but are not limited to, intracellular localization signals. "Pre" in this nomenclature generally refers to the signal peptide. The form of the translation product with only the signal peptide removed but no further processing yet is called a "propeptide" or "proprotein." The fragments or segments to be removed may themselves also be referred to as "propeptides." A proprotein or propeptide thus has had the signal peptide removed, but contains propeptides (here referring to propeptide segments) and the portions that will make up the mature protein. The skilled artisan is able to determine, depending on the species in which the proteins are being expressed and the desired intracellular location, if higher expression levels might be obtained by using a gene construct encoding just the mature form of the protein, the mature form with a signal peptide, or the proprotein (i.e., a form including propeptides) with a signal peptide. For optimal expression in plants or fungi, the pre- and propeptide sequences may be needed. The propeptide segments may play a role in aiding correct peptide folding.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that measure antipathogenic activity such as antifungal plate assays. See, for example, Duvick et al. (1992) *J. Biol. Chem.* 267:18841-18820, herein incorporated by reference.

Variant polynucleotides and proteins also encompass sequences and proteins derived from a mutagenic and recombinogenic procedure such as DNA shuffling. With such a procedure, one or more different antipathogenic protein coding sequences can be manipulated to create a new antipathogenic protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the antipathogenic protein gene of the invention and other known antipathogenic protein genes to obtain a new gene coding for a protein with an improved property of interest, such as increased antifungal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272: 336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other microorganism, more particularly other fungi. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for an antipathogenic, particularly antifungal, protein and which hybridize under stringent conditions to the sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique among antipathogenic polynucleotide sequences and are optimally at least about 10 nucleotides in length, and most optimally at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. "Stringent conditions" or "stringent hybridization conditions" is intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138: 267-284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_n$, of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et at (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, and the like.

In some embodiments, expression cassettes comprising a promoter operably linked to a heterologous nucleotide sequence of the invention that encodes an antipathogenic polypeptide are further provided. The expression cassettes of the invention find use in generating transformed plants, plant cells, and microorganisms and in practicing the methods for inducing pathogen resistance disclosed herein. The expression cassette will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antipathogenic polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the invention, a translational termination region and, optionally, a transcriptional termination region functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in The Operon, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

A number of promoters can be used in the practice of the invention, including the native promoter of the polynucleotide sequence of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acids can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theon. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that result in expression of a protein locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant. Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the antipathogenic polypeptides of the invention within a particular plant tissue. For example, a tissue-preferred promoter may be used to express an antifungal polypeptide in a plant tissue where disease resistance is particularly important, such as, for example, the roots or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-referred promoters include, but are not limited to, the *Prunus serotina* prunasin hydrolase gene promoter (see, e.g., International Publication No, WO 03/006651), and also those found in U.S. patent application Ser. No. 10/109,488, issued as U.S. Pat. No. 6,921,815.

Stalk-preferred promoters may be used to drive expression of an antipathogenic polypeptide of the invention. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacte-* rium rhizogenes (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Ciml (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

In certain embodiments the nucleic acid sequences of the present invention can be stacked with any combination of polynucleotide sequences of interest in order to create plants with a desired phenotype. For example, the polynucleotides of the present invention may be stacked with any other polynucleotides of the present invention, such as any combination of SEQ ID NOS: 1, 3, 5, 7, and 9, or with other antifungal genes and the like. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990, 389; 5,885,801; 5,885,802; and 5,703,409); barley high lysine (Williamson et al. (1987) *Eur. J. Biochem.* 165:99-106; and WO 98/20122); and high methionine proteins (Pedersen et at (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001, issued as U.S. Pat. No. 6,858,778); and thioredoxins (U.S. application Ser. No. 10/005,429, filed Dec. 3, 2001, issued as U.S. Pat. No. 7,009,087)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747, 450; 5,737,514; 5723,756; 5,593,881; Geiser et al (1986) *Gene* 48:109); lectins (Van Damme et at (1994) *Plant Mol. Biol.* 24:825); fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J Bacteriol.* 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The methods of the invention involve introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the invention do not depend on a particular method for introducing a sequence into a plant, only that the polynucleotide gains access to the interior of at least one cell of the plant. Methods for introducing polynucleotides into plants are known in the art including, but not limited to, stable transformation methods, transient transformation methods, and virus-mediated methods. Polypeptides can also be introduced to a plant in such a manner that they gain access to the interior of the plant cell or remain external to the cell but in close contact with it.

"Stable transformation" is intended to mean that the nucleotide construct introduced into a plant integrates into the genome of the plant and is capable of being inherited by the progeny thereof "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055-and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the antipathogenic sequences of the invention can be provided to a plant using a variety of transient transformation methods. Such transient transformation methods include, but are not limited to, the introduction of the antipathogenic protein or variants and fragments thereof directly into the plant or the introduction of the antipathogenic protein transcript into the plant. Such methods include, for example, microinjection or particle bombardment. See, for example, Crossway et al. (1986) *Mol. Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it's released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the an antipathogenic polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) *Molecular Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant have stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Pedigree breeding starts with the crossing of two genotypes, such as an elite line of interest and one other elite inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F$_5$, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., increased pathogen resistance), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principals of Cultivar Development" Fehr, 1993 Macmillan Publishing Company the disclosure of which is incorporated herein by reference. In addition, mutations created in other lines may be used to produce a backcross conversion of elite lines that comprises such mutations.

As used herein, the term plant includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used to induce pathogen resistance or protect from pathogen attack any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassaya (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Antipathogenic compositions, particularly antifungal compositions, are also encompassed by the present invention. Antipathogenic compositions may comprise antipathogenic polypeptides or transformed microorganisms comprising a nucleotide sequence that encodes an antipathogenic polypeptide. The antipathogenic compositions of the invention may be applied to the environment of a plant pathogen, as described herein below, thereby protecting a plant from pathogen attack. Moreover, an antipathogenic composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

A gene encoding an antipathogenic, particularly antifungal, polypeptide of the invention may be introduced into any suitable microbial host according to standard methods in the art. For example, microorganism hosts that are known to occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, and to provide for stable maintenance and expression of the gene expressing the antifungal protein.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and *Aureobasidium pollulans*. Of particular interest are the pigmented microorganisms.

Other illustrative prokaryotes, both Gram-negative and gram-positive, include Enterobacteriaceae, such as *Escherichia, Erwinia, Shigella, Salmonella*, and *Proteus*; Bacillaceae; Rhizobiceae, such as *Rhizobium*; Spirillaceae, such as photobacterium, *Zymomonas, Serratia, Aeromonas, Vibrio, Desulfovibrio, Spirillum*; Lactobacillaceae; Pseudomonadaceae, such as *Pseudomonas* and *Acetobacter*; Azotobacteraceae and Nitrobacteraceae. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Saccharomyces cerevisiae, Bacillus thuringiensis, Escherichia coli, Bacillus subtilis*, and the like.

Genes encoding the antifungal proteins of the invention can be introduced into microorganisms that multiply on plants (epiphytes) to deliver antifungal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the antifungal polypeptides of the invention can be introduced into a root-colonizing *Bacillus cereus* by standard methods known in the art.

Genes encoding antifungal proteins can be introduced, for example, into the root-colonizing *Bacillus* by means of electrotransformation. Specifically, genes encoding the antifungal proteins can be cloned into a shuttle vector, for example, pHT3101 (Lerecius et al. (1989) *FEMS Microbiol. Letts.* 60: 211-218. The shuttle vector pHT3101 containing the coding sequence for the particular antifungal protein gene can, for example, be transformed into the root-colonizing *Bacillus* by means of electroporation (Lerecius et al. (1989) *FEMS Microbiol. Letts.* 60: 211-218).

Methods are provided for protecting a plant from a pathogen comprising applying an effective amount of an antipathogenic protein or composition of the invention to the environment of the pathogen. "Effective amount" is intended to mean an amount of a protein or composition sufficient to control a pathogen. The antipathogenic proteins and compositions can be applied to the environment of the pathogen by methods known to those of ordinary skill in the art.

The antifungal compositions of the invention may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaracides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the antipathogenic proteins, more particularly antifungal proteins, of the present invention include, but are not limited to, foliar application, seed coating, and soil application. The number of applications and the rate of application depend on the intensity of infestation by the corresponding pest or pathogen.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthaleneformaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Nonionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The antipathogenic compositions of the present invention can be in a suitable form for direct application or as a concentrate of primary composition that requires dilution with a suitable quantity of water or other diluant before application. The concentration of the antipathogenic polypeptide will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01 lb-5.0 lb. per acre when in dry form and at about 0.01 pts.-10 pts. per acre when in liquid form.

In a further embodiment, the compositions, as well as the transformed microorganisms and antipathogenic proteins, of the invention can be treated prior to formulation to prolong the antipathogenic, particularly antifungal, activity when applied to the environment of a target pathogen as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W.H. Freeman and Co.).

The antipathogenic compositions of the invention can be applied to the environment of a plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pathogens as a protective measure. For example, the antipathogenic protein and/or transformed microorganisms of the invention may be mixed with grain to protect the grain during storage. It is generally important to obtain good control of pathogens in the early stages of plant growth, as this is the time when the plant can be most severely damaged. The compositions of the invention can conveniently contain an insecticide if this is thought necessary. In one embodiment of the invention, the composition is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, an inert carrier, and dead cells of a *Bacillus* strain or transformed microorganism of the invention.

Compositions of the invention find use in protecting plants, seeds, and plant products in a variety of ways. For example, the compositions can be used in a method that involves placing an effective amount of the antipathogenic, more particularly, antifungal, composition in the environment of the pathogen by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protective coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protective coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the invention comprising a DNA molecule comprising a nucleotide sequence encoding an antipathogenic polypeptide of the invention may be treated with a seed protective coating comprising a seed treatment compound, such as, for example, captan, carboxin, thiram, methalaxyl, pirimiphos-methyl, and others that are commonly used in seed treatment. Alternatively, a seed of the invention comprises a seed protective coating comprising an antipathogenic, more particularly antifungal, composition of the invention is used alone or in combination with one of the seed protective coatings customarily used in seed treatment.

The antifungal polypeptides of the invention can be used for any application including coating surfaces to target microbes. In this manner, the target microbes include human pathogens or microorganisms. Surfaces that might be coated with the antifungal polypeptides of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047, herein incorporated by reference.

The embodiments of the present invention may be effective against a variety of plant pathogens, particularly fungal pathogens, such as, for example, *Colletotrichum graminicola, Diplodia maydis, Fusarium graminearum*, and *Fusarium verticillioides*. Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Fungal pathogens, include but are not limited to, *Colletotrichum graminicola, Diplodia maydis, Fusarium graminearum*, and *Fusarium verticillioides*. Specific pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium roseum, Alternaria alternata*; Alfalfa: *Clavibacter michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium alboatrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum, Leptotrichila medicaginis*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondite* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmopora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Colletotrichum graminicola, Fusarium moniliforme* var. *subglutinans, Erwinia stewartii, F. verticillioides, Gibberella zeae* (*Fusarium graminearum*), *Stenocarpella maydi* (*Diplodia maydis*), *Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora, Corn stunt spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, C. sublineolum, Cer-* cospora sorghi, Gloeocercospora sorghi, Ascochyta sorghina, Pseudomonas syringae p.v. syringae, Xanthomonas campestris p.v. holcicola, Pseudomonas andropogonis, Puccinia purpurea, Macrophomina phaseolina, Perconia circinate, Fusarium moniliforme, Alternaria alternate, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghid, Sugarcane mosaic H, Maize Dwarf Mosaic Virus A & B, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola, etc.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The article "a" and "an" are used herein to refer to one or more than one (i.e., to at least one) of the grammatical object of the article. By way of example, "an element" means one or more element.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

The following examples are provided by way of illustration, not by way of limitation.

EXPERIMENTAL

Methods of growing fungal cultures are well known in the art. For subculturing the fungal cultures disclosed herein, any broth generally suitable for growing fungi may be used, including, for example, potato dextrose broth infra (Becton Dickinson Microbiology Systems, Sparks, Md.), Czapek-Dox broth infra (Becton Dickinson Microbiology Systems, Sparks Md.), Sabouraud broth (BBL #210986, Voigt Global Distribution LLC, Kansas City, Mo.), and the like.

Example 1

Isolation of Antifungal Polypeptide LBNL-5220 (SEQ ID NO:1)

An environmental sample was collected from a geothermal mud pool (GPS data: 54°26'256"×160°08'385") located in the Kronotsky National Park in Kamchatka, Russia. The organism, denoted herein as K01-17A5, that produced the antifungal polypeptide LBNL-5220, was isolated from diverse colonies that grew on potato dextrose agar using isolation techniques and media as published earlier (Hunter-Cevera, J. C. and Belt, A. 1999. *Isolation of Cultures, Manual of Industrial Microbiology and Biotechnology*, Chapter 1, pp. 3-20). The molecular-level characterization, based on whole-cell fatty acid methyl ester (FAME) analysis and on sequencing of the D1/D2 domains of the large subunit ribosomal RNA-coding genes, was confirmed by classical phenotype-based identification. The strain was identified as the ascomycetous fungus *Penicillium simplicissimum* (Oudemans) Thom (syn. *P. janthinellum* Biourge).

A designed set of specific growth conditions, i.e., nutrient content, temperature, pH, incubation time, aeration, etc., were applied to the isolated fungus to promote the production of secondary metabolites and novel natural products. Biomass and supernatant of the resulting microbial fermentation were then separated by centrifugation. The cell-free supernatant LBNL-5220 was assayed to determine the presence of heat labile antifungal activity. After confirming that heat labile antifungal activity was present in the LBNL-5220 supernatant, the cell-free supernatant of a large scale, 500-ml culture was provided and subjected to solid phase extraction, as described below.

Oasis HLB extraction cartridges (6 gram, 35 mL) (Waters Corporation, Milford, Mass.) were used for solid phase extraction (SPE). Specifically, the SPE cartridge was made wet with one cartridge volume of methanol and then conditioned with approximately 40 mL Solvent A (2% acetonitrile, 0.1% TFA). The extract was treated with 5× solvent A to a final concentration of 1× and centrifuged for 20 min at 3,000× g. The supernatant was loaded onto an SPE cartridge, and the SPE cartridge was washed with approximately 40 mL solvent A. The SPE cartridge was eluted with approximately 40 mL 90% acetonitrile, 0.1% TFA. The eluted sample was partially dried in a centrifugal evaporator (Speed Vac) and frozen with liquid nitrogen and lyophilized to dryness.

The dried extract was re-suspended in deionized $H_2O$ (0.5 mL:12.5 mL starting culture filtrate), and the re-suspended extract was enriched for proteins using a Sephadex G10 (Amersham Biosciences AB, Uppsala, Sweden) spin column. Bio-Spin disposable chromatography columns (Bio-Rad Laboratories, Hercules Calif.) were filled to approximately 0.75 mL bed volume with Sephadex G10 that had been pre-equilibrated in phosphate buffered saline (PBS) and were centrifuged for 1 minute at 1,000×g. 10×PBS was added to the SPE extract to a final concentration of 1×PBS. 200 µA of SPE extract in PBS was added to each pre-spun Bio-Spin column, and loaded Bio-Spin columns were centrtifuged for 5 minutes at 1,000×g to elute proteins.

Sephadex G-10 treated extracts were tested for antifungal activity against FVE, CGR, FGR, and DMA using an antifungal plate assay, as described in Example 3. Assays were performed in ½ area 96 well clear bottom plates. FVE, FGR and DMA were tested at 4,000 spores/mL in ¼× potato dextrose broth (Becton Dickinson Microbiology Systems, Sparks, Md.). CGR was tested at 4,000 spores/mL in ¼× Czapek-Dox (Becton Dickinson Microbiology Systems, Sparks Md.)+180 mL/L V8 juice. Cultures were allowed to develop at 27° C. for 24 hours. Assays were scored by visualizing fungal growth with an inverted microscope.

Antifungal extracts were fractionated by HPLC with a Jupiter 5µ C5 300 Å 150×4.6 mm column (Phenomenex, Torrance, Calif.). HPLC starting conditions were 5% acetonitrile, 0.05% heptafluorobutyric acid (HFBA), 0.4 mL/minute. Following injection, the flow rate was raised to 0.8 mL/minute over 1 minute. After an additional minute, a 94 minute exponentially curved gradient (Waters gradient curve 7, Waters Corporation, Milford, Mass.) was started to 86% acetonitrile, 0.05% HFBA. 30 second fractions were collected into ½ area 96 well clear bottom assay plates. Plates containing fractionated extracts were then dried in a centrifugal evaporator. The dried fractionated extracts were then screened for antifungal activity as described above. The HPLC fractions from approximately 64 to 66 minutes were found to have antifungal activity against FVE, CGR, FGR and DMA.

Additional HPLC fractionations were performed to bulk up the antifungal fraction. This bulked up antifungal fraction was further purified using μ-bore HPLC with a Zorbax 3.5μ C8 300 Å 150×1.0 mm column (Agilent Technologies, Palo Alto, Calif.). Starting conditions were 5% acetonitrile, 0.1% trifluoroacetic acid (TFA), 50 μL/minute. Following sample injection a 40 minute linear gradient was started to 23% acetonitrile, 0.1% TFA. Fractions were collected manually, dried in a centrifugal evaporator and assayed for antifungal activity as described above. A peak eluting at approximately 27 minutes was found to have broad spectrum activity against FVE, CGR, FGR and DMA. ESI mass spectra were obtained on a Finnigan LCQ mass spectrometer by directly infusing the purified sample at 1 μL/minute.

Reduction and alkylation was required for efficient N-terminal sequencing. Approximately 10 μg dried protein was re-suspended into 18 μL 0.1 M ammonium bicarbonate, 8 M urea pH 8.3. This solution was transferred to limited volume HPLC autosampler vial. 1 μL 200 mM DTT was added and the solution was incubated at 50° C. for 1 hour. Subsequently, 1 μL 500 mM iodoacetamide was added, and the solution was incubated at 37° C. for 30 minutes in the dark. The iodoacetamide alkylation was then quenched by adding 2 μL 25% trifluoroacetic acid. The alkylated protein was purified by g-bore HPLC on a Vydac C4 150×1.0 mm column. A 100 minute linear gradient was performed from 5% acetonitrile, 0.1% TFA to 95% acetonitrile 0.1% TFA. The column flow rate was 50 μL/minute.

N-terminal Sequencing

The full elucidation of the sequence set forth in SEQ ID NO:1 by N-terminal sequencing required sequencing of Asp-N (Calbiochem) digested LBNL-5220 fragments. 5 μL (0.2 μg) Asp-N was added to approximately 10 μg LBNL-5220 that was dissolved in 15 μL 50 mM sodium phosphate 0.5 M urea pH 7.5. This solution was incubated for approximately 14 hours at 37° C. The digested fragments were purified by g-bore HPLC with a Zorbax 3.5μ C8 300 Å 150×1.0 mm column (Agilent Technologies, Palo Alto, Calif.). Starting conditions were 5% acetonitrile, 0.1% trifluoroacetic acid (TFA), 50 μL/minute. Following sample injection a 100 minute linear gradient was started to 95% acetonitrile, 0.1% TFA.

Example 2

Isolation of Antifungal Polypeptides LBNL-5197/8-1 and LBNL-5197/8-2 (SEQ ID NOs:3 and 5) and LBNL-09827 (SEQ ID NOs:7 and 9)

The two distinct strains of another organism, denoted herein as K01-17A2 and K01-17A4, that produced the antifungal polypeptides LBNL-5197/8-1 and LBNL-5197/8-2 (SEQ ID NOs:3 and 5), respectively, were isolated from an environmental sample that was collected as in Example 1. The organisms were selected from diverse colonies that grew on potato dextrose agar. The molecular-level characterization of the strains, based on whole-cell fatty acid methyl ester (FAME) analysis and on sequencing of the D1/D2 domains of the large subunit ribosomal RNA-coding genes, was confirmed by classical phenotype-based identification. The two organisms were identified as strains of the ascomycetous fungus *Penicillium miczyinskii* Zaleski (syn. *P. soppi* Zaleski).

A designed set of specific growth conditions, i.e., nutrient content, temperature, pH, incubation time, aeration, etc., were applied to the isolated fungi to promote the production of secondary metabolites and novel natural products. Biomass and supernatants of the resulting microbial fermentations were then separated by centrifugation. The cell-free supernatants LBNL-5197 (K01-17A2) and LBNL-5198 (K01-17A4) were assayed to determine the presence of heat labile antifungal activity. After confirming that heat labile antifungal activity was present in the LBNL-5197 (K01-17A2) and LBNL-5198 (K01-17A4) supernatants, the cell-free supernatants of a large scale, 500-ml cultures were provided and subjected to solid phase extraction, as described in Example 1.

Another fungal organism of interest, IMV 00127, that produced the antifungal polypeptides LBNL-9827-1 and LBNL-9827-2 (SEQ ID NOs:7 and 9), was isolated on potato dextrose agar (PDA) from an apparently contaminated fodder grain sample that was collected in the Kharkov region, Ukraine. The pure culture of the organism was previously maintained at the D. K. Zabolotny Institute of Microbiology and Virology, Kiev, Ukraine, at room temperature on malt extract agar slant by sub-culturing it in regular intervals. The strain IMV 00127 was identified as *Monascus ruber* by employing classical fungal taxonomic methods and molecular-level techniques, such as fatty acid methyl ester (FAME) analysis and sequencing of the D1/D2 domain of the large subunit rRNA-coding gene.

A designed set of specific growth conditions, i.e., nutrient content, temperature, pH, incubation time, aeration, etc., were applied to the isolated fungus to promote the production of secondary metabolites and novel natural products. Biomass and supernatant of the resulting microbial fermentation was then separated by centrifugation. The cell-free supernatant LBNL-9827 was assayed to determine the presence of heat labile antifungal activity. After confirming that heat labile antifungal activity was present in the LBNL-9827 supernatant, the cell-free supernatant of a large scale, 500-ml culture was provided and subjected to solid phase extraction, as described in Example 1.

Antifungal extracts were fractionated by HPLC as described in Example 1, and antifungal activity against FVE, CGR, FGR and DMA was found in the 62-68 minute HPLC fractions.

Additional HPLC fractionations were performed to bulk up the antifungal fraction as described in Example 1. Two peaks containing anti-FVE activity were identified which eluted at approximately 23 (i.e., SEQ ID NO:3) and 31 minutes (i.e., SEQ ID NO:5), respectively. ESI mass spectra were obtained on a Finnigan LCQ mass spectrometer by directly infusing the purified sample at 1 μL/minute.

Reduction and alkylation was performed to prepare samples for efficient N-terminal sequencing as described in Example 1. The alkylated protein was purified by g-bore HPLC on a Zorbax 3.5μ C8 300 Å 150×1.0 mm column (Agilent Technologies, Palo Alto, Calif.). Starting conditions were 5% acetonitrile, 0.1% trifluoroacetic acid (TFA), 50 μL/minute. 10 minutes after sample injection a 50 minute linear gradient was started to 95% acetonitrile, 0.1% TFA.

N-terminal Sequencing of SEQ ID NO:3

Further elucidation of the Peak #1 sequence (SEQ ID NO:3) by N-terminal sequencing required sequencing digested Peak #1 fragments. Asp-N was used to prepare digested fragments for sequencing. 5 µL 0.2 µg Asp-N was added to approximately 10 µg Peak #1 that was dissolved in 15 µL 50 mM sodium phosphate 0.5 M urea pH 7.5. This solution was incubated for about 14 hours at 37° C. The digested fragments were purified by g-bore HPLC with a Zorbax 3.5µ C8 300 Å 150×1.0 mm column (Agilent Technologies, Palo Alto, Calif.). Starting conditions were 5% acetonitrile, 0.1% trifluoroacetic acid (TFA), 50 µL/minute. Following sample injection a 100 minute linear gradient was started to 95% acetonitrile, 0.1% TFA.

Example 3

Antifungal Activity Assays

The antifungal activity of the polypeptides of the invention against the fungal pathogens *Fusarium verticillioides* (FVE), *Colletotrichum graminicola* (CGR), *Fusarium graminearum* (FGR) and *Diplodia maydis* (DMA) was assessed using a standard plate assay. Silica gel stocks of each fungus were stored at −20° C. prior to use.

Preparation of Cultures for Spore Production:
Cultures of FVE were prepared using V8 agar plates. FGR, CRG, and DMA cultures were prepared using ½× oatmeal agar. Media recipes are provided below. Specifically, tubes containing silica-gel fungal stocks stored at −20° C. were briefly flamed, and approximately 5 crystals were sprinkled onto the agar surface. 2-3 plates of each fungal isolate were prepared. The newly plated cultures were stored in a plastic box in the dark at room temperature to prevent the cultures from drying out. New cultures were prepared every other week to maintain a consistent supply of spores.

Spore Preparation:
Spores were prepared from 2-4 week old cultures of FVE, FGR, CGR, and DMA. For FGR, FVE, and DMA, a portion of the culture plate was rinsed with a small amount of assay medium. The rinse solution was permitted to remain on the DMA plates for a time sufficient to allow the pycnidia rupture. The assay medium was then transferred to a sterile tube. Samples were vortexed, and spores were quantitated using a hemacytometer.

For CGR, a sterile loop was gently dragged across orange areas of the culture plate. The loop was then inserted into a small volume of assay media, and the media was mixed with the loop to suspend the spores. Samples were vortexed, and spores were quantitated using a hemacytometer.

Spores were diluted to the desired concentration with assay medium (4,000 spores per mL for FGR, FVE, and CGR, and 6,000 spores per mL for DMA) and kept on ice prior to beginning the antifungal activity assay.

Assay Plate Preparation Details:
Standard non-tissue culture treated 96 well flat bottom plates or ½ area non-treated plates (Costar) were used in the antifungal plate assays. Assay medium was ¼× potato dextrose broth for FVE, FGR and DMA, and ¼×Czapec-Dox V8 was used for CGR.

Antifungal polypeptides at various concentrations were added to the plates at 50 µL/well for a standard assay plate or 25 µL/well for a half area plate. An equal volume of media with fungal spores at 2 times the above concentrations was then added to start the assay. Alternatively HPLC fractionated lead samples were assayed by adding media with fungal spores (as above) into assay plates that the HPLC samples had been dried into (Savant Speed-vac). The plates were sealed with a gas permeable membrane ("Breathe-Easy", Cat. No. BEM-1, Diversified Biotech, Boston, Mass.), and the assay was allowed to develop in the dark at 28° C. for 24 to 48 hours.

After the incubation period, the plates were placed on an inverted microscope, and each well was examined and scored on a scale of 0-4, according to the following parameters: 0=no inhibition of fungal growth when compared to the negative control, 0.5=slight inhibition (overall growth is less than the negative control but growth from individual spores is not distinct), 1=slight inhibition (overall growth is less than the negative control but growth from individual spores is apparent, albeit not quite confluent), 2=moderate inhibition (growth from 1 spore can easily be identified and is significantly less abundant than the negative control; growth from each spore tends to look spherical), 3=strong inhibition (spores have germinated but growth is limited to a few branches of short hyphae), 4=complete inhibition (spores have not germinated. See, for example, Duvick et al. (1992) *J. Biol. Chem.* 267: 18814-18820). A score sheet containing representative examples of each level of antifungal activity is provided in FIG. 3.

Figure 4:
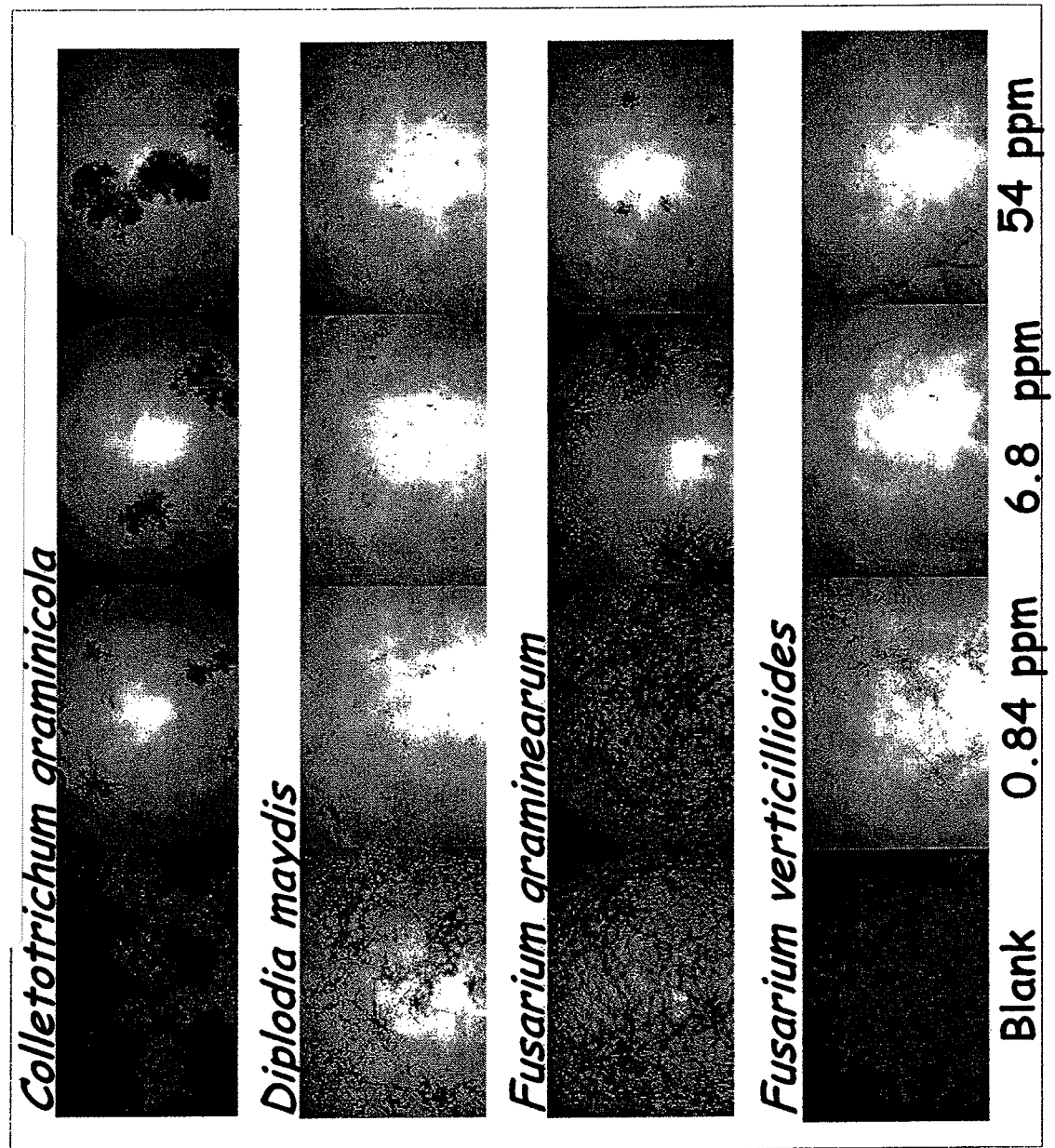
FIG. 4 provides the photographic results of antifungal activity assays performed with the polypeptide set forth in SEQ ID NO:1, as described in Example 3. Antifungal activity against *Colletotrichum graminicola*, *Diplodia maydis*, *Fusarium graminearum*, and *Fusarium verticillioides* was observed.

Results
FIG. 4 provides the photographic results of antifungal activity assays with the polypeptide set forth in SEQ ID NO:1. This polypeptide showed antifungal activity against FVE, FGR, CGR, and DMA.

Figure 5:
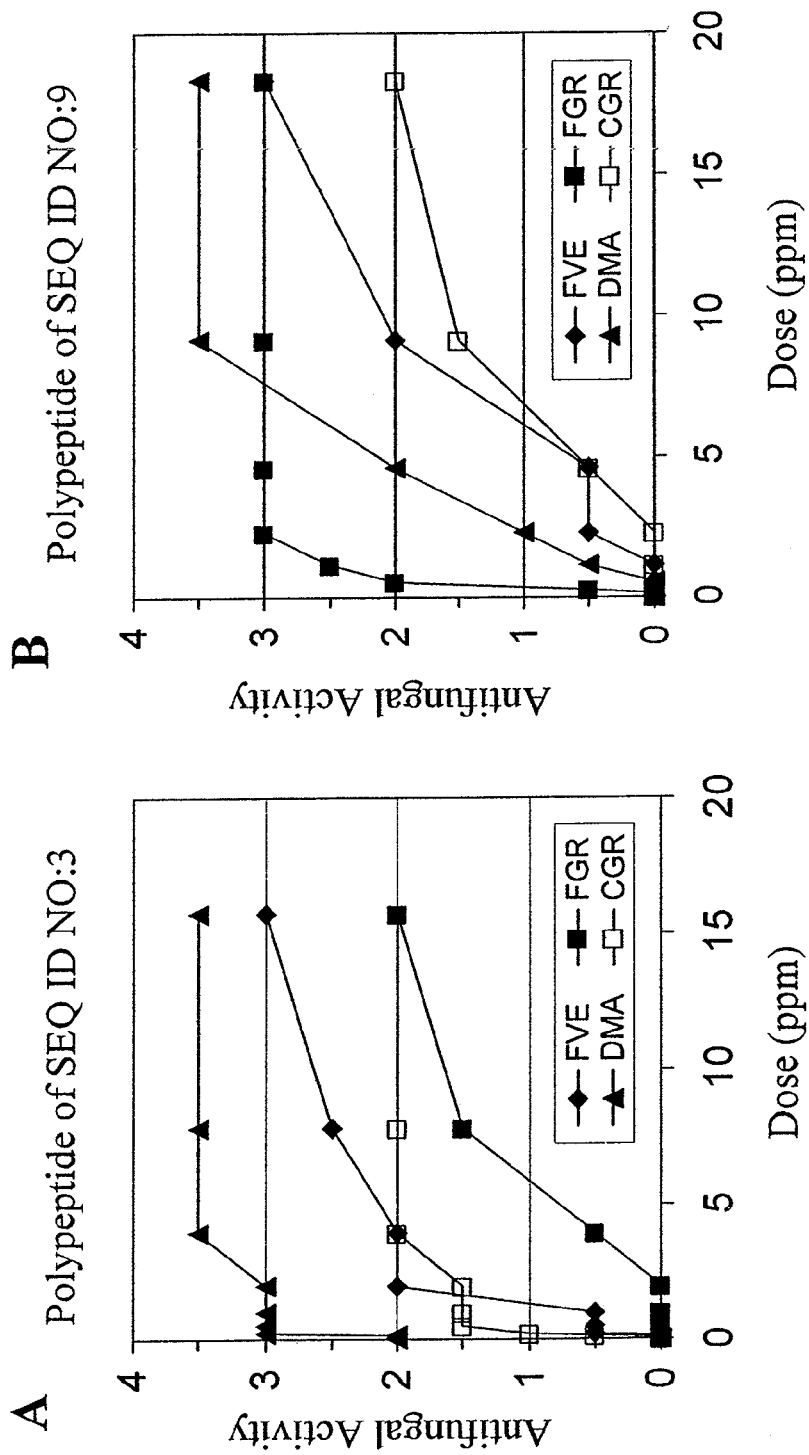
FIGS. 5A and 5B show the results of antifungal activity assays performed with the polypeptides set forth in SEQ ID NO:3 and SEQ ID NO:9, respectively. Both polypeptides inhibited *Colletotrichum graminicola*, *Diplodia maydis*, *Fusarium graminearum*, and *Fusarium verticillioides* in a dose-dependent fashion. Experimental details are provided in Example 3.

FIGS. 5A and 5B provide the antifungal activity profiles obtained in assays with the polypeptides set forth in SEQ ID NO:3 and SEQ ID NO:9, respectively. Both polypeptides inhibited FVE, FGR, CGR, and DMA in a dose-dependent fashion.

HPLC purified LBNL-9827-1 polypeptide (SEQ ID NO:7) was also tested in antifungal assays against FVE. The results of these experiments indicated that this polypeptide is active against FVE (data not shown). Notably, SEQ ID NO:7 is identical to SEQ ID NO:9 except that SEQ ID NO:9 comprises 3 additional N-terminal amino acids.

Media Recipes:
1× Czapek-Dox V8 Broth:
For each liter, suspend 35 grams Difco Czapek-Dox Broth (#233810) in $dH_2O$ and add 180 milliliters V8 juice that has been clarified by centrifugation (3,000×g is plenty). Raise final volume to 1 liter and autoclave at 121° C. for 20 minutes. The media is filter sterilized to remove any remaining debris.

1× Potato Dextrose Broth:
For each liter, suspend 24 grams Difco Potato Dextrose Broth (#0549-17-9) in $dH_2O$ and raise final volume to 1 liter and autoclave at 121° C. for 20 minutes. The media is filter sterilized to remove any remaining debris.

CCM (*Cochliobolus* Complete Medium):
Solution A: 10 grams $Ca(NO_3)_2.4H_2O$ per 100 mL
Solution B: 2 grams $KH_2PO_4$+1.5 grams NaCl per 100 mL. Adjust pH to 5.3 with NaOH Solution C, 2.5 grams $MgSO_4.7H_2O$ per 100 mL Put 900 mL $dH_2O$ into vessel on stir plate. Add to the water in order and allow each component to dissolve before proceeding to the next step:
10 mL solution A
10 mL solution B
10 mL solution C
10 grams glucose
1 gram Difco yeast extract
0.5 gram casein hydrolysate (acid)
0.5 gram casein hydrolysate (enzyme)

Bring final volume to 1 liter and filter sterilize, but do not autoclave. ¼×CCM-phosphate is made by diluting the 1×CCM medium to ¼× with 10 mM sodium phosphate buffer pH 5.8

V8 Agar:

For each liter, dissolve 180 mL V8 juice and 3 grams calcium carbonate in 820 mL deionized water and then add 17 grams Bacto-agar in dH$_2$O in a 4 liter vessel. 10 drops of 5% antifoam A may be optionally added per liter prepared. Cover and autoclave at 121° C. for 20 minutes. Pour plates in sterile hood.

Oatmeal Agar:

For each liter, suspend 36.24 grams of Difco Oatmeal Agar (#0552-17-3) and 4.25 grams agar in dH$_2$O in a 4 liter vessel, cover and autoclave at 121° C. for 20 minutes. Pour plates in sterile hood.

|  | FVE | FGR | CGR | DMA |
|---|---|---|---|---|
| Isolate name | MO33 | 73B ISU | Carroll-IA-99 | Warren-IN-96 |
| Medium for sporulation | V8 Agar | 1/2X Oatmeal Agar | 1/2X Oatmeal Agar | 1/2X Oatmeal Agar |
| Agar culture age range for in vitro assay | 2-4 weeks old | 2-4 weeks old | 2-4 weeks old | 2-4 weeks old |
| Suggested schedule for starting agar cultures | Every other week | Every other week | Every other week | Every other week |
| Liquid medium for in vitro assay | ¼ × potato dextrose broth | ¼ × potato dextrose broth | ¼ × Czapec-Dox V8 broth | ¼ × potato dextrose broth |
| Spore Density for in vitro assay (spores/mL) | 4,000 | 4,000 | 4,000 | 6,000 |

Example 4

Identification of SEQ ID NO: 11 and 15 from a Computer Homology Search

Gene identities can be determined by conducting BLAST (Basic Local Alignment Search Tool; Altschul, S. F., et al. (1993) *J. Mol. Biol.* 215:403-410; see also www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases).

The polynucleotide sequences of the invention (i.e. SEQ ID NOs: 1, 3, 5, 7 and 9) were analyzed for similarity to all publicly available DNA sequences contained in the "nr" database using the BLASTN algorithm. The DNA sequences were translated in all reading frames and compared for similarity to all publicly available protein sequences contained in the "nr" database using the BLASTX algorithm (Gish, W. and States, D. J. *Nature Genetics* 3:266-272 (1993)) provided by the NCBI.

Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method are KTUPLE 1, GAP PENALTY=3, WINDOW=5 and DIAGONALS SAVED=5.

SEQ ID NO: 11 was identified from a proprietary Pioneer database and was concluded to originate from an unspecified fungi endemic to maize (corn) plants. The sequence was found to be related to those sequences already identified from testing of the microbial fermentation broths and shown to have antifungal activity (i.e. SEQ ID NOs:1, 3, 5, 7 and 9). SEQ ID NO: 11 is clearly a member of the same family of antifungal proteins.

SEQ ID NO: 15 was identified from a public sequence database, however, the gene was not specifically identified in the available sequence; that is, the ORF was not predicted nor annotated by the public domain. We found and identified the gene and its ORF encoding a peptide sequence, which was clearly related to the other known, tested sequences of the invention. The identified sequence (SEQ ID NO: 15) clearly belongs to the same family of antifungal proteins.

Example 5

Sequence Analysis of Antifungal Polypeptides

FIG. 1 shows an alignment of the amino acid sequences set forth in SEQ ID NOs:1, 3, 5, 7, and 9 with various known polypeptides sharing sequence similarity with the antipathogenic polypeptides of the invention. Moreover, tables summarizing the global identity and similarity data are presented in Table 1A and Table 1B. Percent identity and similarity values were calculated using GAP with all default parameters, except that penalizing end gaps parameter was selected. See FIG. 2 for alignment limited to the novel sequences disclosed herein.

TABLE 1A

Global Identity Table

|  | *A. gignateus* AFP (SEQ ID NO: 59) | *A. niger_* unknown (SEQ ID NO: 61) | Fg_contig196 (SEQ ID NO: 17) | LBNL-5197-8-1 (SEQ ID NO: 3) | LBNL-5197-8-2 (SEQ ID NO: 5) | LBNL-9827-1 (SEQ ID NO: 7) | LBNL 9827-2 (SEQ ID NO: 9) | *P. chrysogenum* AFP (SEQ ID NO: 60) | Unk_cds 2f.pk001.l8 (SEQ ID NO: 13) |
|---|---|---|---|---|---|---|---|---|---|
| LBNL-05220 (SEQ ID NO: 1) | 49.02 | 35.19 | 52.73 | 48.15 | 40.74 | 35.18 | 33.33 | 58.19 | 35.19 |
| *A. giganteus* AFP (SEQ ID NO: 59) | — | 31.37 | 45.10 | 52.00 | 35.29 | 35.29 | 35.29 | 48.08 | 31.37 |
| A. niger_unknown (SEQ ID NO: 61) | — | — | 33.33 | 38.60 | 81.03 | 79.31 | 79.31 | 36.36 | 87.93 |
| Fg_contig196 (SEQ ID NO: 17) | — | — | — | 44.44 | 35.19 | 35.19 | 33.33 | 61.82 | 35.19 |

TABLE 1A-continued

Global Identity Table

| | A. gignateus AFP (SEQ ID NO: 59) | A. niger_unknown (SEQ ID NO: 61) | Fg_contig196 (SEQ ID NO: 17) | LBNL-5197-8-1 (SEQ ID NO: 3) | LBNL-5197-8-2 (SEQ ID NO: 5) | LBNL-9827-1 (SEQ ID NO: 7) | LBNL 9827-2 (SEQ ID NO: 9) | P. chrysogenum AFP (SEQ ID NO: 60) | Unk_cds 2f.pk001.l8 (SEQ ID NO: 13) |
|---|---|---|---|---|---|---|---|---|---|
| LBNL-5197-8-1 (SEQ ID NO: 3) | — | — | — | — | 36.84 | 38.60 | 40.35 | 57.41 | 42.11 |
| LBNL-5197-8-2 (SEQ ID NO: 5) | — | — | — | — | — | 84.48 | 84.48 | 38.18 | 82.76 |
| LBNL-9827-1 (SEQ ID NO: 7) | — | — | — | — | — | — | 100.00 | 36.36 | 81.03 |
| LBNL-9827-2 (SEQ ID NO: 9) | — | — | — | — | — | — | — | 36.36 | 81.03 |
| P. chrysogenum AFP (SEQ ID NO: 60) | — | — | — | — | — | — | — | — | 38.18 |

TABLE 1B

Global Similarity Table

| | A. gignateus AFP (SEQ ID NO: 59) | A. niger_unknown (SEQ ID NO: 61) | Fg_contig196 (SEQ ID NO: 17) | LBNL-5197-8-1 (SEQ ID NO: 3) | LBNL-5197-8-2 (SEQ ID NO: 5) | LBNL-9827-1 (SEQ ID NO: 7) | LBNL 9827-2 (SEQ ID NO: 9) | P. chrysogenum AFP (SEQ ID NO: 60) | Unk_cds 2f.pk001.l8 (SEQ ID NO: 13) |
|---|---|---|---|---|---|---|---|---|---|
| LBNL-05220 (SEQ ID NO: 1) | 52.94 | 46.29 | 60.00 | 55.56 | 48.15 | 44.44 | 42.59 | 67.27 | 46.30 |
| A. giganteus AFP (SEQ ID NO: 59) | — | 39.22 | 50.98 | 58.00 | 41.18 | 45.10 | 45.10 | 50.00 | 41.18 |
| A. niger_unknown (SEQ ID NO: 61) | — | — | 40.74 | 45.61 | 86.21 | 86.21 | 86.21 | 43.64 | 93.10 |
| Fg_contig196 (SEQ ID NO: 17) | — | — | — | 51.85 | 38.89 | 38.89 | 37.04 | 61.82 | 40.74 |
| LBNL-5197-8-1 (SEQ ID NO: 3) | — | — | — | — | 40.35 | 45.61 | 47.37 | 61.11 | 47.37 |
| LBNL-5197-8-2 (SEQ ID NO: 5) | — | — | — | — | — | 89.66 | 89.66 | 41.82 | 86.21 |
| LBNL-9827-1 (SEQ ID NO: 7) | — | — | — | — | — | — | 100.00 | 41.82 | 86.21 |
| LBNL-9827-2 (SEQ ID NO: 9) | — | — | — | — | — | — | — | 41.82 | 86.21 |
| P. chrysogenum AFP (SEQ ID NO: 60) | — | — | — | — | — | — | — | — | 45.46 |

In particular, analysis of the amino acid sequences disclosed herein revealed that SEQ ID NO:1 shares 48.2% sequence identity and 55.6% sequence similarity with SEQ ID NO:3; 40.7% sequence identity and 48.2% sequence similarity with SEQ ID NO:5; 35.2% sequence identity and 44.4% sequence similarity with SEQ ID NO:7; and 33.3% sequence identity and 42.6% sequence similarity with SEQ ID NO:9. SEQ ID NO:3 shares 36.8% sequence identity and 40.4% sequence similarity with SEQ ID NO:5; 38.6% sequence identity and 45.6% sequence similarity with SEQ ID NO:7; and 40.4% sequence identity and 47.4% sequence similarity with SEQ ID NO:9. SEQ ID NO:5 shares 84.5% sequence identity with both SEQ ID NOs:7 and 9, and shares 89.7% similarity with both SEQ ID NOs: 7 and 9.

Of particular interest was the relationship of the amino acid sequences of SEQ ID NOs:7 and 9. These two polypeptides share 100% sequence identity over a stretch of 58 amino acid residues. The two sequences differ only in that SEQ ID NO:9 has 3 additional amino acids on the N-terminal portion of the polypeptide. LBNL-9827-1 (SEQ ID NO:7) and LBNL-9827-2 (SEQ ID NO:9) are believed to be encoded by the same gene but result from differences in post-transcriptional processing. Notably, both of these polypeptides display antifungal activity, as described in Example 3.

Example 6

Isolation of LBNL-5197/8-1 Gene

For isolation of the LBNL-5197/8-1 gene, a number of degenerate primers were designed to the peptide sequence. These were on each DNA sample (DL1 to DL4) with the appropriate GenomeWalker primers in two rounds of PCR. The primer combination that produced a fragment of the LBNL-5197/8-1 gene and how this PCR was performed are described below:

In the first round PCR, the Clontech AP1 primer (sequence 5'-GTAATACGACTCACTATAGGGC-3') (SEQ ID NO:43) and gene specific primer (gsp) 12R (sequence 5'-RTCR-TANGTRCAYTTRTTNCCRTCYTTYTC-3') (SEQ ID NO:44) were used. PCR was performed in a model PTC-100 thermal cycler with HotBonnet from MJ Research (Watertown, Me.) using reagents supplied with the GenomeWalker kit. The following cycling parameters were used: seven cycles of 94° C. for 2 sec, then 65° C. for 3 min, followed by 28 cycles of 94° C. for 2 sec, and 45° C. for 3 min. Finally, the samples were held at 45° C. for 7 min, then at 4° C. until further analysis.

As described in the GenomeWalker User Manual, the DNA from the first round of PCR was then diluted and served as a template in a second round of PCR using the Clontech AP2 primer (sequence 5'-ACTATAGGGCACGCGTGGT-3') (SEQ ID NO:45) and gsp10R (sequence 5'-NGGRCAYTT-NACRAARTGNGT-3') (SEQ ID NO:46). The cycling parameters for the second round were: 5 cycles of 94° C. for 2 sec, then 65° C. for 3 min, followed by 20 cycles of 94° C. for 2 sec, and 45° C. for 3 min and finally 7 min at 45° C. About 8 µL of each reaction were run on a 1.0% agarose gel, and bands were excised and purified with the QIAquick gel extraction kit, Qiagen, Inc. (Valencia, Calif.) and cloned into the pCR-Blunt vector (Invitrogen, San Diego, Calif.). Clones were sequenced for verification.

A fragment containing 124 by of the LBNL-5197/8-1 gene (sequence 5'-AGGACTATAGGGCACGCGTGGTCGACG-GCTCGGGCTGGTTAATTACTTGTTC CAGAAATGT-TATACAAATGGCAACAATTGTAAGTAC-GATAGTGATGGGAAGA CCCATTTCGTCAAATGTCCC-3') (SEQ ID NO:47) was obtained from DL-2 template using the primer combinations above. This 124 by corresponds to the amino acid sequence in bold, below, from the mature amino acid sequence of LBNL-5197/8-1 and 55 by of the first intron:

IQYTG^KCYTNGNNCKYDSDGKTHFVKCPSAANTK^CEKDGNKCTYDS

YNGKVKCDFRH (SEQ ID NO: 3; bold sequence SEQ ID

NO: 48)

In order to obtain complete gene sequence, additional, nondegenerate or "bona-fide" GenomeWalker primers were designed from the 124 by sequence running in both the forward and reverse directions. First round PCR was carried out with forward primer phn76125 (sequence 5'-TGGTTAAT-TACTTGTTCCAGAAA-3') (SEQ ID NO:49) or reverse primer phn76128 (sequence 5'-CCCATCACTATCGTACT-TACAAT-3') (SEQ ID NO:50) and the Clontech AP1 primer using DL1-4 as template. Second round PCR was performed using the Clontech AP2 primer either forward primer phn76127 (sequence 5'-AAATGGCAACAATTGTAAG-TACG-3') (SEQ ID NO:51) or reverse primer phn76129 (sequence 5'-GTATAACATTTCTGGAACAAGTAAT-3') (SEQ ID NO:52) from diluted products of the first round reactions. If a forward primer was used in the first round, then the internal forward primer was used on that diluted template for the second round, the same being true for how the reverse primers were used. Cycling conditions for both rounds of PCR were the same as used for cloning the 124 by fragment. Band purification and cloning were as described above.

124 by gene fragment (SEQ ID NO:47) and placement of "bona fide" primers:

```
                                                          phn76129
AGGACTATAGGGCACGCGTGGTCGACGGCTCGGGCTGGTTAATTACTTGTTCCAGAAATGTTAT
                                         phn76125 phn76128
ACAAATGGCAACAATTGTAAGTACGATAGTGATGGGAAGACCCATTTCGTCAAATGTCCC
      phn76127
```

Notably, the first 3 bases, AGG, may be from the cloning vector.

The 5' portion of the 5197/8-1 gene was obtained using the reverse primer pair and DL-2 as template:

>R2-8, 432 bp.
(SEQ ID NO: 53)
CTATAGGGCACGCGTGGTCGACGGCCCGGGCTGGTCTGAACATCTTCG

ACTATGTAATAATAGCCCTTATTAGGCTCAATAATCTTTCGGTAACGG

CCCCCATGATGACTGCGTCGAAAATGGTGATCATGCTTGTCACATCTT

CTACAGGGATCATGATAACTCCTATATAAGACAGCCCCTCGGAACATT

TGATCCATCTTCCCAATCGTCTCGACCAACGATTCAAGCCATTCACCA

TGCAGATTGCCAATATTTCGCTTTTCCTTTTCGCTGCCATGGGTACGA

TTGCTAGTCCCCTTGATGCCGAGTCCGACGACCTCAGTGCTAGAGACG

TGAATGCTGCCGACATTCAGTACACCGGA[GTGAGATTATTACAGCAC

ATGCAGACATGAGAACGAAGCTAATTACTTGTTCCAG]AAATGTTATA

CC (Exonic Regions in Italics, Intronic in Brackets; Predicted Start Codon in Bold Type.)

The 3' half of the 5197/8-1 gene and downstream sequences were obtained using the forward primer pair and DL-1 template:

>F1-3, 960 bp.
(SEQ ID NO: 54)
AATGGCAACAATTGTAAGTACGATAGTGATGGGAAGACGCACTTTGTC

AAGTGCCCTAGCGCCGCCAACACAAA[GGTATCTTTCCTTTATAATTA

AGCATATTGACCTCGACTAACCTTGATCATTAACTTTCGAG]TGCGAG

AAGGACGGAAATAAGTGCACATATGACTCCTACAACGGAAAGGTCAAG

-continued

```
TGCGACTTCCGCCATAATTAAGCTATTTCAAACGGCTGTTCCTGGCC

ATTCTTCTTACCAGCAAGTGTGAGATGCCATGTGATTCTCAGTGCCTA

CAATTCGTGTCAAGAAAGGCTAGGAACAAGCAGTATTGAATATGTGTT

GGGTGAATACATATGTGATGTCCATCCCCAGTATCTCGCTCTTCTGTG

ATTTTTGCTATGACCCCACTCGTTTATTATCTAGCTAGATACTTTTGC

TTATCAATATTTTTGCTCATCAATAAATTGCTCATTGACTGCCTGATG

TTTTGAGCATCTCTGTGAATCAGACAATATCCTAGTCATCTATGTATT

GCTAAGTCATGCTAGTAGCCTGACACTCTGGTAGCTACCAACTTCTCA

ACGAATCTGACCGGAAGGATTCTCTCCGGCAGTTTGAACAATCCGAAA

GTTTGACAATTACCAGAACCTCAGAACATATATATTTCTATCTGGTGC

ATGTAAGGGGTGTAATCATTTCTTATTTGTATACCTTAGAAGATATAG

CGGACGTGCGAAGGGCTGCATTGAGAGAAAAGAGAAACATTGAACTCG

GAAGCCAAAGTAGGAGAGAAGCTAAGAAAGAAGGAGAGAGATCTGATG

GACTTCTTTCTTGAAAACTGCTTTCGGGCCTTCCTTCACGTCTTACTT

AATTTGCGCCATCCTTTGAGTCATCCTTCAAGTCTTCATTTCCCGTAG

CCTCACTCTTTACCAGCCCGGGCCGTCGACCACGCGTGCCCTATAGT

CCT
```

(Exonic regions in italics, intronic in brackets; stop codon in bold, putative polyadenylation signal underlined.)
Based on the DNA sequence the full-length peptide has the sequence (SEQ ID NO:55):

M<u>QIANISLFLFAAMGTIA</u>SPLDAESDDLSARDVNAAD

*IQYTG^KCYTNGNNCKYDSDGKTHFVKCPSAANTK^CEKDGNKCTYDS*

*YNGKVKCDFRH*

Underlined letters: predicted signal sequence
Bold letters: propeptide sequence
Italic letters: mature peptide
^: position of intron in corresponding genomic sequence.

In order to clone the LBNL-5197/8-1 gene as a single molecule, PCR was performed on LBNL-5197 genomic DNA using phn76685 (sequence 5'-AATTGCGGCCGCATGCAGATTGCCAATATTTCGCTTTTCC-3'; the site for the restriction enzyme NotI underlined) (SEQ ID NO:56) and phn76686 (sequence 5'-TATATGGATCCTTAATGGCGGAAGTCGCACTTGACCTTTC-3'; the site for the restriction enzyme BamHI underlined) (SEQ ID NO:57). PCR was run in an MJ PTC100 with HotBonnet using the Advantage-HF2 PCR kit (BD BioSciences) with the following cycling conditions: 94° C. for 30 sec, followed by 35 cycles of 94° C. for 15 sec, 54° C. for 30 sec, 74° C. for 1.5 min, after which the reactions were incubated at 74° C. for an additional 2 min, then held at 4° C. until further analysis. Bands were purified as described above, cut with BamHI and NotI, gel-purified again, and then cloned into an in-house vector for sequence verification. The genomic sequence for LBNL-5197/8-1 is set forth in SEQ ID NO:58.

The gene encoding the full-length peptide sequences for LBNL-9827-1 and LBNL-9827-2 was similarly isolated by Genome Walker experiments. The *M. ruber* genomic sequence encoding full-length LBNL-9827-1 and LBNL-9827-2 is set forth in SEQ ID NO:66. The full-length polypeptide encoded by SEQ ID NO:66, including a predicted signal peptide and a pro-peptide region, is set forth in SEQ ID NO:67.

Example 7

Preparation of Expression Constructs

A T-DNA expression construct was made for maize transformation via *Agrobacterium tumefaciens* to achieve high levels of constitutive extracellular accumulation of the peptide of SEQ ID NO:1 (LBNL-5220 mature peptide). The promoter in this case was the maize ubiquitin promoter and first intron (UBI) fused downstream to the 35S enhancer element (an enhancer element derived from the cauliflower mosaic virus 35S enhancer, SEQ ID NO:33). This promoter was upstream of the nucleotide sequence (SEQ ID NO:34) encoding the barley alpha-amylase signal peptide (SEQ ID NO:35). This signal peptide-encoding sequence was in-frame upstream of the artificial nucleotide sequence of SEQ ID NO:2 encoding the amino acid of SEQ ID NO:1. The polyadenylation signal was from potato proteinase inhibitor II (PI-NII). The resulting fusion was engineered into a T-DNA expression vector (designated PHP22300) for maize transformation via *Agrobacterium tumefaciens*.

In order to achieve pathogen-inducible accumulation of the peptide with SEQ ID NO: 1 inside the lumen of the endoplasmic reticulum in maize, a different T-DNA expression vector was designed. The promoter of ZmPR1-81 (SEQ ID NO:36; U.S. Pat. No. 6,429,362) was linked to the nucleotide sequence encoding the barley alpha-amylase signal peptide (SEQ ID NO: 34) and was in-frame upstream of the artificial nucleotide sequence of SEQ ID NO:37, which encodes the LBNL-5220 mature peptide with a COOH-terminal KDEL (SEQ ID NO:38). The polyadenylation signal was from potato proteinase inhibitor II (PINII). The resulting fusion was engineered into a T-DNA expression vector (designated PHP22300-PR1) for maize transformation via *Agrobacterium tumefaciens*.

The PHP22300 construct contained the BAR gene for herbicide-based selection of transformed tissues on solid media. Immature embryos of genotype GS3 were transformed with the PHP22300 construct via *Agrobacterium* co-cultivation, and stably-transformed callus was obtained by continuing herbicide selection on solid medium.

The PHP22300-PR1 construct contained the BAR gene for herbicide-based selection of transformed tissues on solid media. Immature embryos of genotype GS3 are transformed with the PHP22300-PR1 construct via *Agrobacterium* co-cultivation, and stably-transformed callus is obtained by continuing herbicide selection on solid medium.

Example 8

*Fusarium verticillioides* Challenge Assay of Maize Seedlings Expressing Antifungal Polypeptide LBNL-5220 (SEQ ID NO:1)

Maize seedlings transformed with the PHP22300 construct described above in Example 7 comprising a nucleotide sequence encoding the antifungal polypeptide designated LBNL-5220 (SEQ ID NO:1) operably linked to the ubiquitin promoter were exposed to a suspension of spores of a transgenic *F. verticillioides* line that expresses the reporter gene β-glucuronidase (GUS). After three days, explant tissue was harvested and analyzed for levels of GUS activity. GUS activity correlates with fungal biomass and, therefore, is indicative of seedling resistance to fungal infection. That is, the lower the GUS activity, the less fungus present on the seedling tissue, and the more resistant the maize seedling is to the fungus.

Figure 6:
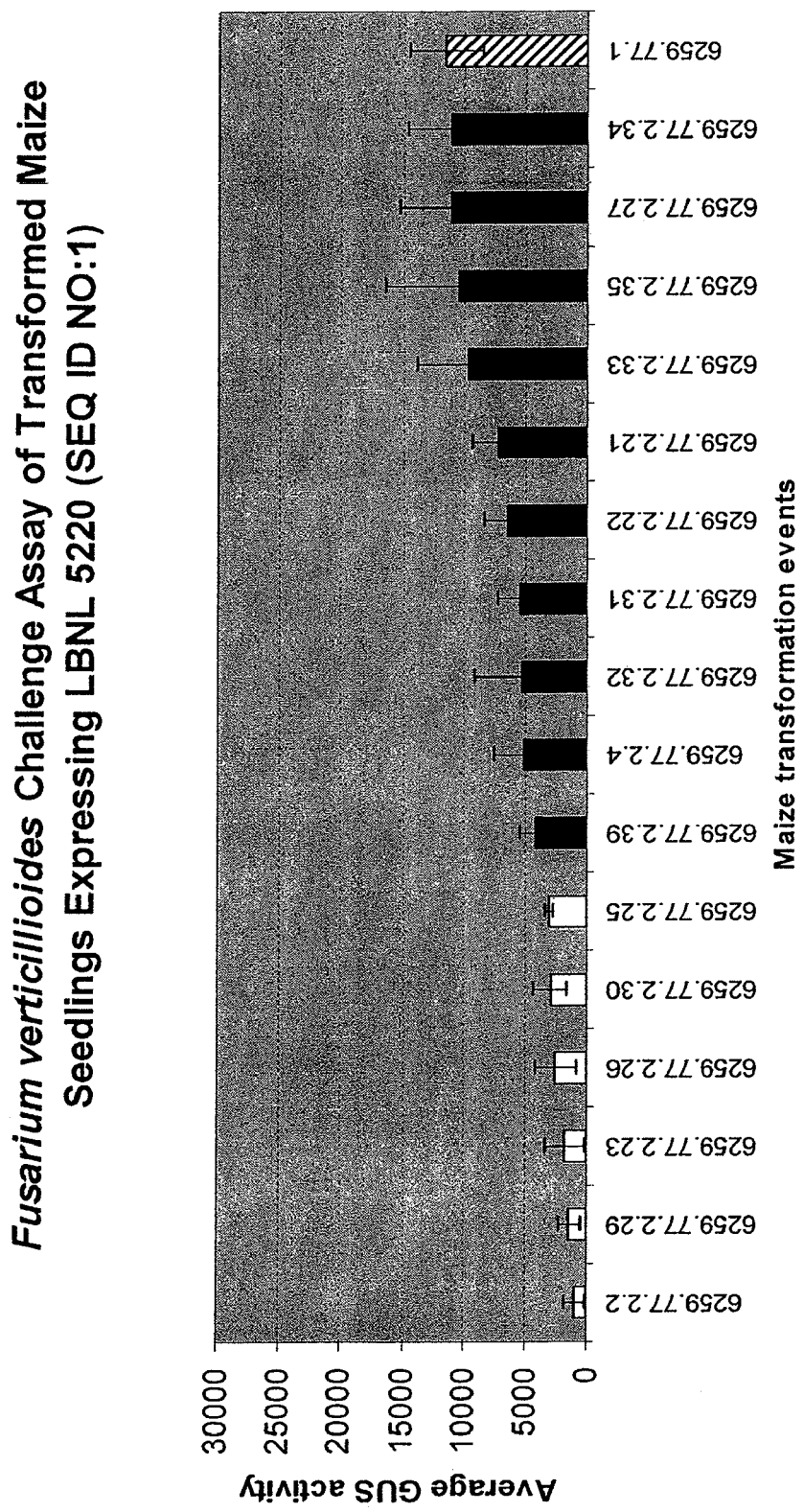
FIG. 6 provides the results of a *Fusarium verticillioides* challenge assay of maize seedlings expressing the antifungal polypeptide designated LBNL-5220 (SEQ ID NO:1). Experimental details are provided in Example 8. Results obtained with negative control seedlings transformed with an empty vector control plasmid are presented as a hatched bar. White bars represent results from maize seedlings transformed with the LBNL-5220 construct in which a statistically significant difference (at the 95% confidence level) in GUS activity relative to that of control samples was observed. Transformation events in which decreases in GUS activity relative to controls were not statistically significant (at the 95% confidence level) are presented as black bars.
Figure 8:
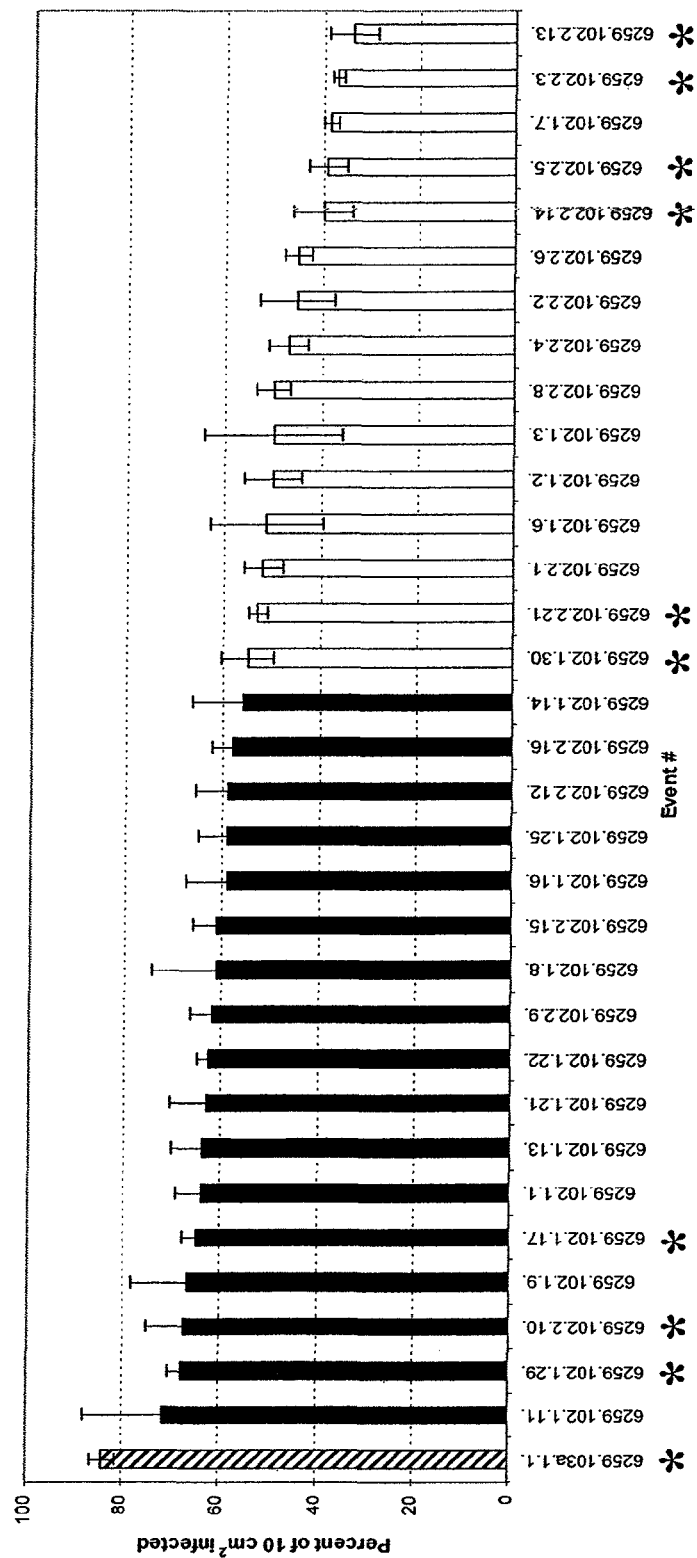
FIG. 8 provides the results of *Colletotrichum graminicola* resistance assays of transgenic LBNL-5220 (SEQ ID NO:1) maize plants. Experimental details are provided in Example 10. Results obtained with negative controls (i.e., empty vector control events) are presented as a hatched bar. Results obtained in upper stalk internodes of transformation events marked with white bars were statistically more resistant to infection by *C. graminicola* than negative control stalks. Transformation events in which a statistically significant improvement in fungal resistance was not observed are presented as black bars.
Figure 9:
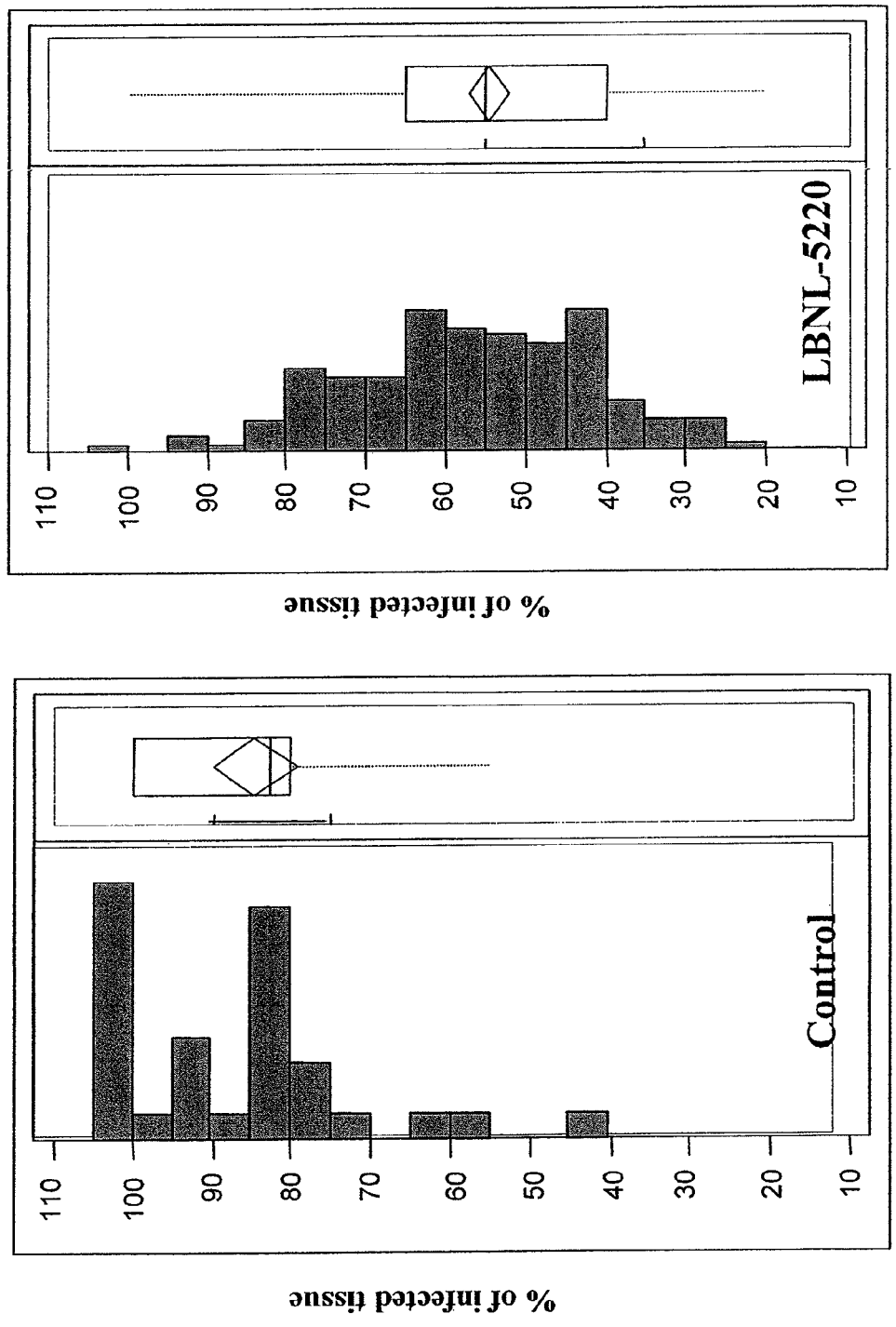
FIG. 9 provides the distribution of upper stalk *C. graminicola* resistance scores for control and LBNL-5220 transgenic maize plants. Experimental details are provided in Example 10.

The results of the *F. verticilioides* challenge assay are summarized in FIG. 6. The X-axis represents different maize transformation events. Average GUS enzyme activity levels (+/− standard error of the mean) for 4 explants per maize transformation event are shown on the Y-axis. Results obtained with negative control seedlings transformed with an empty vector control plasmid are presented as a hatched bar. A decrease in average GUS activity in maize seedlings transformed with PHP22300 to express antifungal polypeptide LBNL-5220 (SEQ ID NO:1) relative to controls was observed with all maize transformation events, to varying degrees. White bars represent transformation events in which a statistically significant difference (at the 95% confidence level) in GUS activity relative to that of control samples was observed. Transformation events in which decreases in GUS activity relative to controls were not statistically significant (at the 95% confidence level) are presented as black bars.

Example 9

Accumulation and Antifungal Activity of LBNL-5220 (SEQ ID NO:1) in Transgenic Maize Callus Accumulation of LBNL-5220—Western Blot Analysis GS3 genotype maize embryos were transformed with the PHP22300 construct described above. Embryos were cultured to permit transgenic callus growth. 200 mg of selected callus events were homogenized in 400 μL NuPage LDS sample treatment buffer (Invitrogen). 2.5 μL heat-treated supernatant (equivalent to ~1.25 mg tissue) was loaded per lane of a polyacrylamide gel. Electrophoresis was performed with NuPage 4-12% Bis-Tris polyacrylamide gels (Invitrogen) in MES running buffer. Western analysis was performed using monoclonal antibodies directed to the antifungal polypeptide LBNL-5220. The LBNL-5220 antibodies were previously generated in genetically immunized mice. Some of the transformation events appeared to accumulate near 30 μg LBNL-5220/g fresh weight (western blot data not shown).

Accumulation of LBNL-5220 in Transgenic Maize Callus Extracts—LC-MS (ESI-TOF) Analysis Accumulation of functional LBNL-5220 in transgenic maize callus was also assessed using LC-MS (ESI-TOF) analysis of callus extracts.

Callus Extraction Method 200 mg of callus sample was mixed with 1.5 mL PBS and disrupted with a bead beater (3 3/16" bead beater) for 2 minutes. The samples were centrifuged, and 1.3 mL of the supernatant transferred. The supernatants were brought to 2% acetonitrile and 0.1% TFA. The samples were applied to a conditioned 60 mg Oasis HLB SPE cartridge. The cartridge was washed with 2% acetonitrile/0.1% TFA. The protein was eluted with 95% acetonitrile/0.1% TFA and dried in a speed-vac. Samples were then resuspended in 50 μL of water, and 10 μL (corresponding to 35 mg fresh weight equivalent) injected on to the LC-MS (0.3 mm×100 mm Zorbax 300SB C8).

Results

A peak corresponding to a parent peptide of mass 6174 Da, the mass of the mature LBNL-5220 antifungal protein, was identified (data not shown). These results confirm that the chimeric barley alpha amylase signal peptide/LBNL-5220 construct is correctly expressed and cleaved in maize tissue to release the mature LBNL-5220 protein.

Assay of Antifungal Activity of LBNL-5220 Antifungal Polypeptide Isolated from Transgenic Maize Callus Transgenic maize callus extracts were prepared using the extraction method described above with the exception that the final extract was resuspended in 100 μL ¼×PBS. Extracts were assayed and scored for antifungal activity against *Fusarium verticillioides* (FVE) essentially as described in Example 3.

Results

The results of the antifungal activity assays are summarized below in Table 2 and in FIG. 7. Scoring guidelines are provided in Example 3. The results indicate that LBNL-5220 protein produced and isolated from transgenic maize callus has antifungal activity.

TABLE 2

30 Hour FVE Antifungal Activity Score of Transgenic Maize Callus Extracts

| Relative Concentration | Blank | Control Callus | LB-5220 Callus |
|---|---|---|---|
| 1* | 0 | 2 | 3.5 |
| ½ | 0 | 0 | 3 |
| ¼ | 0 | 0 | 3.5 |
| ⅛ | 0 | 0 | 3.5 |
| 1/16 | 0 | 0 | 3.5 |
| 1/32 | 0 | 0 | 3.5 |
| 1/64 | 0 | 0 | 3 |
| 1/128 | 0 | 0 | 3 |

*Relative concentration "1" = extract from 240 mg callus/100 μL

Example 10

Accumulation of LBNL-5220 in T0 Generation Transgenic Maize Plants—Western Blot Analysis and Fungal Resistance of Transgenic Maize Plants EFWWETX genotype maize embryos were transformed with PHP22300, as described herein. Embryos were cultured to permit regeneration of transgenic maize plants. Accumulation of LBNL-5220 in leaf and upper stalk samples was assessed by western blot, and resistance of the transgenic maize plants to *Colletotrichum graminicola* was assayed, as described below.

Western Blot Analysis

Leaf Samples

Four leaf punches were taken from each plant at the ~V7 stage. Specifically, two leaf punches were taken from each of a leaf above and below an inoculated leaf and pooled. Leaf punches were homogenized in 200 μL LDS sample treatment buffer, and 50 μL of supernatant from each event member was pooled. 20 μL supernatant (equivalent to ~5 mg fresh weight equivalents) was loaded per lane of a polyacrylamide gel. Electrophoresis was performed with NuPage 4-12% Bis-Tris polyacrylamide gels (Invitrogen) in MES running buffer. Western analysis was performed as before using monoclonal antibodies directed to the antifungal polypeptide LBNL-5220.

Upper Stalk Samples

Upper stalk samples were taken approximately 10 days after pollination (DAP). 1.5 cm of node and internode immediately below the inoculated uppermost internode was taken. Samples were lyophilized, homogenized, and pooled (10 mg DW from each of 4 event members). Samples were extracted with 400 μL LDS sample treatment buffer, and 20 μL (equivalent to 2 mg DW or ~6 mg FW equivalents) was loaded per lane. To assess the variability of LBNL-5220 levels between members of the same transformation events, 5 mg DW of lyophilized stalk powder from each even member was extracted with 200 µL LDS sample treatment buffer, and 10 µL (0.25 mg DW or ~0.8 mg FW equivalents) was loaded per lane. Electrophoresis and western blot analysis were performed for pooled and non-pooled samples as before.

Results

All PHP22300 events accumulated LBNL-5220 antifungal polypeptide (data not shown). The western results indicate that leaf tissue accumulated approximately 2 µg of LBNL-5220/g FW, whereas upper stalk tissue accumulated greater than 20 µg of LBNL-5220/g DW. Variability in LBNL-5220 accumulation levels between members of the same transgenic event was observed (data not shown).

Resistance of Transgenic Maize Plants Expressing LBNL-5220 to *Colletotrichum graminicola*

Upper Stalk Resistance

The uppermost stalk internode immediately below the tassel of T0 generation transgenic maize plants were inoculated with *C. graminicola*. After approximately five days, the stalks were scored for fungal resistance by measuring the percent of infected tissue in a 10 $cm^2$ area centered around the inoculation site.

The mean percent infected area for control plants was 84.7±2.6% and 54.4±1.4% for LBNL-5220 plants. The results of the fungal resistance assays are presented in FIG. 8. Upper stalk internodes of transgenic events represented by white bars were statistically more resistant to *C. graminicola* infection than stalks from the empty vector control event (hatched bar; Dunnett's $p<0.01$). Asterisks mark the events that were used for the western blot analysis described above. The tissue used for westerns was collected on the same day the inoculated internodes were scored for disease resistance. The distribution of upper stalk *C. graminicola* resistance scores for control and LBNL-5220 plants are presented in FIG. 9.

Lower Stalk Resistance

The lowest internode of TO generation transgenic plants was inoculated with a *C. graminicola* spore suspension 10 DAP. After 21 days, the stalks were split, and the number of internodes showing more than 75% disease was counted. Only the five lowermost internodes were analyzed.

The mean score for LBNL-5220 plants was 2.2±0.1 compared with 4.0±0.2 for empty vector control plants. The distribution of lower stalk *C. graminicola* resistance scores for control and LBNL-5220 plants are presented in FIG. 10.

Example 11

Transient Expression of LBNL-5220 (SEQ ID NO:1) in *Nicotiana benthamiana* Leaves Leaves of *Nicotiana benthamiana* were either mock treated or infiltrated with *Agrobacterium* comprising one of the following expression constructs, using standard methods known in the art:

Prepro-LBNL-5220 (SEQ ID NO:69)—encodes the prepropeptide region of the genomic sequence for LBNL-5197/8-1 (SEQ ID NO:58) linked to the mature LBNL-5220 peptide. The prepropeptide region comprises the signal peptide and the propeptide region from the full-length LBNL-5197/8-1 protein (see SEQ ID NO:55).

BAA-Pro-LBNL-5220 (SEQ ID NO:70)—encodes the barley-alpha amylase signal peptide linked to the propeptide region of the genomic sequence for LBNL-5197/8-1 (SEQ ID NO:58) further linked to the mature LBNL-5220 peptide.

BAA-LBNL-5220 (SEQ ID NO:19)—encodes the barley-alpha amylase signal peptide linked to the mature LBNL-5220 peptide.

All expression constructs contained the Mirabilis mosaic caulimovirus promoter (SEQ ID NO:71) followed by an A-rich leader sequence (SEQ ID NO:72) that has been shown to increase transient expression in *N. benthamiana*. The nucleotide sequences for the vectors containing the Prepro-LBNL-5220, BAA-Pro-LBNL-5220, and BAA-LBNL-5220 constructs are set forth in SEQ ID NOs:73, 74, and 75, respectively.

Several days after infiltration, leaf tissue was harvested. Electrophoresis and western blot analysis of control and LBNL-5220 leaf tissue extract samples were performed as before. Western analysis indicated that LBNL-5220 mature peptide accumulates in *N. benthamiana* leaves expressing BAA-Pro-LBNL-5220 or BAA-LBNL-5220. The propeptide region of LBNL-5197/8-1 appeared to be recognized in tobacco leaves and cleaved from the mature LBNL-5220 mature peptide. LC-MS analysis further confirmed that LBNL-5220 accumulated in *N. benthamiana* leaves expressing BAA-Pro-LBNL-5220 or BAA-LBNL-5220.

Example 12

Transformation and Regeneration of Transgenic Maize Plants

Immature maize embryos from greenhouse donor plants are bombarded with a plasmid containing a nucleotide sequence encoding the antipathogenic polypeptide set forth in SEQ ID NO:1 operably linked to a promoter that drives expression in a maize plant cell and a selectable marker (e.g., the selectable marker gene PAT (Wohlleben et al. (1988) *Gene* 70:25-37), which confers resistance to the herbicide Bialaphos). Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a nucleotide sequence encoding the antipathogenic polypeptide set forth in SEQ ID NO:1 operably linked to a promoter that drives expression in a maize cell is made. This plasmid DNA plus plasmid DNA containing a selectable marker (e.g., PAT) is precipitated onto 1.1 μm (average diameter) tungsten pellets using a $CaCl_2$ precipitation procedure as follows:

100 μL prepared tungsten particles in water

10 μL (1 μg) DNA in Tris EDTA buffer (1 μg total DNA)

100 μL 2.5 M $CaCl_2$

10 μL 0.1 M spermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for fungal resistance.

Bombardment and Culture Media

Bombardment medium (560Y) comprises 4.0 g/L N6 basal salts (SIGMA C-1416), 1.0 mL/L Eriksson's Vitamin Mix (1000×SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000×SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos(both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I $H_2O$) (Murashige and Skoog (1962) Physiol. Plant. 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I $H_2O$); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I $H_2O$), 0.1 g/L myo-inositol, and 40.0 g/L sucrose (brought to volume with polished D-I $H_2O$ after adjusting pH to 5.6); and 6 g/L bacto-agar (added after bringing to volume with polished D-I $H_2O$), sterilized and cooled to 60° C.

Example 13

Agrobacterium-mediated Transformation of Maize and Regeneration of Transgenic Plants For *Agrobacterium*-mediated transformation of maize with the polynucleotide construct of Example 7, the method of Zhao was employed (U.S. Pat. No. 5,981,840, and PCT patent publication WO98/32326; the contents of which are hereby incorporated by reference). Briefly, immature embryos were isolated from maize and the embryos contacted with a suspension of *Agrobacterium*, where the bacteria are capable of transferring the polynucleotide construct to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step was performed. In this resting step, the embryos were incubated in the presence of at least one antibiotic known to inhibit the growth of *Agrobacterium* without the addition of a selective agent for plant transformants (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus was recovered (step 4: the selection step). The immature embryos were cultured on solid medium with a selective agent resulting in the selective growth of transformed cells. The callus was then regenerated into plants (step 5: the regeneration step), and calli grown on selective medium were cultured on solid medium to regenerate the plants.

Example 14

Transformation of Somatic Soybean Embryo Cultures and Regeneration of Soybean Plants The following stock solutions and media are used for transformation and regeneration of soybean plants:

Stock Solutions

Sulfate 100× Stock: 37.0 g $MgSO_4.7H_2O$, 1.69 g $MnSO_4.H_2O$, 0.86 g $ZnSO_4.7H_2O$, 0.0025 g $CuSO_4.5H_2O$.

Halides 100× Stock: 30.0 g $CaCl_2.2H_2O$, 0.083 g KI, 0.0025 g $CoCl_2.6H_2O$,

P, B, Mo 100× Stock: 18.5 g $KH_2PO_4$, 0.62 g $H_3BO_3$, 0.025 g $Na_2MoO_4.2H_2O$ Fe EDTA 100× Stock: 3.724 g $Na_2EDTA$, 2.784 g $FeSO_4.7H_2O$.

2,4-D Stock: 10 mg/mL.

Vitamin B5 1000× Stock: 10.0 g myo-inositol, 0.10 g nicotinic acid, 0.10 g pyridoxine HCl, 1 g thiamine.

Media (per Liter)

SB196: 10 mL of each of the above stock solutions, 1 mL B5 vitamin stock, 0.463 g $(NH_4)_2 SO_4$, 2.83 g $KNO_3$, 1 mL 2,4-D stock, 1 g asparagine, 10 g sucrose, pH 5.7.

SB103: 1 pk. Murashige & Skoog salts mixture, 1 mL B5 vitamin stock, 750 mg $MgCl_2$ hexahydrate, 60 g maltose, 2 g gelrite, pH 5.7.

SB166: SB103 supplemented with 5 g per liter activated charcoal.

SB71-4: Gamborg's B5 salts (Gibco-BRL catalog No. 21153-028), 1 mL B5 vitamin stock, 30 g sucrose, 5 g TC agar, pH 5.7.

Soybean embryogenic suspension cultures are maintained in 35 mL liquid medium (SB196) on a rotary shaker (150 rpm) at 28° C. with fluorescent lights providing a 16 hour day/8 hour night cycle. Cultures are subcultured every 2 weeks by inoculating approximately 35 mg of tissue into 35 mL of fresh liquid media.

Soybean embryogenic suspension cultures are transformed by the method of particle gun bombardment (see Klein et al. (1987) *Nature* 327:70-73) using a DuPont Biolistic PDS1000/He instrument.

In particle gun bombardment procedures it is possible to use purified 1) entire plasmid DNA or, 2) DNA fragments containing only the recombinant DNA expression cassette(s) of interest. For every eight bombardment transformations, 30 µl of suspension is prepared containing 1 to 90 picograms (pg) of DNA fragment per base pair of DNA fragment. The recombinant DNA plasmid or fragment used to express the antifungal gene is on a separate recombinant DNA plasmid or fragment from the selectable marker gene. Both recombinant DNA plasmids or fragments are co-precipitated onto gold particles as follows. The DNAs in suspension are added to 50 µL of a 20-60 mg/mL 0.6 µm gold particle suspension and then combined with 50 µL CaCl$_2$ (2.5 M) and 20 µL spermidine (0.1 M) The mixture is pulse vortexed 5 times, spun in a microfuge for 10 seconds, and the supernatant removed. The DNA-coated particles are then washed once with 150 µL of 100% ethanol, pulse vortexed and spun in a microfuge again, and resuspended in 85 µL of anhydrous ethanol. Five µL of the DNA-coated gold particles are then loaded on each macrocarrier disk.

Approximately 150 to 250 mg of two-week-old suspension culture is placed in an empty 60 mm×15 mm petri plate and the residual liquid is removed from the tissue using a pipette. The tissue is placed about 3.5 inches away from the retaining screen and each plate of tissue is bombarded once. Membrane rupture pressure is set at 650 psi and the chamber is evacuated to −28 inches of Hg. Eighteen plates are bombarded, and, following bombardment, the tissue from each plate is divided between two flasks, placed back into liquid media, and cultured as described above.

Seven days after bombardment, the liquid medium is exchanged with fresh SB196 medium supplemented with 50 mg/mL hygromycin or 100 ng/mL chlorsulfuron, depending on the selectable marker gene used in transformation. The selective medium is refreshed weekly or biweekly. Seven weeks post-bombardment, green, transformed tissue is observed growing from untransformed, necrotic embryogenic clusters. Isolated green tissue is removed and inoculated into individual flasks to generate new, clonally-propagated, transformed embryogenic suspension cultures. Thus, each new line is treated as independent transformation event. These suspensions can then be maintained as suspensions of embryos clustered in an immature developmental stage through subculture or can be regenerated into whole plants by maturation and germination of individual somatic embryos.

Transformed embryogenic clusters are removed from liquid culture and placed on solid agar medium (SB166) containing no hormones or antibiotics for one week. Embryos are cultured at 26° C. with mixed fluorescent and incandescent lights on a 16 hour day:8 hour night schedule. After one week, the cultures are then transferred to SB103 medium and maintained in the same growth conditions for 3 additional weeks. Prior to transfer from liquid culture to solid medium, tissue from selected lines is assayed by PCR or Southern analysis for the presence of the antifungal gene.

Somatic embryos become suitable for germination after 4 weeks and are then removed from the maturation medium and dried in empty petri dishes for 1 to 5 days. The dried embryos are then planted in SB71-4 medium where they are allowed to germinate under the same light and germination conditions described above. Germinated embryos are transferred to sterile soil and grown to maturity.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule that encodes a polypeptide having antifungal activity wherein said nucleic acid molecule is selected from the group consisting of:
   (a) a nucleic acid molecule comprising the nucleotide sequence set forth in SEQ ID NO: 2, 4, 6, 8, 10, or 14; and
   (b) a nucleic acid molecule comprising a nucleotide sequence having at least 95% sequence identity to the nucleotide sequence as set forth in SEQ ID NO: 2, 4, 6, 8, 10, or 14.

2. The isolated nucleic acid molecule of claim 1, wherein said polypeptide has antifungal activity against a fungi selected from the group consisting of *Colletotrichum graminkola*, *Diplodia maydis*, *Fusarium graminearum*, and *Fusarium vertkillioides*.

3. An expression cassette comprising the nucleic acid molecule of claim 1 operably linked to a promoter that drives expression in a microorganism.

4. A transformed microorganism comprising at least one expression cassette set forth in claim 3.

5. An antipathogenic composition comprising at least one transformed microorganism according to claim 4.

6. The composition of claim 5 further comprising a carrier.

7. A method for protecting a plant from a pathogen comprising applying the composition according to claim 6 to the environment of a plant pathogen, wherein said microorganism expresses said polypeptide having antifungal activity.

8. The method of claim 7, wherein said composition is applied by a procedure selected from the group consisting of spraying, dusting, broadcasting, and seed coating.

* * * * *

UNITED STATES PATENT AND TRADEMARK OFFICE
CERTIFICATE OF CORRECTION

| | |
|---|---|
| PATENT NO. | : 8,148,510 B2 |
| APPLICATION NO. | : 12/795770 |
| DATED | : April 3, 2012 |
| INVENTOR(S) | : Altier et al. |

It is certified that error appears in the above-identified patent and that said Letters Patent is hereby corrected as shown below:

On the face of the patent, (75) Inventors, the inventor Jennie Hunter-Cevera's address should be changed as follows:

"Elliott City, MD" should be --Ellicott City, MD--.

Column 16, line 44, "et at" should be --et al.--;

Column 22, line 27, "tissue-referred" should be --tissue-preferred--;

Column 23, line 56, "et at" should be --et al.--;

Column 24, line 1, "et at" should be --et al.--;

Column 27, line 56, "toperossing" should be --topcrossing--;

Column 28, line 64, "cassaya" should be --cassava--;

Column 35, line 4, "circinate" should be --circinata--;

Column 35, line 5, "alternate" should be --alternata--;

Column 35, line 11, "sorghid" should be --sorgi--;

Column 45, line 57, "55 by" should be --55 bp--;

Column 45, line 67, "124 by" should be --124 bp--;

Column 46, line 15, "124 by" should be --124 bp--;

Column 129, claim 2, line 42, "graminkola" should be --graminicola--; and

Column 129, claim 2, line 43, "vertkillioides" should be --verticillioides--.

Signed and Sealed this
Seventeenth Day of July, 2012

David J. Kappos
*Director of the United States Patent and Trademark Office*